(12) United States Patent
Roberts et al.

(10) Patent No.: US 12,275,945 B2
(45) Date of Patent: Apr. 15, 2025

(54) METHODS FOR IMPROVING PHOTOSYNTHETIC ORGANISMS

(71) Applicant: AGRESEARCH LIMITED, Canterbury (NZ)

(72) Inventors: Nicholas John Roberts, Feilding (NZ); Somrutai Winichayakul, Palmerston North (NZ); Zacharia D'Arcy Beechey-Gradwell, Palmerston North (NZ); Luke James Cooney, Waitarere Beach (NZ)

(73) Assignee: AGRESEARCH LIMITED, Canterbury (NZ)

( * ) Notice: Subject to any disclaimer, the term of this patent is extended or adjusted under 35 U.S.C. 154(b) by 33 days.

(21) Appl. No.: 17/755,168

(22) PCT Filed: Oct. 22, 2020

(86) PCT No.: PCT/IB2020/059915
§ 371 (c)(1),
(2) Date: Apr. 22, 2022

(87) PCT Pub. No.: WO2021/079297
PCT Pub. Date: Apr. 29, 2021

(65) Prior Publication Data
US 2022/0290174 A1 Sep. 15, 2022

(30) Foreign Application Priority Data
Oct. 25, 2019 (AU) .................................. 2019904013

(51) Int. Cl.
*C12N 15/82* (2006.01)
*C07K 14/415* (2006.01)
*C12N 9/10* (2006.01)

(52) U.S. Cl.
CPC ........ *C12N 15/8269* (2013.01); *C07K 14/415* (2013.01); *C12N 9/1029* (2013.01); *C12N 15/8273* (2013.01)

(58) Field of Classification Search
CPC ............ C12N 15/8269; C12N 15/8273; C07K 14/415
See application file for complete search history.

(56) References Cited

FOREIGN PATENT DOCUMENTS

WO  2011053169 A1  5/2011
WO  WO-2013022353 A1 *  2/2013  ............. A23K 10/30

OTHER PUBLICATIONS

Siloto, Rodrigo M P et al. "The accumulation of oleosins determines the size of seed oilbodies in *Arabidopsis*." The Plant cell vol. 18,8 (2006): 1961-74. doi:10.1105/tpc.106.041269 (Year: 2006).*
Winichayakul, Somrutai et al. "In vivo packaging of triacylglycerols enhances *Arabidopsis* leaf biomass and energy density." Plant physiology vol. 162,2 (2013): 626-39. doi:10.1104/pp.113.216820 (Year: 2013).*
Chen, Kang, et al. "Genome-wide identification and functional analysis of oleosin genes in *Brassica napus* L." BMC plant biology 19 (2019): 1-20. (Year: 2019).*
Fang, Yuan, Rui-Liang Zhu, and Brent D. Mishler. "Evolution of oleosin in land plants." PLoS One 9.8 (2014): e103806. (Year: 2014 ).*
Kim, Hyun Uk, et al. "A novel group of Oleosins is present inside the pollen of *Arabidopsis*." Journal of Biological Chemistry 277.25 ( 2002): 22677-22684. (Year: 2002).*
Tai, Sorgan SK, et al. "Gene family of oleosin isoforms and their structural stabilization in sesame seed oil bodies." Bioscience, biotechnology, and biochemistry 66.10 (2002): 2146-2153. (Year: 2002).*
Huang, Ming-Der, and Anthony H C Huang. "Bioinformatics Reveal Five Lineages of Oleosins and the Mechanism of Lineage Evolution Related to Structure/Function from Green Algae to Seed Plants." Plant physiology vol. 169, 1 (2015): 453-70. doi:10.1104/pp.15.00634 (Year: 2015).*
Lu, Yubin, et al. "Genome-wide identification, expression profiling, and functional validation of oleosin gene family in *Carthamus tinctorius* L." Frontiers in plant science 9 (2018): 1393. (Year: 2018).*
Huang, Chien-Yu, and Anthony HC Huang. "Unique motifs and length of hairpin in oleosin target the cytosolic side of endoplasmic reticulum and budding lipid droplet." Plant physiology 174.4 (2017): 2248-2260. (Year: 2017).*
Vanhercke, Thomas, et al. "Metabolic engineering of biomass for high energy density: oilseed-like triacylglycerol yields from plant leaves." Plant biotechnology journal 12.2 (2014): 231-239. (Year: 2014).*

(Continued)

*Primary Examiner* — Charles Logsdon
*Assistant Examiner* — Kelsey L McWilliams
(74) *Attorney, Agent, or Firm* — McKee, Voorhees & Sease, PLC

(57) ABSTRACT

The invention provides a method for reducing water soluble carbohydrate (WSC) in a photosynthetic cells and plants, the method comprising the step of genetically modifying the photosynthetic cells and plants to express a modified oleosin including at least one artificially introduced cysteine to reduce WSC. The applicants have shown that in such cells and plants, there is a strong correlation between reduced WSC and elevated photosynthesis. In addition, WSC is significantly simpler to measure that than the other typically measured characteristics when selecting cells or plants with the most favourable characteristics.

10 Claims, 11 Drawing Sheets
Specification includes a Sequence Listing.

(56) References Cited

OTHER PUBLICATIONS

Fan et al., "Dual Role for Phospholipid: Diacylglycerol Acyltransferase: Enhancing Fatty Acid Synthesis and Diverting Fatty Acids from Membrane Lipids to Triacylglycerol in *Arabidopsis* Leaves," The Plant Cell, Sep. 2013, vol. 25, pp. 3506-3518.

International Search Report in PCT/IB2020/059915, mailed Dec. 17, 2020, 7 pages.

Vanhercke et al., "Metabolic engineering of biomass for high energy density: oilseed-like triacylglycerol yields from blant leaves," Plant Biotechnology Journal, 2014, vol. 12, pp. 231-239.

Vanhercke et al., "Up-regulation of lipid biosynthesis increases the oil content in leaves of Sorghum bicolor," Plant Biotechnology Journal, 2019, vol. 17, pp. 220-232.

Winichayakul et al., "In Vivo Packaging of Triacylglycerols Enhances *Arabidopsis* Leaf Biomass and Energy Density," Plant Physiology, Jun. 2013, vol. 162, pp. 626-639.

Written Opinion in PCT/IB2020/059915, mailed Dec. 17, 2020, 5 pages.

Zulu et al., "Heterologous co-expression of a yeast diacylglycerol acyltransferase (ScDGA1) and a plant oleosin (AtOLEO3) as an efficient tool for enhancing triacylglycerol accumulation in the marine diatom Phaeodactylum tricornutum," Biotechnology for Biofuels, 2017, vol. 10, No. 187, pp. 1-14.

\* cited by examiner

METHODS FOR IMPROVING PHOTOSYNTHETIC ORGANISMS

CROSS REFERENCE TO RELATED APPLICATIONS

This is a U.S. National Phase application claiming priority to PCT/IB2020/059915, filed Oct. 22, 2020, which claims priority to foreign application AU/2019904013, filed Oct. 25, 2019, the entire contents of which are hereby expressly incorporated by reference in their entirety including, without limitation, the specification, claims, and abstract, as well as any figures, tables, or drawings thereof.

REFERENCE TO SEQUENCE LISTING SUBMITTED ELECTRONICALLY

The instant application contains a Sequence Listing which has been submitted electronically in ASCII format and is herein incorporated by reference in its entirety. Said ASCII text copy, created on Jan. 30, 2024, is named "P13888US00_SequenceListing.txt" and is 122,934 bytes in size.

TECHNICAL FIELD

The invention relates to methods enhancing $CO_2$ assimilation and other growth/yield characteristics in photosynthetic cells and plants.

BACKGROUND

The increasing global population presents demand for higher yielding crops with enhanced production (photosynthetic carbon assimilation).

Ribulose biphosphate carboxlase (Rubisco) is the key enzyme responsible for photosynthetic carbon assimilation. In the presence of $O_2$, Rubisco also performs an oxygenase reaction which initiates the photorespiratory cycle which results in an indirect loss of fixed nitrogen and $CO_2$ from the cell which need to be recovered. Genetic modification to increase the specificity of Rubisco for $CO_2$ relative to $O_2$ and to increase the catalytic rate of Rubisco in crop plants would be of great agronomic value. Parry et al, (2003) reviewed the progress to date, concluding that there are still many technical barriers to overcome and to date all engineering attempts have thus far failed to produce a better Rubisco (Peterhansel et al. 2008).

In nature, a number of higher plants (C4 plants) have evolved energy requiring mechanisms to increase the concentration of intracellular $CO_2$ in close proximity to Rubisco thereby increasing the proportion of carboxylase reactions. Maize for example has achieved this by a manipulation of the plant's architecture enabling a different initial process of fixing $CO_2$, known as C4 metabolism. The agronomic downside of this evolved modification is an increase in leaf fibre resulting in a comparatively poor digestibility of leaves from C4 plants. C4 photosynthesis is thought to be a product of convergent evolution having developed on separate occasions in very different taxa. However, this adaptation is only possible for multi-cellular organisms (and not for photosynthetic unicellular organisms such as algae). Algae have a variety of different mechanisms to concentrate $CO_2$; however, there appears to be a continuum in the degree to which the $CO_2$ concentration mechanism (CCM) is expressed in response to external dissolved inorganic carbon (DIC) concentration, with higher concentrations leading to a greater degree of suppression of CCM activity. Two reviews have covered the CCMs in algae as well as their modulation and mechanisms and are incorporated herein by reference (Giordano, Beardall et al. 2005; Moroney and Ynalvez 2007). The vascular plants that currently constituted the largest percentage of the human staple diet are C3 (rice and tubers) and not C4 plants. Similarly, many oil seed crops (canola, sunflower, safflower) and many meat and dairy animal feed crops (legumes, cereals, soy, forage grasses) are C3 plants.

Increasing the efficiency of $CO_2$ assimilation, should therefore concurrently increase abiotic stress tolerance and nitrogen use efficiency and would be of significant agronomical benefit for C3 plants and photosynthetic microorganisms.

Significant advances have been made via expressing modified oleosins including artificially introduced cysteines (cysteine-oleosins), in plants. In WO 2011/053169 the applicant demonstrated a significant increase in the level of oil produced in leaves. In WO/2013/022353 the applicant demonstrated an increase in the rate of $CO_2$ assimilation by reducing lipid recycling and/or via expressing cysteine-oleosins. However, the methods used selection of cells and plants with the most desirable $CO_2$ assimilation and characteristics remain challenging.

Selection via measuring: cysteine-oleosins production (e.g via immunoblotting with anti-oleosin antibodies), lipid production or ratios (e.g. via detection of fatty acid methyl esters [FAMES] using gas chromatography-flame ionization detection [GC-FID] or gas chromatography-mass spectrometry [GC-MS]), $CO_2$ exchange (e.g. via infred gas analysis [IRGA]) or relative growth rate have a number of drawbacks. These methods are time consuming, may require significant training or expertise, and often require the use of expensive equipment and/or consumables.

It is an object of the invention to provide methods for production and/or selection of photosynthetic cells or plants with improved $CO_2$ assimilation and/or growth/yield characteristics that overcome one or more of the limitations of methods of the prior art and/or at least provide the public with a useful choice.

SUMMARY OF THE INVENTION

The invention provides methods for reducing water soluble carbohydrate (WSC) in a photosynthetic cells and plants. The applicants have demonstrated that this can be achieved by expressing modified oleosins with artificially introduced cysteine residues in the photosynthetic cells and plants.

The applicants have shown that in such photosynthetic cells and plants, there is a strong correlation between between elevated photosynthesis and low WSC. This correlation is generally more striking than that shown between elevated photosynthesis and any of: level cysteine oleosin expression or accumulation, and lipid profile or level.

This in turn provides additional advantages in that WSC is significantly simpler to measure that than the other characteristics such as cysteine-oleosin production, lipid production and profile, elevated photosynthesis and relative growth rate, when selecting cells or plants with the most favourable characteristics.

General Method (Photosynthetic Cell)

In the first aspect the invention provides a method for reducing water soluble carbohydrate (WSC) in a photosynthetic cell, the method comprises the step of genetically modifying the photosynthetic cell to express a modified oleosin including at least one artificially introduced cysteine to reduce WSC.

In one embodiment reducing water-soluble carbohydrate (WSC) leads to increased $CO_2$ assimilation in the cell.

In a further aspect the invention provides a method for producing a photosynthetic cell with increased $CO_2$ assimilation, the method comprising modifying the photosynthetic cell to reduce water soluable carbohydrate (WSC).

In one embodiment the method comprises the step of genetically modifying the photosynthetic cell to express a modified oleosin including at least one artificially introduced cysteine to reduce WSC In one embodiment reducing water soluble carbohydrate (WSC) leads to increased $CO_2$ assimilation in the cell.

In a further embodiment the photosynthetic cell is also modified to express at least one triacylglycerol (TAG) synthesizing enzyme.

In a further embodiment expression of the modified oleosin including at least one artificially introduced cysteine and the TAG synthesizing enzyme leads to the reducing water soluble carbohydrate (WSC).

Without wishing to be bound by theory, the applicants postulate that expression of the modified oleosin including at least one artificially introduced cysteine, or the expression of the modified oleosin including at least one artificially introduced cysteine and the TAG synthesizing enzyme leads to the production of a carbon microsink. This leads to certain embodiments of the invention.

In a further embodiment expression of the modified oleosin including at least one artificially introduced cysteine and the TAG synthesizing enzyme leads to the production of the carbon microsink.

In a further embodiment production of the the carbon microsink causes a reduction in the level of water soluable carbohydrate (WSC).

Method Includes the Step of Measuring WSC in the Photosynthetic Cell

In one embodiment the method includes the step of measuring water soluble carbohydrates in the photosynthetic cell.

In a further embodiment measuring reduced water soluble carbohydrates is indicative of increased $CO_2$ assimilation in the photosynthetic cell.

Level of Decrease in WSC in the Photosynthetic Cell

In one embodiment WSC is decreased by at least 1%, more preferably at least 2%, more preferably at least 3%, more preferably at least 4%, more preferably at least 5%, more preferably at least 10%, more preferably at least 15%, more preferably at least 20%, more preferably at least 25%, more preferably at least 30%, more preferably at least 35%, more preferably at least 40%, more preferably at least 45%, more preferably at least 50%, more preferably at least 60%, more preferably at least 70%, more preferably at least 80%, more preferably at least 90%, relative to a control photosynthetic cell.

In one embodiment WSC decrease is in the range of 1% to 95%, more preferably 10% to 90%, more preferably 20% to 80%, more preferably 30% to 70%, more preferably 40% to 60%, relative to a control photosynthetic cell.

Period of Decrease in WSC in the Photosynthetic Cell

In one embodiment the decrease in WSC is sustained for at least 1, preferably at least 2, more preferably at least 3, more preferably at least 4, more preferably at least 5, more preferably at least 6, more preferably at least 7, more preferably at least 8 hours.

In a further embodiment the decrease in WSC is sustained for at least 30 minutes, preferably at least 1 hour, more preferably at least 2, more preferably at least 3, more preferably at least 4, either side of the circadian peak maximum WSC assimilation of a control photosynthetic cell.

In a further embodiment the decrease in WSC is sustained for at least 30 minutes, preferably at least 1 hour, more preferably at least 2, more preferably at least 3, more preferably at least 4, either side of midday.

In a further embodiment the decrease in WSC as described above is repeated daily over a period of at least 2, more preferably at least 3, more preferably at least 4, more preferably at least 5, more preferably at least 6, more preferably at least 7 days.

In a further embodiment the decrease in WSC as described above is repeated daily for the life of the plant.

In a further embodiment the method of the invention includes measuring the level or period of reduction in WSC as described above.

Water Soluble Carbohydrate (WSC)

The term "water soluble carbohydrate (WSC) includes simple sugars sucrose/glucose and the larger forms such as starch and fructans. Those skilled in the art will understand that the type of WSC is species dependent. For example, some species make starch or and others make fructan.

Conditions Under which Phenotypes are Expressed and/or Measured in Photosynthetic Cell In a further embodiment the reduction in WSC is exhibited under strong light.

In one embodiment the reduction is WSC is exhibited at least 10, preferably at least 50, preferably at least 100, preferably at least 200, preferably at least 300, preferably at least 400, preferably at least 500, preferably at least 600, preferably at least 700, preferably at least 800, preferably at least 900, preferably at least 1000, preferably at least 1250, preferably at least 1500, preferably at least 1750, preferably at least 2000, preferably at least 2500, preferably at least 3000, preferably at least 4000, preferably at least 5000, preferably at least 6000, preferably at least 7000, preferably at least 8000, preferably at least 9000, preferably at least 10000 $\mu mol\ m^{-2}\ s^{-1}$ of photosynthetically active radiation.

Those skilled in the art will understand that the photosynthetically active radiation can be provided by the sun, or through artificial light sources (e.g. LED lighting) well known to art-skilled workers.

In a further embodiment the reduction in WSC is exhibited under light saturation.

Those skilled in the art will understand that light saturation occurs when light is no longer a limiting factor for maximum $CO_2$ fixation. Those skilled in the art will also understand that is species dependent.

Carbon Microsink

In one embodiment the carbon microsink is an accumulation of lipid.

In a further embodiment the carbon microsink comprises at least one oil body.

Level of Increase in $CO_2$ Assimilation in the Photosynthetic Cell

In one embodiment the rate of $CO_2$ assimilation is increased by at least 1%, more preferably at least 2%, more preferably at least 3%, more preferably at least 4%, more preferably at least 5%, more preferably at least 10%, more preferably at least 15%, more preferably at least 20%, more preferably at least 25%, more preferably at least 30%, more preferably at least 35%, more preferably at least 40%, more preferably at least 45%, more preferably at least 50%, relative to a control photosynthetic cell.

In one embodiment the rate of $CO_2$ assimilation increase is in the range of 1% to 50%, more preferably 2% to 40%, more preferably 3% to 30%, more preferably 4% to 25%, more preferably 5% to 20%, relative to a control photosynthetic cell.

Period of Increase in $CO_2$ Assimilation in the Photosynthetic Cell

In one embodiment the increase in the rate of $CO_2$ assimilation is sustained for at least 1, preferably at least 2, more preferably at least 3, more preferably at least 4, more preferably at least 5, more preferably at least 6, more preferably at least 7, more preferably at least 8 hours.

In a further embodiment the increase in the rate of $CO_2$ assimilation is sustained for a least 30 minutes, preferably at least 1 hour, more preferably at least 2, more preferably at least 3, more preferably at least 4, either side of the circadian peak maximum WSC assimilation of a control photosynthetic cell.

In a further embodiment the increase in the rate of $CO_2$ assimilation is sustained for at least 30 minutes, preferably at least 1 hour, more preferably at least 2, more preferably at least 3, more preferably at least 4, either side of midday.

In a further embodiment the increase in the rate of $CO_2$ assimilation as described above is repeated daily over a period of at least 2, more preferably at least 3, more preferably at least 4, more preferably at least 5, more preferably at least 6, more preferably at least 7 days.

In a further embodiment the increase in the rate of $CO_2$ assimilation as described above is repeated daily for the life of the cell.

Other Associated Phenotypes of the Photosynthetic Cell

In a further embodiment, in addition to the increased rate of $CO_2$ assimilation the method produces a photosynthetic cell with at least one of:
 a) an increased rate of photosynthesis,
 b) increased water use efficiency,
 c) an increased growth rate,
 d) increased nitrogen use efficiency,
 e) decreased loss of fixed carbon, and
 f) no acclamation of photosynthesis to elevated $CO_2$ environments.

Preferably the photosynthetic cell produced has all of a) to f).

Genetic Modification of Photosynthetic Cells to Express a Modified Oleosin Including at Least One Artificially Introduced Cysteine In one embodiment the method includes the step of modifying an endogenous oleosin-encoding polynucleotide in the photosynthetic cell or plant to produce a polynucleotide encoding the modified oleosin. Methods for modifying endogenous polynucleotides are well known to those skilled in the art, and are described further herein.

In one embodiment the method includes the step of introducing into the photosynthetic cell, a polynucleotide encoding a modified oleosin including at least one artificially introduced cysteine.

In one embodiment the method includes the step of transforming the photosynthetic cell with a polynucleotide encoding the modified oleosin including at least one artificially introduced cysteine.

Genetic modification of photosynthetic cells to express at least one triacylglycerol (TAG) synthesizing enzyme.

In one embodiment the method includes the step of modifying an endogenous TAG synthesizing gene in the photosynthetic cell to bring about increased expression of the TAG synthesizing enzyme. For example, modification of regulatory sequences in the gene can be modified to increase expression of the TAG synthesizing enzyme. Methods for modifying endogenous polynucleotides are well known to those skilled in the art, and are described further herein.

In one embodiment the method includes the step of introducing into the photosynthetic cell, a polynucleotide encoding the TAG synthesizing enzyme.

In one embodiment the method includes the step of transforming the photosynthetic cell with a polynucleotide encoding the TAG synthesizing enzyme.

Polynucleotide is Part of a Genetic Construct

In one embodiment the polynucleotide encoding the modified oleosin, or TAG synthesizing enzyme, is transformed as part of a genetic construct. Preferably the genetic construct is an expression construct. Preferably the expression construct includes the polynucleotide operably linked to a promoter. In a further embodiment the polynucleotide is operably linked to a terminator sequence.

Promoters

In one embodiment the promoter is capable of driving expression of the polynucleotide in a photosynthetic cell. In one embodiment the promoter drives expression of the polynucleotide preferentially in photosynthetic cells. In one embodiment the promoter is a photosynthetic cell preferred promoter. In a further embodiment the promoter is a photosynthetic cell specific promoter. In a further embodiment the promoter is a light regulated promoter.

It will be understood by those skilled in the art that the polynucleotide encoding the modified oleosin and the nucleic acid sequence encoding a triacylglycerol (TAG) synthesizing enzyme can be placed on the same construct or on separate constructs to be transformed into the photosynthetic cell. Expression of each can be driven by the same or different promoters, which may be included in the construct to be transformed. It will also be understood by those skilled in the art that alternatively the polynucleotide and nucleic acid can be transformed into the photosynthetic cell without a promoter, but expression of either or both of the polynucleotide and nucleic acid could be driven by a promoter or promoters endogenous to the cell transformed.

Those skilled in the art will understand that polynucleotides and constructs for expressing polypeptides in cells and plants can include various other modifications including restriction sites, recombination/excision sites, codon optimisation, tags to facilitate protein purification, etc. Those skilled in the art will understand how to utilise such modifications, some of which may influence transgene expression, stability and translation. However, an art skilled worker would also understand that these modifications are not essential, and do not limit the scope of the invention.

General Method in a Plant

In one embodiment the photosynthetic cell is part of a plant.

Thus in a further aspect the invention provides a method for reducing water soluble carbohydrate (WSC) in a plant, the method comprises the step of genetically modifying the plant to express a modified oleosin including at least one artificially introduced cysteine to reduce WSC.

In one embodiment reducing water-soluble carbohydrate (WSC) leads to increased $CO_2$ assimilation in the cell.

In a further aspect the invention provides a method for producing a plant with increased $CO_2$ assimilation, the method comprising modifying the plant to reduce water soluble carbohydrate (WSC).

In one embodiment the method comprises the step of genetically modifying the plant to express a modified oleosin including at least one artificially introduced cysteine to reduce WSC In one embodiment reducing water soluble carbohydrate (WSC) leads to increased $CO_2$ assimilation in the cell.

In a further embodiment the plant is also modified to express at least one triacylglycerol (TAG) synthesizing enzyme.

In a further embodiment expression of the modified oleosin including at least one artificially introduced cysteine and the TAG synthesizing enzyme leads to the reducing water soluble carbohydrate (WSC).

Without wishing to be bound by theory, the applicants postulate that expression of the modified oleosin including at least one artificially introduced cysteine, or the expression of the modified oleosin including at least one artificially introduced cysteine and the TAG synthesizing enzyme leads to the production of a carbon microsink. This leads to certain embodiments of the invention.

In a further embodiment expression of the modified oleosin including at least one artificially introduced cysteine and the TAG synthesizing enzyme leads to the production of the carbon microsink.

In a further embodiment production of the carbon microsink causes a reduction in the level of water soluble carbohydrate (WSC).

Method Includes the Step of Measuring WSC in the Plant

In one embodiment the method includes the step of measuring water soluble carbohydrates in the plant.

In a further embodiment measuring reduced water soluble carbohydrates is indicative of increased $CO_2$ assimilation in the plant.

Level of Decrease in WSC in the Plant

In one embodiment WSC is decreased by at least 1%, more preferably at least 2%, more preferably at least 3%, more preferably at least 4%, more preferably at least 5%, more preferably at least 10%, more preferably at least 15%, more preferably at least 20%, more preferably at least 25%, more preferably at least 30%, more preferably at least 35%, more preferably at least 40%, more preferably at least 45%, more preferably at least 50%, more preferably at least 60%, more preferably at least 70%, more preferably at least 80%, more preferably at least 90%, relative to a control photosynthetic plant.

In one embodiment WSC decrease is in the range of 1% to 95%, more preferably 10% to 90%, more preferably 20% to 80%, more preferably 30% to 70%, more preferably 40% to 60%, relative to a control plant.

Period of Decrease in WSC in the Plant

In one embodiment the decrease in WSC is sustained for at least 1, preferably at least 2, more preferably at least 3, more preferably at least 4, more preferably at least 5, more preferably at least 6, more preferably at least 7, more preferably at least 8 hours.

In a further embodiment the decrease in WSC is sustained for least 30 minutes, preferably at least 1 hour, more preferably at least 2, more preferably at least 3, more preferably at least 4, either side of the circadian peak maximum WSC assimilation of a control plant.

In a further embodiment the decrease in WSC is sustained for a least 30 minutes, preferably at least 1 hour, more preferably at least 2, more preferably at least 3, more preferably at least 4, either side of midday.

In a further embodiment the decrease in WSC as described above is repeated daily over a period of at least 2, more preferably at least 3, more preferably at least 4, more preferably at least 5, more preferably at least 6, more preferably at least 7 days.

In a further embodiment the decrease in WSC as described above is repeated daily for the life of the plant.

In a further embodiment the method of the invention includes measuring the level or period of reduction in WSC as described above.

In one embodiment lowering the peak level of WSC accumulation reduces the negative feedback placed on the photosynthetic machinery, which would ordinarily prevent the over accumulation of WSC and minimise resources required to maintain the photosynthetic machinery.

Conditions Under which Phenotypes are Expressed and/or Measured in Plant

In a further embodiment the reduction in WSC is exhibited under strong light.

In one embodiment the reduction is WSC is exhibited at least 10, preferably at least 50, preferably at least 100, preferably at least 200, preferably at least 300, preferably at least 400, preferably at least 500, preferably at least 600, preferably at least 700, preferably at least 800, preferably at least 900, preferably at least 1000, preferably at least 1250, preferably at least 1500, preferably at least 1750, preferably at least 2000, preferably at least 2500, preferably at least 3000, preferably at least 4000, preferably at least 5000, preferably at least 6000, preferably at least 7000, preferably at least 8000, preferably at least 9000, preferably at least 10000 µmol m$^{-2}$ s$^{-1}$ of photosynthetically active radiation.

In a further embodiment the reduction in WSC is exhibited under light saturation.

Those skilled in the art will understand that light saturation occurs when light is no longer a limiting factor for maximum $CO_2$ fixation. Those skilled in the art will also understand that is species dependent.

Carbon Microsink

In one embodiment the carbon microsink is an accumulation of lipid.

In a further embodiment the carbon microsink comprises at least one oil body.

Level of Increase in $CO_2$ Assimilation in the Plant

In one embodiment the rate of $CO_2$ assimilation is increased by at least 1%, more preferably at least 2%, more preferably at least 3%, more preferably at least 4%, more preferably at least 5%, more preferably at least 10%, more preferably at least 15%, more preferably at least 20%, more preferably at least 25%, more preferably at least 30%, more preferably at least 35%, more preferably at least 40%, more preferably at least 45%, more preferably at least 50%, relative to a control plant.

In one embodiment the rate of $CO_2$ assimilation increase is in the range of 1% to 50%, more preferably 2% to 40%, more preferably 3% to 30%, more preferably 4% to 25%, more preferably 5% to 20%, relative to a control plant.

Period of Increase in $CO_2$ Assimilation in the Plant

In one embodiment the increase in the rate of $CO_2$ assimilation is sustained for at least 1, preferably at least 2, more preferably at least 3, more preferably at least 4, more preferably at least 5, more preferably at least 6, more preferably at least 7, more preferably at least 8 hours.

In a further embodiment the increase in the rate of $CO_2$ assimilation is sustained for at least 30 minutes, preferably at least 1 hour, more preferably at least 2, more preferably at least 3, more preferably at least 4, either side of the circadian peak maximum $CO_2$ assimilation of a control plant.

In a further embodiment the increase in the rate of $CO_2$ assimilation is sustained for at least 30 minutes, preferably at least 1 hour, more preferably at least 2, more preferably at least 3, more preferably at least 4, either side of midday.

In a further embodiment the increase in the rate of $CO_2$ assimilation as described above is repeated daily over a period of at least 2, more preferably at least 3, more preferably at least 4, more preferably at least 5, more preferably at least 6, more preferably at least 7 days.

In a further embodiment the increase in the rate of $CO_2$ assimilation as described above is repeated daily for the life of the plant.

Other Associated Phenotypes of the Plant

In a further embodiment, in addition to the increased rate of $CO_2$ assimilation the plant also has at least one of:
 a) an increased rate of photosynthesis, and
 b) increased water use efficiency, and
 c) an increased growth rate.
Preferably the plant has all of a) to c).

In a further embodiment, in addition to the increased rate of $CO_2$ assimilation the plant also has at least one of:
 d) increased biomass,
 e) delayed flowering,
 f) increased chloroplast $CO_2$ concentration,
 g) a decreased rate of photorespiration,
 h) increased seed, fruit or storage organ yield,
 i) increased nitrogen use efficiency, and
 j) decreased loss of fixed carbon.
Preferably the plant has all of a) to j).

In one embodiment biomass is increased by at least 5%, preferably by at least 10%, preferably by at least 20%, preferably by at least 30%, preferably by at least 40%, preferably by at least 50%, preferably by at least 60% relative to a control plant.

In one embodiment the increase in biomass is in the range 2% to 100%, preferably 4% to 90%, preferably 6% to 80%, preferably 8% to 70%, preferably 10% to 60% relative to a control plant.

Genetic Modification of Plants to Express a Modified Oleosin Including at Least One Artificially Introduced Cysteine In one embodiment the method includes the step of modifying an endogenous oleosin-encoding polynucleotide in the plant to produce a polynucleotide encoding the modified oleosin. Methods for modifying endogenous polynucleotides are well known to those skilled in the art, and are described further herein.

In one embodiment the method includes the step of introducing into the plant, a polynucleotide encoding a modified oleosin including at least one artificially introduced cysteine.

In one embodiment the method includes the step of transforming the plant with a polynucleotide encoding the modified oleosin including at least one artificially introduced cysteine.

Genetic Modification of Plants to Express at Least One Triacylglycerol (TAG) Synthesizing Enzyme.

In one embodiment the method includes the step of modifying an endogenous TAG synthesising gene in the plant to bring about increased expression of the TAG synthesizing enzyme. For example, modification of regulatory sequences in the gene can be modified to increase expression of the TAG synthesizing enzyme. Methods for modifying endogenous polynucleotides are well known to those skilled in the art, and are described further herein.

In one embodiment the method includes the step of introducing into the plant, a polynucleotide encoding the TAG synthesizing enzyme.

In one embodiment the method includes the step of transforming the plant with a polynucleotide encoding the TAG synthesizing enzyme.

Polynucleotide is Part of a Genetic Construct

In one embodiment the polynucleotide encoding the modified oleosin, or TAG synthesizing enzyme, is transformed as part of a genetic construct. Preferably the genetic construct is an expression construct. Preferably the expression construct includes the polynucleotide operably linked to a promoter. In a further embodiment the polynucleotide is operably linked to a terminator sequence.

Promoters for Plants

In one embodiment the promoter operably linked to the polynucleotide is capable of driving expression of the polynucleotide in a photosynthetic tissue of a plant. In one embodiment the promoter is a photosynthetic cell preferred promoter. In a further embodiment the promoter is a photosynthetic cell specific promoter. In a further embodiment the promoter is capable of driving expression of the polynucleotide in a vegetative photosynthetic tissue of a plant. In a further embodiment the promoter is capable of driving expression of the polynucleotide in a leaf of a plant.

It will be understood by those skilled in the art that the polynucleotide encoding the modified oleosin and the nucleic acid sequence encoding a triacylglycerol (TAG) synthesizing enzyme can be placed on the same construct or on separate constructs to be transformed into the plant. Expression of each can be driven by the same or different promoters, which may be included in the construct to be transformed. It will also be understood by those skilled in the art that alternatively the polynucleotide and nucleic acid can be transformed into the plant without a promoter, but expression of either or both of the polynucleotide and nucleic acid could be driven by a promoter or promoters endogenous to the plant transformed.

Modified Oleosins

In one embodiment, the modified oleosin includes at least two cysteines, at least one of which is artificially introduced. In a further embodiment, the modified oleosin includes at least two to at least thirteen (i.e., 2, 3, 4, 5, 6, 7, 8, 9, 10, 11, 12, 13, 14 or more) artificially introduced cysteines. In one embodiment the cysteines are artificially introduced into the N-terminal hydrophilic region of the oleosin, or into the C-terminal hydrophilic region of the oleosin. In a further embodiment the modified oleosin includes at least one cysteine in the N-terminal hydrophilic region, and at least one cysteine in the C-terminal hydrophilic region. In a further embodiment the cysteines are distributed substantially evenly over the N-terminal and C-terminal hydrophilic regions of the oleosin. In a further embodiment the cysteines are distributed evenly over the N-terminal and C-terminal hydrophilic regions of the oleosin.

Preferably the modified oleosin includes at least one artificially introduced cysteine, wherein the cysteine is introduced into at least one of:
 a) in the N-terminal hydrophilic region of the oleosin, and
 b) in the C-terminal hydrophilic region of the oleosin.

Photosynthetic Cell Types

The photosynthetic cell may be of any type. In one embodiment the photosynthetic cell is a prokaryotic cell. In a further embodiment the photosynthetic cell is a eukaryotic cell. In one embodiment the photosynthetic cell is selected from a photosynthetic bacterial cell, a photosynthetic yeast cell, a photosynthetic fungal cell, a photosynthetic algal cell, and a plant cell. In one embodiment the photosynthetic cell is a bacterial cell. In a further embodiment the photosynthetic cell is a yeast cell. In further embodiment the photosynthetic cell is a fungal cell. In further embodiment the photosynthetic cell is an algal cell.

Photosynthetic Cell is an Algal Cell

In a preferred embodiment the photosynthetic cell is an algal cell. In one embodiment the photosynthetic algal cell is an algal cell selected from one of the following divisions: Chlorophyta (green algae), Rhodophyta (red algae), Phaeophyceae (brown algae), Bacillariophycaeae (diatoms), and Dinoflagellata (dinoflagellates).

In one embodiment the algal cell shows an increased growth rate, relative to a control algal cell, at an elevated concentration of oxygen ($O_2$).

In a further embodiment, the concentration of $O_2$ is elevated to at least 1.1 times air saturation, more preferably at least 1.5 times air saturation, more preferably at least 2 times air saturation, more preferably at least 4 times air saturation, more preferably at least 8 times air saturation, more preferably at least 16 times air saturation.

In a further embodiment, the increased growth rate of the algal cell is at least 10%, more preferably at least 20%, more preferably at least 30%, more preferably at least 40%, more preferably at least 50%, more preferably at least 60%, more preferably at least 70%, more preferably at least 80%, more preferably at least 90%, more preferably at least 100% more than the growth rate of a control algal cell at the same $O_2$ concentration.

In a further embodiment, the increased growth rate of the algal cell is in the range 10% to about 130% more preferably 20% to 120%, more preferably 30% to 110%, more preferably 40% to 100%, more preferably 50% to 90%, more than the growth rate of a control algal cell at the same $O_2$ concentration.

Source of Oleosins and Plants

The modified oleosins may be modified naturally occurring oleosins. The plants from which the un-modified oleosin sequences are derived may be from any plant species that contains oleosins and polynucleotide sequences encoding oleosins.

The plant cells, in which the modified oleosins are expressed, may be from any plant species. The plants, in which the modified oleosins are expressed, may be from any plant species.

In one embodiment the plant cell or plant, is derived from a gymnosperm plant species. In a further embodiment the plant cell or plant, is derived from an angiosperm plant species. In a further embodiment the plant cell or plant, is derived from a from dicotyledonous plant species. In a further embodiment the plant cell or plant, is derived from a monocotyledonous plant species.

Preferred plant species are those that produce tubers (modified stems) such as but not limited to *Solanum* species. Other preferred plant species are those that produce bulbs (below ground storage leaves) such as but not limited to *Lilaceae, Amaryllis, Hippeastrum, Narcissus, Iridaceae*, and *Oxalis* species. Other preferred plant species are those that produce corms (swollen underground stems) such as but not limited to *Musa, Elocharis, Gladiolus* and *Colocasia* species. Other preferred plant species are those that produce rhizomes (underground storage stem) such as but not limited to *Asparagus, Zingiber* and *Bambuseae* species. Other preferred are those that produce substantial endosperm in their seeds, such as but not limited to maize and sorghum.

Preferred plants include those from the following genera: *Brassica, Solanum, Raphanus, Allium, Foeniculum, Lilaceae, Amaryllis, Hippeastrum, Narcissus, Iridaceae, Oxalis, Musa, Eleocharis, Gladiolus, Colocasia, Asparagus, Zingiber*, and *Bambuseae*.

A preferred *Brassica* species is *Brassica rapa* var. *rapa* (turnip)

Preferred *Solanum* species are those which produce tubers. A preferred *Solanum* species is *Solanum tuberosum* (potato)

Preferred *Raphanus* species include *Raphanus raphanistrum, Raphanus caudatu*, and *Raphanus sativus*. A preferred *Raphanus* species is *Raphanus sativus* (radish)

Preferred *Allium* species include: *Allium cepa* (onion, shallot), *Allium fistulosum* (bunching onion), *Allium schoenoprasum* (chives), *Allium tuberosum* (Chinese chives), *Allium ampeloprasum* (leek, kurrat, great-headed garlic, pearl onion), *Allium sativum* (garlic) and *Allium chinense* (rakkyo). A preferred *Allium* species is *Allium cepa* (onion)

Preferred *Musa* species include: *Musa acuminata* and *Musa balbisiana*. A preferred *Musa* species is *Musa acuminata* (banana, plantains)

A preferred *Zingiber* species is *Zingiber officinale* (ginger)

A preferred *Oxalis* species is *Oxalis tuberosa* (yam)

A preferred *Colocasia* species is *Colocasia esculenta* (taro).

Another preferred genera is *Zea*. A preferred *Zea* species is *Zea mays*.

Another preferred genera is *Sorghum*. A preferred *Sorghum* species is *Sorghum bicolor*.

Other preferred plants are forage plant species from a group comprising but not limited to the following genera: *Zea, Lolium, Hordium, Miscanthus, Saccharum, Festuca, Dactylis, Bromus, Thinopyrum, Trifolium, Medicago, Pheleum, Phalaris, Holcus, Glycine, Lotus, Plantago* and *Cichorium*.

Other preferred plants are leguminous plants. The leguminous plant or part thereof may encompass any plant in the plant family Leguminosae or Fabaceae. For example, the plants may be selected from forage legumes including, alfalfa, clover; leucaena; grain legumes including, beans, lentils, lupins, peas, peanuts, soy bean; bloom legumes including lupin, pharmaceutical or industrial legumes; and fallow or green manure legume species.

A particularly preferred genus is *Trifolium*. Preferred *Trifolium* species include *Trifolium repens; Trifolium arvense; Trifolium affine*; and *Trifolium occidentale*. A particularly preferred *Trifolium* species is *Trifolium repens*.

Another preferred genus is *Medicago*. Preferred *Medicago* species include *Medicago sativa* and *Medicago truncatula*. A particularly preferred *Medicago* species is *Medicago sativa*, commonly known as alfalfa.

Another preferred genus is *Glycine*. Preferred *Glycine* species include *Glycine max* and *Glycine wightii* (also known as *Neonotonia wightii*). A particularly preferred *Glycine* species is *Glycine max*, commonly known as soy bean. A particularly preferred *Glycine* species is *Glycine wightii*, commonly known as perennial soybean.

Another preferred genus is *Vigna*. A particularly preferred *Vigna* species is *Vigna unguiculata* commonly known as cowpea.

Another preferred genus is *Mucana*. Preferred *Mucana* species include *Mucana pruniens*. A particularly preferred *Mucana* species is *Mucana pruniens* commonly known as velvetbean.

Another preferred genus is *Arachis*. A particularly preferred *Arachis* species is *Arachis glabrata* commonly known as perennial peanut.

Another preferred genus is *Pisum*. A preferred *Pisum* species is *Pisum sativum* commonly known as pea.

Another preferred genus is *Lotus*. Preferred *Lotus* species include *Lotus corniculatus, Lotus pedunculatus, Lotus glabar, Lotus tenuis* and *Lotus uliginosus*. A preferred *Lotus* species is *Lotus corniculatus* commonly known as Birdsfoot Trefoil. Another preferred *Lotus* species is *Lotus glabar* commonly known as Narrow-leaf Birdsfoot Trefoil. Another preferred *Lotus* species is *Lotus pedunculatus* commonly known as Big trefoil. Another preferred *Lotus* species is *Lotus tenuis* commonly known as Slender trefoil.

Another preferred genus is *Brassica*. A preferred *Brassica* species is *Brassica oleracea*, commonly known as forage kale and cabbage.

Other preferred species are oil seed crops including but not limited to the following genera: *Brassica, Carthumus, Helianthus, Zea* and *Sesamum*.

A preferred oil seed genera is *Brassica*. A preferred oil seed species is *Brassica napus*.

A preferred oil seed genera is *Brassica*. A preferred oil seed species is *Brassica oleraceae*.

A preferred oil seed genera is *Carthamus*. A preferred oil seed species is *Carthamus tinctorius*.

A preferred oil seed genera is *Helianthus*. A preferred oil seed species is *Helianthus annuus*.

A preferred oil seed genera is *Zea*. A preferred oil seed species is *Zea mays*.

A preferred oil seed genera is *Sesamum*. A preferred oil seed species is *Sesamum indicum*. A preferred silage genera is *Zea*. A preferred silage species is *Zea mays*.

A preferred grain producing genera is *Hordeum*. A preferred grain producing species is *Hordeum vulgare*.

A preferred grazing genera is *Lolium*. A preferred grazing species is *Lolium perenne*. A preferred grazing genera is *Lolium*. A preferred grazing species is *Lolium arundinaceum*.

A preferred grazing genera is *Trifolium*. A preferred grazing species is *Trifolium repens*.

A preferred grazing genera is *Hordeum*. A preferred grazing species is *Hordeum vulgare*.

Preferred plants also include forage, or animal feedstock plants. Such plants include but are not limited to the following genera: *Miscanthus, Saccharum, Panicum*.

A preferred biofuel genera is *Miscanthus*. A preferred biofuel species is *Miscanthus giganteus*. A preferred biofuel genera is *Arundo*. A preferred biofuel species is *Arundo donax*.

A preferred biofuel genera is *Saccharum*. A preferred biofuel species is *Saccharum officinarum*.

A preferred biofuel genera is *Panicum*. A preferred biofuel species is *Panicum virgatum*.

In one embodiment the plant is a C3 plant.

In one embodiment the plant is selected from: rice, soybean, wheat, rye, oats, millet, barley, potato, canola, sunflower and safflower.

Preferred plants include those from the following genera: *Oryza, Glycine, Hordeum, Secale, Avena, Pennisetum, Setaria, Panicum, Eleusine, Solanum, Brassica, Helianthus* and *Carthamus*.

Preferred *Oryza* species include *Oryza sativa* and *Oryza minuta*.

Preferred *Glycine* species include *Glycine max* and *Glycine wightii* (also known as *Neonotonia wightii*).

A particularly preferred *Glycine* species is *Glycine max*, commonly known as soybean. A particularly preferred *Glycine* species is *Glycine wightii*, commonly known as perennial soybean.

A preferred *Hordeum* species is *Hordeum vulgare*.

Preferred *Triticum* species include *Triticum aestivum, Triticum durum* and *Triticum monococcum*.

A preferred *Secale* species is *Secale cereal*.

A preferred *Avena* species is *Avena sativa*.

Preferred millet species include *Pennisetum glaucum, Setaria italica, Panicum miliaceum* and *Eleusine coracana*.

Preferred *Solanum* species include *Solanum habrochaites, Solanum lycopersicum, Solanum nigrum*, and *Solanum tuberosum*.

Preferred *Brassica* species include *Brassica napus, Brassica campestris* and *Brassica Rapa*.

Preferred *Helianthus* species include *Helianthus annuus* and *Helianthus argophyllus*.

A preferred *Carthamus* species is *Carthamus tinctorius*

In one embodiment the plant is a C4 plant.

Preferred C4 plants include those selected from the genera: *Sorghum, Zea, Saccharum* (sugarcane), *Miscanthus* and *Arundo*.

Preferred *Sorghum* species include *Sorghum bicolor* and *Sorghum propinquum*

A preferred *Zea* species is *Zea mays* (maize)

A preferred *Saccharum* species is *Saccharum officinarum*.

A preferred *Arundo* is *Arundo donax*.

Suitable control plants include non-transformed or wild-type versions of plant of the same variety and/or species as the transformed plant used in the method of the invention. Suitable control plants also include plants of the same variety and or species as the transformed plant that are transformed with a control construct. Suitable control plants also include plants that have not been transformed with a polynucleotide encoding a modified oleosin including at least one artificially introduced cysteine. Suitable control plants also include plants that do not express a modified oleosin including at least one artificially introduced cysteine.

DETAILED DESCRIPTION OF THE INVENTION

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

Water Soluable Carbohydrates

The term "water soluble carbohydrates" (WSC) includes but is not limited to monosaccharaides, disaccharides, oligosaccharides, and a small and large fraction fructans. WSC includes but is not limited to sugars such as fructans, sucrose, glucose and fructose, and starch. Those skilled in the art will understand that the type of WSC is species dependent. For example, some species make starch or and others make fructan.

Methods for Measuring Water Soluable Carbohydrates

Methods for measuring water-soluble carbohydrates are well-known to those skilled in the art. Such methods can be applied to any species of interest. Some generic references include: Yemm and Willis, 1954, Biochem J. 1954 July; 57 (3): 508-514.

Such methods have been routinely applied to numerous species, for example soybean (Dunphy, Edward James, (1972). Retrospective Theses and Dissertations. 4732.), maize (Fiala, V., 1990, New Phytol. 115, 609-615), wheat (Hou, J et al., 2018, Journal of Plant Physiology, Volume 231, December 2018, Pages 182-191), ryegrass (Easton, H. et al., 2019 Proceedings of New Zealand Grassland Association 71, 161-166). Further methodology is described in the Examples section of the present specification. These are merely examples and do not limit the scope of the invention.

TAG Biosynthesis, Oil Bodies and Oleosins

On a weight for weight basis lipids have approximately double the energy content of either proteins or carbohydrates. The bulk of the world's lipids are produced by plants and the densest form of lipid is as a triacylglycerol (TAG). Dicotyledonous plants can accumulate up to approximately 60% of their seed weight as TAG which is subsequently used as an energy source for germination.

The TAG produced in developing seeds is typically contained within discreet structures called oil bodies (OBs) which are highly stable and remain as discrete tightly packed organelles without coalescing even when the cells desiccate or undergo freezing conditions (Siloto et al., 2006; Shimada et al., 2008). OBs consist of a TAG core surrounded by a phospholipid monolayer embedded with proteinaceous emulsifiers. The latter make up 0.5-3.5% of the OB; of this, 80-90% is oleosin with the remainder predominantly consisting of the calcium binding (caloleosin) and sterol binding (steroleosin) proteins (Lin and Tzen, 2004). The emulsification properties of oleosins derives from their three functional domains which consist of an amphipathic N-terminal arm, a highly conserved central hydrophobic core (~72 residues) and a C-terminal amphipathic arm. Similarly, both caloleosin and steroleosin possess hydrophilic N and C-terminal arms and their own conserved hydrophobic core.

Oil Bodies

OBs generally range from 0.5-2.5 μm in diameter and consist of a TAG core surrounded by a phospholipid monolayer embedded with proteinaceous emulsifiers-predominantly oleosins (Tzen et al, 1993; Tzen, et al 1997). OBs consist of only 0.5-3.5% protein; of this 80-90% is oleosin with the remainder predominantly consisting of the calcium binding (caleosin) and sterol binding (steroleosin) proteins (Lin and Tzen, 2004). The ratio of oleosin to TAG within the plant cell influences the size and number of oil bodies within the cell (Sarmiento et al., 1997; Siloto et al., 2006).

While OBs are naturally produced predominantly in the seeds and pollen of many plants they are also found in some other organs (e.g., specific tubers).

Oleosins

Oleosins are comparatively small (15 to 24 kDa) proteins which allow the OBs to become tightly packed discrete organelles without coalescing as the cells desiccate or undergo freezing conditions (Leprince et al., 1998; Siloto et al., 2006; Slack et al., 1980; Shimada et al. 2008).

Oleosins have three functional domains consisting of an amphipathic N-terminal arm, a highly conserved central hydrophobic core (~72 residues) and a C-terminal amphipathic arm. The accepted topological model is one in which the N- and C-terminal amphipathic arms are located on the outside of the OBs and the central hydrophobic core is located inside the OB (Huang, 1992; Loer and Herman, 1993; Murphy 1993). The negatively charged residues of the N- and C-terminal amphipathic arms are exposed to the aqueous exterior whereas the positively charged residues are exposed to the OB interior and face the negatively charged lipids. Thus, the amphipathic arms with their outward facing negative charge are responsible for maintaining the OBs as individual entities via steric hinderance and electrostatic repulsion both in vivo and in isolated preparation (Tzen et al, 1992). The N-terminal amphipathic arm is highly variable and as such no specific secondary structure can describe all examples. In comparison the C-terminal arm contains a α-helical domain of 30-40 residues (Tzen et al, 2003). The central core is highly conserved and thought to be the longest hydrophobic region known to occur in nature; at the centre is a conserved 12 residue proline knot motif which includes three spaced proline residues (for reviews see Frandsen et al, 2001; Tzen et al, 2003). The secondary, tertiary and quaternary structure of the central domain is still unclear. Modelling, Fourier Transformation-Infra Red (FT-IR) and Circular Dichromism (CD) evidence exists for a number of different arrangements (for review see Roberts et al., 2008).

The properties of the major oleosins is relatively conserved between plants and is characterised by the following:

- 15-25 kDa protein corresponding to approximately 140-230 amino acid residues.
- The protein sequence can be divided almost equally along its length into 4 parts which correspond to a N-terminal hydrophilic region, two centre hydrophobic regions (joined by a proline knot or knob) and a C-terminal hydrophilic region.
- The topology of oleosin is attributed to its physical properties which includes a folded hydrophobic core flanked by hydrophilic domains. This arrangement confers an amphipathic nature to oleosin resulting in the hydrophobic domain being embedded in the phospholipid monolayer (Tzen et al., 1992) while the flanking hydrophilic domains are exposed to the aqueous environment of the cytoplasm.
- Typically oleosins do not contain cysteines Preferred oleosins for use in the invention are those which contain a central domain of approximately 70 non-polar amino acid residues (including a proline knot) uninterrupted by any charged residues, flanked by two hydrophilic arms.

Examples of oleosin sequences suitable to be modified for use in the invention, by the addition of at least one artificially introduced cysteine, are shown in Table 1 below. The sequences (both polynucleotide and polypeptide are provided in the Sequence Listing)

TABLE 1

| Sequences | Species | Protein accession no. | SEQ ID NO: | cDNA accession no. | SEQ ID NO: |
|---|---|---|---|---|---|
| Oleosin | S. indicum | AAG23840 | 1 | AF302907 | 13 |
| Oleosin | S. indicum | AAB58402 | 2 | U97700 | 14 |
| Oleosin | A. thaliana | CAA44225 | 3 | X62353 | 15 |
| Oleosin | A. thaliana | AAZ23930 | 4 | BT023738 | 16 |
| Oleosin | H. annuus | CAA44224.1 | 5 | X62352.1 | 17 |

TABLE 1-continued

| Sequences | Species | Protein accession no. | SEQ ID NO: | cDNA accession no. | SEQ ID NO: |
|---|---|---|---|---|---|
| Oleosin | B. napus | CAA57545.1 | 6 | X82020.1 | 18 |
| Oleosin | Z. mays | NP_001147032.1 | 7 | NM_001153560.1 | 19 |
| Oleosin | O. sativa | AAL40177.1 | 8 | AAL40177.1 | 20 |
| Oleosin | B. oleracea | AAD24547.1 | 9 | AF117126.1 | 21 |
| Oleosin | C. arabica | AAY14574.1 | 10 | AY928084.1 | 22 |
| Oleosin | B. oleraceae | CAA65272.1 | 11 | X96409 | 23 |
| Oleosin | S. indicum | AAD42942 | 12 | AF091840 | 24 |

Oleosin are well known to those skilled in the art. Further sequences from many different species can be readily identified by methods well-known to those skilled in the art. For example, further sequences can be easily identified by an NCBI Entrez Cross-Database Search (available at ncbi.nlm.nih.gov/sites/gquery) using oleosin as a search term.

Plant Lipids Biosynthesis

All plant cells produce fatty acids from actetyl-CoA by a common pathway localized in plastids. Although a portion of the newly synthesized acyl chains is then used for lipid biosynthesis within the plastid (the prokaryotic pathway), a major portion is exported into the cytosol for glycerolipid assembly at the endoplasmic reticulum (ER) or other sites (the eukaryotic pathway). In addition, some of the extraplastidial glycerolipids return to the plastid, which results in considerable intermixing between the plastid and ER lipid pools (Ohlrogge and Jaworski 1997).

The simplest description of the plastidial pathway of fatty acid biosynthesis consists of two enzyme systems: acetyl-CoA carboxylase (ACCase) and fatty acid synthase (FAS). ACCase catalyzes the formation of malonyl-CoA from acetyl-CoA, and FAS transfers the malonyl moiety to acyl carrier protein (ACP) and catalyzes the extension of the growing acyl chain with malonyl-ACP.

The initial fatty acid synthesis reaction is catalyzed by 3-ketoacyl-ACP III (KAS III) which results in the condensation of acetyl-CoA and malonyl-ACP. Subsequent condensations are catalyzed by KAS I and KAS II. Before a subsequent cycle of fatty acid synthesis begins, the 3-ketoacyl-ACP intermediate is reduced to the saturated acyl-ACP in the remaining FAS reactions, catalyzed sequentially by the 3-ketoacyl-ACP reductase, 3 hydroxyacyl-ACP dehydrase, and the enoyl-ACP reductase.

The final products of FAS are usually 16:0 and 18:0-ACP, and the final fatty acid composition of a plant cell is in large part determined by activities of several enzymes that use these acyl-ACPs at the termination phase of fatty acid synthesis. Stearoyl-ACP desatruase modifies the final product of FAS by insertion of a cis double bond at the 9 position of the C18:0-ACP. Reactions of fatty acid synthesis are terminated by hydrolysis or transfer of the acyl chain from the ACP. Hydrolysis is catalyzed by acyl-ACP thioesterases, of which there are two main types: one thioesterase relatively specific for 18:1-ACP and a second more specific for saturated acyl-ACPs. Fatty acids that have been released from ACPs by thioesterases leave the plastid and enter into the eukaryotic lipid pathway, where they are primarily esterified to glycerolipids on the ER. Acyl transferases in the plastid, in contrast to thioesterases, terminate fatty acid synthesis by transesterifying acyl moieties from ACP to glycerol, and they are an essential part of the prokaryotic lipid pathway leading to plastid glycerolipid assembly.

Triacylglycerol Biosynthesis

The only committed step in TAG biosynthesis is the last one, i.e. the addition of a third fatty acid to an existing diacylglycerol, thus generating TAG. In plants this step is predominantly (but not exclusively) performed by one of five (predominantly ER localised) TAG synthesizing enzymes including: acyl CoA: diacylglycerol acyltransferase (DGAT1); an unrelated acyl CoA: diacylglycerol acyl transferase (DGAT2); a soluble DGAT (DGAT3) which has less than 10% identity with DGAT1 or DGAT2 (Saha et al., 2006); phosphatidylcholine-sterol O-acyltransferase (PDAT); and a wax synthase (WSD1, Li et al., 2008). The DGAT1 and DGAT2 proteins are concoded by two distinct gene families, with DGAT1 containing approximately 500 amino acids and 10 predicted transmembrane domains and DGAT2 has only 320 amino acids and two transmembrane domains (Shockey et al., 2006).

The term "triacylglycerol synthesizing enzyme" or "TAG synthesizing enzyme" as used herein means an enzyme capable of catalysing the addition of a third fatty acid to an existing diacylglycerol, thus generating TAG. Preferred TAG synthesizing enzymes include but are not limited to: acyl CoA: diacylglycerol acyltransferase1 (DGAT1); diacylglycerol acyl transferase2 (DGAT2); phosphatidylcholine-sterol O-acyltransferase (PDAT) and cytosolic soluble form of DGAT (soluble DGAT or DGAT3).

Examples of these TAG synthesizing enzymes, suitable for use in the methods and compositions of the invention, from members of several plant species are provided in Table 2 below. The sequences (both polynucleotide and polypeptide are provided in the Sequence Listing)

TABLE 2

| TAG synthesising enzyme | Species | Protein accession no. | SEQ ID NO: | cDNA accession no. | SEQ ID NO: |
|---|---|---|---|---|---|
| DGAT1 | A. thaliana | NP_179535 | 25 | NM_127503 | 33 |
| DGAT1 | T. majus | AAM03340 | 26 | AY084052 | 34 |
| DGAT1 | Z. mays | ABV91586 | 27 | EU039830 | 35 |
| DGAT2 | A. thaliana | NP_566952 | 28 | NM_115011 | 36 |
| DGAT2 | B. napus | AC090187 | 29 | FJ858270 | 37 |
| DGAT3 (soluble DGAT) | A. hypogaea | AAX62735 | 30 | AY875644 | 38 |

TABLE 2-continued

| TAG synthesising enzyme | Species | Protein accession no. | SEQ ID NO: | cDNA accession no. | SEQ ID NO: |
|---|---|---|---|---|---|
| PDAT | A. thaliana | NP_196868 | 31 | NM_121367 | 39 |
| PDAT | R. communis | XP_002521350 | 32 | XM_002521304 | 40 |

The inventions also contemplates use of modified TAG synthesizing enzymes, that are modified (for example in their sequence by substitutions, insertions or additions and the like) to alter their specificity and or activity.

Modified Oleosins Engineered to Include Artificially Introduced Cysteines

The modified oleosins for use in the methods of the invention, are modified to contain at least one artificially introduced cysteine residue. Preferably the engineered oleosins contain at least two cysteines.

Various methods well-known to those skilled in the art may be used in production of the modified oleosins with artificially introduced cysteines.

Such methods include site directed mutagenesis (U.S. Pat. No. 6,448,048) in which the polynucleotide encoding an oleosin is modified to introduce a cysteine into the encoded oleosin protein.

Alternatively, the polynucleotide encoding the modified oleosins, may be synthesised in its entirety.

Further methodology for producing modified oleosins and for use in the methods of the invention are described in WO/2011/053169, U.S. Pat. No. 8,987,551, and WO/2013/022353, and are provided in the Examples section of the present application.

The introduced cysteine may be an additional amino acid (i.e. an insertion) or may replace an existing amino acid (i.e. a replacement). Preferably the introduced cysteine replaces an existing amino acid. In a preferred embodiment the replaced amino acid is a charged residue. Preferably the charged residue is predicted to be in the hydrophilic domains and therefore likely to be located on the surface of the oil body.

The hydrophilic, and hydrophobic regions/arms of the oleosin can be easily identified by those skilled in the art using standard methodology (for example: Kyte and Doolitle (1982).

The modified oleosins for use in the methods of the invention are preferably range in molecular weight from 5 to 50 kDa, more preferably, 10 to 40 kDa, more preferably 15 to 25 kDa.

The modified oleosins for use in the methods of the invention are preferably in the size range 100 to 300 amino acids, more preferably 110 to 260 amino acids, more preferably 120 to 250 amino acids, more preferably 130 to 240 amino acids, more preferably 140 to 230 amino acids.

Preferably the modified oleosins comprise an N-terminal hydrophilic region, two centre hydrophobic regions (joined by a proline knot or knob) and a C-terminal hydrophilic region.

Preferably the modified oleosins can be divided almost equally their length into four parts which correspond to the N-terminal hydrophilic region (or arm), the two centre hydrophobic regions (joined by a proline knot or knob) and a C-terminal hydrophilic region (or arm).

Preferably the topology of modified oleosin is attributed to its physical properties which include a folded hydrophobic core flanked by hydrophilic domains.

Preferably the modified oleosins can be formed into oil bodies when combined with triacylglycerol (TAG) and phospholipid.

Preferably topology confers an amphipathic nature to modified oleosin resulting in the hydrophobic domain being embedded in the phospholipid monolayer of the oil body while the flanking hydrophilic domains are exposed to the aqueous environment outside the oil body, such as in the cytoplasm.

Preferably the modified oleosin includes at least one artificially introduced cysteine, wherein the cysteine is introduced into at least one of:

a) in the N-terminal hydrophilic region of the oleosin, and b) in the C-terminal hydrophilic region of the oleosin.

In one embodiment the modified oleosin for use in the method of the invention, comprises a sequence with at least 70% identity to the hydrophobic domain of any of the oleosin protein sequences referred to in Table 1 above.

In one embodiment the modified oleosin for use in the method of the invention, comprises a sequence with at least 70% identity to the hydrophobic domain of any of the protein sequences of SEQ ID NO: 1-12.

In one embodiment the modified oleosin for use in the method of the invention, comprises a sequence with at least 70% identity to of any of the oleosin protein sequences referred to in Table 1 above.

In one embodiment the modified oleosin for use in the method of the invention, comprises a sequence with at least 70% identity to any of the protein sequences of SEQ ID NO: 1-12.

In further embodiment the modified oleosin is essentially the same as any of the oleosins referred to in Table 1 above, apart from the additional artificially introduced cysteine or cysteines.

In a further embodiment the modified oleosin of the invention or used in the method of the invention, comprises a sequence with at least 70% identity to the hydrophobic domain of the oleosin sequence of SEQ ID NO: 12.

In a further embodiment the modified oleosin of the invention or used in the method of the invention, comprises a sequence with at least 70% identity to the oleosin sequence of SEQ ID NO: 12.

In further embodiment the modified oleosin has the same amino acid sequence as that of SEQ ID NO: 12, apart from the additional artificially introduced cysteine or cysteines.

In a further embodiment the modified oleosin of the invention or used in the method of the invention, comprises a sequence with at least 70% identity to the hydrophobic domain of the sequence of SEQ ID NO: 49.

In a further embodiment the modified oleosin of the invention or used in the method of the invention, comprises a sequence with at least 70% identity to the sequence of SEQ ID NO: 49.

In further embodiment the modified oleosin has the amino acid sequence of SEQ ID NO: 49.

Overview of Photosynthesis

The overall process whereby algae and plants use light to synthesize organic compounds is called photosynthesis.

Photosynthesis encompasses a complex series of reactions that involve light absorption, production of stored energy and reducing power (the Light Reactions). It also includes a multistep enzymatic pathway that uses these to convert $CO_2$ and water into carbohydrates (the Calvin cycle). In plants the biophysical and biochemical reactions of photosynthesis occur within a single chloroplast (C3 photosynthesis) but can also be separated into chloroplasts of differing cell types (C4 photosynthesis).

Carbon fixation is a redox reaction, photosynthesis provides both the energy to drive this process as well as the electrons required to convert $CO_2$ to carbohydrate. These two processes take place through a different sequence of chemical reactions and in different cellular compartments. In the first stage, light is used to generate the energy storage molecules ATP and NADPH. The thylakoid membranes contain the multiprotein photosynthetic complexes Photosystems I and II (PSI and PSII) which include the reaction centres responsible for converting light energy into chemical bond energy (via an electron transfer chain). The photosynthetic electron transfer chain moves electrons from water into the thylakoid lumen to soluble redox-active compounds in the stroma. A byproduct of this process (Hill Reaction) is oxygen.

The second part of the photosynthetic cycle is the fixation of $CO_2$ into sugars (Calvin Cycle); this occurs in the stroma and uses the ATP and NADPH generated from the light reaction.

Rubisco

Ribulose biphosphate carboxlase (Rubisco) is the key enzyme responsible for photosynthetic carbon assimilation in catalysing the reaction of $CO_2$ with ribulose 1,5biophosphate (RuBP) to form two molecules of D-phosphoglyceric acid (PGA) (Parry et al, 2003). Since Rubisco works very slowly, catalyzing only the reaction of a few molecules per second, large quantities of the enzyme are required; consequently Rubisco makes up 30-50% of the soluble protein in leaves (Bock and Khan, 2004). Genetic modification to increase the catalytic rate of Rubisco would have great importance. Parry et al, (2003) reviewed the progress to date, concluding that there are still many technical barriers to overcome and to date all engineering attempts have failed to produce a better Rubisco.

In the presence of $O_2$, Rubisco also performs an oxygenase reaction, which initiates photorespiratory or C2 cycle (FIG. 21) by the formation of phosphoglycolate and 3-phosphoglycerate (3-PGA). The recycling of phosphoglycolate results in an indirect loss of fixed nitrogen and $CO_2$ from the cell which need to be recovered. Genetic modification to increase the specificity of Rubisco for $CO_2$ relative to $O_2$ and to increase the catalytic rate of Rubisco in crop plants would have great agronomic importance. Parry et al, (2003) reviewed the progress to date, concluding that there are still many technical barriers to overcome and to date all engineering attempts have thus far failed to produce a better Rubisco (Peterhansel et al. 2008). Furthermore, it has been demonstrated that photorespiration is required in C3 plants to protect plants from photoxidation under high light intensity (Kozaki and Takeba 1996).

C3 and C2 Cycles

In C3 plants under atmospheric conditions, approximately three out of four Rubisco enzymic reactions in C3 plants fix $CO_2$ (carboxylase reaction, C3 cycle, FIG. 20). The fourth reaction; however, catalyses an oxygenase reaction (FIG. 3) which indirectly results in a net loss of fixed $CO_2$ and $NH_4^+$ and the production of a number of intermediate metabolites via the C2 (photorespiration) cycle (FIG. 22). Ultimately, this incurs a substantial metabolic cost through the refixing of $CO_2$ and $NH_4^+$ as well as the recycling of the intermediates. Furthermore, when C3 plants experience water stress and/or elevated temperatures the portion of oxygenase to carboxylase reactions rises courtesy of the elevated $O_2$ within the leaf. Nonetheless it has been demonstrated that photorespiration is required in C3 plants to protect plants from photoxidation under high light intensity (Kozaki and Takeba, 1996) and appears to provide much of the reducing power required for $NO_3^-$ assimilation in the leaf (Rachmilevitch et al., 2004).

Organisms capable of oxygenic photosynthesis began their evolution in a vastly different atmosphere (Giordano et al. 2005). One of the most dramatic changes has been the rise in the $O_2:CO_2$ ratio, where the competition between these two gasses for the active site of Rubisco has become progressively restrictive to the rate of carbon fixation. However, some have suggested that the gradual change appears to have provided a lack of evolutionary pressure for Rubisco with a high affinity for $CO_2$ or a Rubisco without oxygenase activity. Indeed, plant Rubiscos are considered more evolutionarily recent than algal Rubiscos and as such they are much more selective for $CO_2$ over $O_2$. Genetic modifications to increase the specificity of Rubisco for $CO_2$ relative to $O_2$ have failed (Parry, Andralojc et al. 2003).

A significant role of the C2 oxidative photosynthetic carbon cycle or photorespiratory pathway is the recycling of 2-phosphoglycolate (2PG) produced by the oxygenase activity of Rubisco (Tolbert 1997). 2PG is toxic to the cell; hence it is rapidly dephosphorylated (via phosphoglycolate phosphatase, PGP) to glycolate (Tolbert et al, 1983). Furthermore, it has been demonstrated that photorespiration is required in C3 plants to protect plants from photoxidation under high light intensity (Kozaki and Takeba 1996).

The enzymes that oxidise glycolate to glycoxylate in the photorespiratory pathway are characterised into two structurally different groups. In higher plants, the peroxisome-localized, FMN-containing glycolate oxygenase, GOX (EC 1.1.3.15) catalyzes glycolate oxidation using molecular oxygen as the terminal electron acceptor and has a stereopsecificity for L-lactate as an alternative substrate. In contrast, glycolate dehydrogenase, GDH (EC 1.1.99.14) has been characterized only by its non-oxygen-requiring enzymatic reaction and its stereospecificity for D-lactate as an alternative substrate. In most algae, glycolate is oxidised in the mitochondria using a monomeric GDH which is dependent on organic co-factors. The capacity of the reaction seems to be limited by the organic co-factors and consequently many algae excrete glycolate into the medium under photorespiratory growth conditions (Bari et al, 2009; Colman et al, 1974). GDH in C. reinhardtii is a mitochondrially located, low-$CO_2$-responsive gene (Nakamura et al, 2005). Other GDH homologs include the so-called glycolate oxidase (GOX) of E. coli and other bacteria. In E. coli, the GOX complex is composed of three functional subunits, GlcD, GlcE, and GlcF of which GlcD and GlcE share a highly conserved amino acid sequence that includes a putative flavin-binding region. In the GlcF protein, two highly conserved CxxCxxCxxxCP motifs have been recognized, which represent the typical 2×[4Fe-4S] iron-sulfur clusters, as found also in the GlpC subunit of anaerobic G3P dehydrogenase, and ubiquinone oxidoreductase homologs from prokaryotes and eukaryotes (Nakamura et al, 2005).

C4 Cycle

Not all plants use Rubisco to generate 3-PGA as the first stable photosynthetic intermediate. Maize, sugarcane, numerous tropical grasses and some dicotyledonous plants (e.g., *Amaranthus*) initially use phosphoenolpyruvate to fix carbon, forming 4-carbon organic acids (C4 plants). C4 plants avoid the C2 cycle through modifications to their architecture involving two different types of chloroplast containing cells, mesophyll cells and bundle sheath cells which isolates Rubisco in a relatively rich $CO_2$ environment thereby increasing the proportion of carboxylase reactions. This enables these plants to initially use phosphoenolpyruvate to fix carbon, forming 4-carbon organic acids (hence C4 plants). Thus the C4 metabolism involves fixing inorganic carbon in one cell type (mesophyll), transporting it to a cell type partially shielded from atmospheric oxygen (bundle sheath), and releasing the inorganic carbon near Rubsico in this oxygen deprived environment.

The leaves of C4 plants demonstrate an unusual anatomy involving two different types of chloroplast containing cells, mesophyll cells and bundle sheath cells. Where the mesophyll cells surround the bundle sheath cells which in turn surround the vascular tissue; the chloroplasts of the mesophyll cells contain all the transmembrane complexes required for the light reactions of photosynthesis but little or no Rubisco while the bundle sheath cell chloroplasts lack stacked thylakoids and contain little PSII. C4 plants concentrate $CO_2$ in the bundle sheath cells effectively suppressing Rubiscos oxygenase activity and eliminating photorespiration.

Oxaloacetate is generated from $HCO_3^-$ and phosphoenolpyruvate (PEP) by phosphoenolpyruvate carboxylase (PEPC) in the cytosol of mesophyll cells. The $HCO_3^-$ ion is used since its aqueous equilibrium is favoured over gaseous $CO_2$. Moreover, PEP carboxylase cannot fix oxygen, which has a 3D structure similar to that of $CO_2$ but not $HCO_3^-$. Depending on the $C_4$ plant, oxaloacetate is oxidised to malate or condensed with glutamate to form aspartate and a Keto glutarate. The malate and aspartate are transported into the bundle sheath cells and decarboxylated releasing $CO_2$ which is then available for Rubisco and incorporation into the Calvin cycle.

The agronomic downside of this evolved modification is an increase in leaf fibre resulting in a comparatively poor digestibility of leaves from C4 plants (e.g., maize, sugarcane, numerous tropical grasses and some dicotyledonous plants such as *Amaranthus*). To date, the modification of a $C_3$ plant to emulate the whole C4 process is beyond current biotechnology. Furthermore, attempts to engineer Rubisco to either obliterate oxygenase activity or to decrease the affinity for $O_2$ have failed (for review see Peterhansel et al. 2008).

Interaction with of Nitrate Assimilation

Reducing photorespiration through manipulation of atmospheric $CO_2$ over long periods has led to the unexpected reduction of nitrate assimilation in C3 plants (Rachmilevitch et al., 2004). There are a number of possible explanations including the lowering of available reducing power, reduced ferredoxin and NADH, the former is required for nitrate reductase and glytamate synthetase while latter is required for the reduction of $NO_3^-$ (where NADH is produced during the glycine decarboxylase photorespiratory step in the mitochondria). In addition, transport of $NO_2^-$ from the cytosol into the chloroplast involves the net diffusion of $HNO_2$ or co-transport of protons and $NO_2^-$ across the chloroplast membrane. This requires the stroma to be more alkaline than the cytosol but the pH gradient is somewhat dissipated by elevated $CO_2$ levels. Rachmilevitch et al (2004) concluded that nitrate reductase activity by itself was not limiting to nitrate assimilation under lowered photorespiration. They also concluded that it was the form of nitrogen available to the plant that determined the degree to which elevated $CO_2$ levels would result in an increase in net primary production, i.e., where $NH_4^+$ is the dominant nitrogen form. This would suggest that in the absence of changing agronomic fertilisation practices, the legumes stand to benefit most by the reduction of photorespiration since the rhizobial/legume symbiosis results in the fixation of atmospheric nitrogen in the form of $NH_4^+$ rather than $NO_3^-$.

Previous Efforts to Engineering Higher Chloroplast $CO_2$ Levels and Reduced Photorespiration in C3 Plants A number of investigations have been performed in higher plants to address the limitations of photorespiration. Essentially only one of these appears to have potential applications in the adaptation to higher plants. A recent photorespiratory bypass which increased the efficiency of glycolate recycling was successfully engineered into *Arabidopsis* and resulted in a 30% increase in leaf biomass (Kebeish et al., 2007). Kebeish et al (2007) transformed *Arabidopsis* to express three genes from *E. coli*: glycolate dehydrogenase (GDH), glyoxylate carboxyligase (GCL), tartronic semialdehyde reductase (TSR) in their chloroplasts (FIG. 23). Combined, these genes recycled glycolate to glycerate in the chloroplast, in other words without the involvement of the peroxisome or mitochondrion. GDH from *E. coli* is a heterotrimer, consisting of glcD, glcE and glcF resulting in plants with a 30% increase in leaf biomass by the end of the growth period (FIG. 24). This pathway included a chloroplast $CO_2$ release step which further reduced RubisCO's oxygenase activity in vivo. Moreover, energy and reducing equivalents were thought to be saved by the bypass as it no longer results in the release of ammonium and the energy from glycolate oxidation is saved in reducing equivalents and not consumed during the formation of $H_2O_2$ (Maurino and Peterhansel 2010). Peterhansel (2011) concluded that to truly transform a C3 plant into a C4 plant will require the efficient transfer of multiple genes.

Tissue/Organ Specific and Preferred Promoters

A tissue/organ preferred promoter is a promoter that drives expression of an operably linked polynucleotide in a particular tissue/organ at a higher level than in other tissues/organs. A tissue specific promoter is a promoter that drives expression of an operably linked polynucleotide specifically in a particular tissue/organ. Even with tissue/organ specific promoters, there is usually a small amount of expression in at least one other tissue. A tissue specific promoter is by definition also a tissue preferred promoter.

Vegetative Tissues

Vegetative tissue include, shoots, leaves, roots, stems. A preferred vegetative tissue is a leaf.

Vegetative Tissue Specific Promoters

An example of a vegetative specific promoter is found in U.S. Pat. Nos. 6,229,067; and 7,629,454; and 7,153,953; and 6,228,643.

Pollen Specific Promoters

An example of a pollen specific promoter is found in U.S. Pat. Nos. 7,141,424; and 5,545,546; and 5,412,085; and 5,086,169; and 7,667,097.

Seed Specific Promoters

An example of a seed specific promoter is found in U.S. Pat. Nos. 6,342,657; and 7,081,565; and 7,405,345; and 7,642,346; and 7,371,928.

Fruit Specific Promoters

An example of a fruit specific promoter is found in U.S. Pat. Nos. 5,536,653; and 6,127,179; and 5,608,150; and 4,943,674.

Non-Photosynthetic Tissue Preferred Promoters

Non-photosynthetic tissue preferred promoters include those preferentially expressed in non-photosynthetic tissues/organs of the plant.

Non-photosynthetic tissue preferred promoters may also include light repressed promoters.

Light Repressed Promoters

An example of a light repressed promoter is found in U.S. Pat. No. 5,639,952 and in U.S. Pat. No. 5,656,496.

Root Specific Promoters

An example of a root specific promoter is found in U.S. Pat. No. 5,837,848; and US 2004/0067506 and US 2001/0047525.

Tuber Specific Promoters

An example of a tuber specific promoter is found in U.S. Pat. No. 6,184,443.

Bulb Specific Promoters

An example of a bulb specific promoter is found in Smeets et al., (1997) Plant Physiol. 113:765-771.

Rhizome Preferred Promoters

An example of a rhizome preferred promoter is found Seong Jang et al., (2006) Plant Physiol. 142:1148-1159.

Endosperm Specific Promoters

An example of an endosperm specific promoter is found in U.S. Pat. No. 7,745,697.

Corm Promoters

An example of a promoter capable of driving expression in a corm is found in Schenk et al., (2001) Plant Molecular Biology, 47:399-412.

Photosythetic Tissue Preferred Promoters

Photosythetic tissue preferred promoters include those that are preferrentially expressed in photosynthetic tissues of the plants. Photosynthetic tissues of the plant include leaves, stems, shoots and above ground parts of the plant. Photosythetic tissue preferred promoters include light regulated promoters.

Light Regulated Promoters

Numerous light regulated promoters are known to those skilled in the art and include for example chlorophyll a/b (Cab) binding protein promoters and Rubisco Small Subunit (SSU) promoters. An example of a light regulated promoter is found in U.S. Pat. No. 5,750,385. Light regulated in this context means light inducible or light induced.

Relative Terms

The relative terms, such as increased and reduced as used herein with respect to plants, are relative to a control plant. Suitable control plants include non-transformed or wild-type versions of plant of the same variety and/or species as the transformed plant used in the method of the invention. Suitable control plants also include plants of the same variety and/or species as the transformed plant that are transformed with a control construct. Suitable control constructs include empty vector constructs, known to those skilled in the art. Suitable control plants also include plants that have not been transformed with a polynucleotide encoding a modified oleosin including at least one artificially introduced cysteine. Suitable control plants also include plants that do not express a modified oleosin including at least one artificially introduced cysteine.

The term "biomass" refers to the size and/or mass and/or number of vegetative organs of the plant at a particular age or developmental stage. Thus a plant with increased biomass has increased size and/or mass and/or number of vegetative organs than a suitable control plant of the same age or at an equivalent developmental stage. Increased biomass may also involve an increase in rate of growth and/or rate of formation of vegetative organs during some or all periods of the life cycle of a plant relative to a suitable control. Thus increased biomass may result in an advance in the time taken for such a plant to reach a certain developmental stage.

The terms "seed yield", "fruit yield" and "organ yield" refer to the size and/or mass and/or number of seed, fruit or organs produced by a plant. Thus a plant with increased seed, fruit or organ yield has increased size and/or mass and/or number of seeds, fruit or organs respectively, relative to a control plant at the same age or an equivalent developmental stage.

The terms "increased drought tolerance" and "increased water use efficiency" or grammatical equivalents thereof, is intended to describe a plant which performs more favourably in any aspect of growth and development under, or after, sub-optimal hydration conditions than do control plants in the same conditions.

The term "increased high temperature tolerance" or grammatical equivalents thereof, is intended to describe plant which performs more favourably in any aspect of growth and development under, or after, sub-optimal elevated temperature conditions than do control plants in the same conditions.

The term "increased high oxygen concentration tolerance" or grammatical equivalents thereof is intended to describe plant which performs more favourably in any aspect of growth and development under, or after, sub-optimal elevated oxygen concentrations than do control plants in the same conditions.

The term "increased nitrogen use efficiency" or grammatical equivalents thereof is intended to describe plant which performs more favourably in any aspect of growth and development under, or after, sub-optimal reduced nitrogen conditions than do control plants in the same conditions.

The term "increased rate of $CO_2$ assimilation" or grammatical equivalents thereof is intended to describe plant which assimilates more $CO_2$ under any given conditions than does a control plant in the same conditions.

The term "increased rate of photosynthesis" or grammatical equivalents thereof is intended to describe plant which accumulates more photosynthetic under any given conditions than does a control plant in the same conditions.

The term "increased growth rate" or grammatical equivalents thereof is intended to describe plant which grows more quickly under any given conditions than does a control plant in the same conditions.

The term "delayed flowering" or grammatical equivalents thereof is intended to describe plant which flowers later under any given conditions than does a control plant in the same conditions.

The term "increased chloroplast $CO_2$ concentration" or grammatical equivalents thereof is intended to describe a plant has a higher concentration of $CO_2$ in the chloroplast under any given conditions than does a control plant in the same conditions.

The term "decreased rate of photorespiration" or grammatical equivalents thereof, is intended to describe a plant which shows less photorespiration under any given conditions than does a control plant in the same conditions.

The term "decreased loss of fixed carbon" or grammatical equivalents thereof, is intended to describe plant which loses less fixed carbon under any given conditions than does a control plant in the same conditions.

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, IRNA, siRNA, miRNA, RNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of contiguous nucleotides that is capable of specific hybridization to a target of interest, e.g., a sequence that is at least 15 nucleotides in length. The fragments of the invention comprise 15 nucleotides, preferably at least 16 nucleotides, more preferably at least 17 nucleotides, more preferably at least 18 nucleotides, more preferably at least 19 nucleotides, more preferably at least 20 nucleotides, more preferably at least 21 nucleotides, more preferably at least 22 nucleotides, more preferably at least 23 nucleotides, more preferably at least 24 nucleotides, more preferably at least 25 nucleotides, more preferably at least 26 nucleotides, more preferably at least 27 nucleotides, more preferably at least 28 nucleotides, more preferably at least 29 nucleotides, more preferably at least 30 nucleotides, more preferably at least 31 nucleotides, more preferably at least 32 nucleotides, more preferably at least 33 nucleotides, more preferably at least 34 nucleotides, more preferably at least 35 nucleotides, more preferably at least 36 nucleotides, more preferably at least 37 nucleotides, more preferably at least 38 nucleotides, more preferably at least 39 nucleotides, more preferably at least 40 nucleotides, more preferably at least 41 nucleotides, more preferably at least 42 nucleotides, more preferably at least 43 nucleotides, more preferably at least 44 nucleotides, more preferably at least 45 nucleotides, more preferably at least 46 nucleotides, more preferably at least 47 nucleotides, more preferably at least 48 nucleotides, more preferably at least 49 nucleotides, more preferably at least 50 nucleotides, more preferably at least 51 nucleotides, more preferably at least 52 nucleotides, more preferably at least 53 nucleotides, more preferably at least 54 nucleotides, more preferably at least 55 nucleotides, more preferably at least 56 nucleotides, more preferably at least 57 nucleotides, more preferably at least 58 nucleotides, more preferably at least 59 nucleotides, more preferably at least 60 nucleotides, more preferably at least 61 nucleotides, more preferably at least 62 nucleotides, more preferably at least 63 nucleotides, more preferably at least 64 nucleotides, more preferably at least 65 nucleotides, more preferably at least 66 nucleotides, more preferably at least 67 nucleotides, more preferably at least 68 nucleotides, more preferably at least 69 nucleotides, more preferably at least 70 nucleotides, more preferably at least 71 nucleotides, more preferably at least 72 nucleotides, more preferably at least 73 nucleotides, more preferably at least 74 nucleotides, more preferably at least 75 nucleotides, more preferably at least 76 nucleotides, more preferably at least 77 nucleotides, more preferably at least 78 nucleotides, more preferably at least 79 nucleotides, more preferably at least 80 nucleotides, more preferably at least 81 nucleotides, more preferably at least 82 nucleotides, more preferably at least 83 nucleotides, more preferably at least 84 nucleotides, more preferably at least 85 nucleotides, more preferably at least 86 nucleotides, more preferably at least 87 nucleotides, more preferably at least 88 nucleotides, more preferably at least 89 nucleotides, more preferably at least 90 nucleotides, more preferably at least 91 nucleotides, more preferably at least 92 nucleotides, more preferably at least 93 nucleotides, more preferably at least 94 nucleotides, more preferably at least 95 nucleotides, more preferably at least 96 nucleotides, more preferably at least 97 nucleotides, more preferably at least 98 nucleotides, more preferably at least 99 nucleotides, more preferably at least 100 nucleotides, more preferably at least 150 nucleotides, more preferably at least 200 nucleotides, more preferably at least 250 nucleotides, more preferably at least 300 nucleotides, more preferably at least 350 nucleotides, more preferably at least 400 nucleotides, more preferably at least 450 nucleotides and most preferably at least 500 nucleotides of contiguous nucleotides of a polynucleotide disclosed. A fragment of a polynucleotide sequence can be used in antisense, RNA interference (RNAi), gene silencing, triple helix or ribozyme technology, or as a primer, a probe, included in a microarray, or used in polynucleotide-based selection methods of the invention.

The term "primer" refers to a short polynucleotide, usually having a free 3'OH group, that is hybridized to a template and used for priming polymerization of a polynucleotide complementary to the target.

The term "probe" refers to a short polynucleotide that is used to detect a polynucleotide sequence that is complementary to the probe, in a hybridization-based assay. The probe may consist of a "fragment" of a polynucleotide as defined herein.

Polypeptides and Fragments

The term "polypeptide", as used herein, encompasses amino acid chains of any length but preferably at least 5 amino acids, including full-length proteins, in which amino acid residues are linked by covalent peptide bonds. Polypeptides of the present invention, or used in the methods of the invention, may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the polypeptide that performs a function that is required for the biological activity and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above enzymatic activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polynucleotides or polypeptides of the invention being derived from a particular genera or species, means that the polynucleotide or polypeptide has the same sequence as a polynucleotide or polypeptide found naturally in that genera or species. The polynucleotide or polypeptide, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polypeptides and polypeptides possess biological activities that are the same or similar to those of the inventive polypeptides or polypeptides. The term "variant" with reference to polypeptides and polypeptides encompasses all forms of polypeptides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequence of the present invention. Identity is found over a comparison window of at least 20 nucleotide positions, preferably at least 50 nucleotide positions, more preferably at least 100 nucleotide positions, and most preferably over the entire length of a polynucleotide of the invention.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI (ncbi.nih.gov/blast/). The default parameters of bl2seq are utilized except that filtering of low complexity parts should be turned off.

The identity of polynucleotide sequences may be examined using the following unix command line parameters:

bl2seq –i nucleotideseq1 –j nucleotideseq2 –F F –p blastn

The parameter –F F turns off filtering of low complexity sections. The parameter –p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from hgmp.mrc.ac.uk/Software/EMBOSS/. The European Bioinformatics Institute server also provides the facility to perform EMBOSS-needle global alignments between two sequences on line at ebi.ac.uk/emboss/align/.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

A preferred method for calculating polynucleotide % sequence identity is based on aligning sequences to be compared using Clustal X (Jeanmougin et al., 1998, Trends Biochem. Sci. 23, 403-5.)

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (ncbi.nih.gov/blast/).

The similarity of polynucleotide sequences may be examined using the following unix command line parameters:

bl2seq –i nucleotideseq1 –j nucleotideseq2 –F F –p tblastx

The parameter –F F turns off filtering of low complexity sections. The parameter –p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10-6$ more preferably less than $1\times10-9$, more preferably less than $1\times10-12$, more preferably less than $1\times10-15$, more preferably less than $1\times10-18$, more preferably less than $1\times10-21$, more preferably less than $1\times10-30$, more preferably less than $1\times10-40$, more preferably less than $1\times10-50$, more preferably less than $1\times10-60$, more preferably less than $1\times10-70$, more preferably less than $1\times10-80$, more preferably less than $1\times10-90$ and most preferably less than $1\times10-100$ when compared with any one of the specifically identified sequences.

Alternatively, variant polynucleotides of the present invention, or used in the methods of the invention, hybridize to the specified polynucleotide sequences, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing,). Tm for polynucleotide molecules greater than about 100 bases can be calculated by the formula Tm=81.5+0.41% (G+C-log(Na+). (Sambrook et al., Eds, 1987, Molecular Cloning, A Laboratory Manual, 2nd Ed. Cold Spring Harbor Press; Bolton and Mccarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)® C.

With respect to the DNA mimics known as peptide nucleic acids (PNAs) (Nielsen et al., Science. 1991 Dec. 6; 254 (5037): 1497-500) Tm values are higher than those for DNA-DNA or DNA-RNA hybrids, and can be calculated using the formula described in Giesen et al., Nucleic Acids Res. 1998 Nov. 1; 26 (21): 5004-6. Exemplary stringent hybridization conditions for a DNA-PNA hybrid having a length less than 100 bases are 5 to 10° C. below the Tm.

Variant polynucleotides of the present invention, or used in the methods of the invention, also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from NCBI (ncbi.nih.gov/blast/) via the tblastx algorithm as previously described.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from NCBI (ncbi.nih.gov/blast/). The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at ebi-.ac.uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

A preferred method for calculating polypeptide % sequence identity is based on aligning sequences to be compared using Clustal X (Jeanmougin et al., 1998, Trends Biochem. Sci. 23, 403-5.)

Polypeptide variants of the present invention, or used in the methods of the invention, also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (ncbi.nih.gov/blast/). The similarity of polypeptide sequences may be examined using the following unix command line parameters:

bl2seq -i peptideseq1 -j peptideseq2 -F F -p blastp

Variant polypeptide sequences preferably exhibit an E value of less than 1×10-6 more preferably less than 1×10-9, more preferably less than 1×10-12, more preferably less than 1×10-15, more preferably less than 1×10-18, more preferably less than 1×10-21, more preferably less than 1×10-30, more preferably less than 1×10-40, more preferably less than 1×10-50, more preferably less than 1×10-60, more preferably less than 1×10-70, more preferably less than 1×10-80, more preferably less than 1×10-90 and most preferably 1×10-100 when compared with any one of the specifically identified sequences.

The parameter −F F turns off filtering of low complexity sections. The parameter −p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

Constructs, Vectors and Components Thereof

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as *E. coli*.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:

a) a promoter functional in the host cell into which the construct will be transformed,
b) the polynucleotide to be expressed, and
c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence may, in some cases, identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination, mRNA stability, and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors. Introns within coding sequences can also regulate transcription and influence post-transcriptional processing (including splicing, capping and polyadenylation).

A promoter may be homologous with respect to the polynucleotide to be expressed. This means that the promoter and polynucleotide are found operably linked in nature.

Alternatively the promoter may be heterologous with respect to the polynucleotide to be expressed. This means that the promoter and the polynucleotide are not found operably linked in nature.

A "transgene" is a polynucleotide that is taken from one organism and introduced into a different organism by transformation. The transgene may be derived from the same species or from a different species as the species of the organism into which the transgene is introduced.

An "inverted repeat" is a sequence that is repeated, where the second half of the repeat is in the complementary strand, e.g.,

```
(5')GATCTA.......TAGATC(3')

(3')CTAGAT.......ATCTAG(5')
```

Read-through transcription will produce a transcript that undergoes complementary base-pairing to form a hairpin structure provided that there is a 3-5 bp spacer between the repeated regions.

Host Cells

Host cells may be derived from, for example, bacterial, fungal, yeast, insect, mammalian, algal or plant organisms. Host cells may also be synthetic cells. Preferred host cells are eukaryotic cells. A particularly preferred host cell is a plant cell.

A "transgenic plant" refers to a plant which contains new genetic material as a result of genetic manipulation or transformation. The new genetic material may be derived from a plant of the same species as the resulting transgenic plant or from a different species.

Methods for Isolating or Producing Polynucleotides

The polynucleotide molecules of the invention can be isolated by using a variety of techniques known to those of ordinary skill in the art. By way of example, such polypeptides can be isolated through use of the polymerase chain reaction (PCR) described in Mullis et al., Eds. 1994 The Polymerase Chain Reaction, Birkhauser, incorporated herein by reference. The polypeptides of the invention can be amplified using primers, as defined herein, derived from the polynucleotide sequences of the invention.

Further methods for isolating polynucleotides of the invention include use of all, or portions of, the polypeptides having the sequence set forth herein as hybridization probes. The technique of hybridizing labelled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5.0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full length polynucleotide sequence. Such methods include PCR-based methods, 5'RACE (Frohman M A, 1993, Methods Enzymol. 218:340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, Nucleic Acids Res 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species.

Variants (including orthologues) may be identified by the methods described.

Methods for Identifying Variants
Physical Methods

Variant polypeptides may be identified using PCR-based methods (Mullis et al., Eds. 1994 The Polymerase Chain Reaction, Birkhauser). Typically, the polynucleotide sequence of a primer, useful to amplify variants of polynucleotide molecules of the invention by PCR, may be based on a sequence encoding a conserved region of the corresponding amino acid sequence.

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Polypeptide variants may also be identified by physical methods, for example by screening expression libraries using antibodies raised against polypeptides of the invention (Sambrook et al., Molecular Cloning: A Laboratory Manual, 2nd Ed. Cold Spring Harbor Press, 1987) or by identifying polypeptides from natural sources with the aid of such antibodies.

Computer Based Methods

The variant sequences of the invention, including both polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29:1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from (ncbi.nih.gov/blast/) or from the National Center for Biotechnology Information (NCBI), National Library of Medicine, Building 38A, Room 8N805, Bethesda, MD 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25:3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680, igbmc.u-strasbg.fr/BioInfo/ClustalW/Top.html) or T-COFFEE (Cedric Notredame, Desmond G. Higgins, Jaap Heringa, T-Coffee: A novel method for fast and accurate multiple sequence alignment, J. Mol. Biol. (2000) 302:205-217)) or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (expasy.org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Methods for Isolating Polypeptides

The polypeptides of the invention, or used in the methods of the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco California, or automated synthesis, for example using an Applied Biosystems 431A Peptide Synthesizer (Foster City, California). Mutated forms of the polypeptides may also be produced during such syntheses.

The polypeptides and variant polypeptides of the invention, or used in the methods of the invention, may also be purified from natural sources using a variety of techniques that are well known in the art (e.g. Deutscher, 1990, Ed, Methods in Enzymology, Vol. 182, Guide to Protein Purification,).

Alternatively the polypeptides and variant polypeptides of the invention, or used in the methods of the invention, may be expressed recombinantly in suitable host cells and separated from the cells as discussed below.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Polynucleotides, Constructs or Vectors The invention provides a host cell which comprises a genetic construct or vector of the invention.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides of the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide of the invention, or used in the methods of the invention. Plants comprising such cells also form an aspect of the invention.

Methods for transforming plant cells, plants and portions thereof with polypeptides are described in Draper et al., 1988, Plant Genetic Transformation and Gene Expression. A Laboratory Manual. Blackwell Sci. Pub. Oxford, p. 365; Potrykus and Spangenburg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

Methods for Genetic Manipulation of Plants

A number of plant transformation strategies are available (e.g. Birch, 1997, Ann Rev Plant Phys Plant Mol Biol, 48, 297, Hellens R P, et al (2000) Plant Mol Biol 42:819-32, Hellens R et al Plant Meth 1:13). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed. Such strategies are known as gene silencing strategies.

Genetic constructs for expression of genes in transgenic plants typically include promoters for driving the expression of one or more cloned polynucleotide, terminators and selectable marker sequences to detect presence of the genetic construct in the transformed plant.

The promoters suitable for use in the constructs of this invention are functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues, respond to internal developmental signals or external abiotic or biotic stresses are described in the scientific literature. Exemplary promoters are described, e.g., in WO 02/00894, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zein gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Those skilled in the art will understand that polynucleotides and constructs for expressing polypeptides in cells and plants can include various other modifications including restriction sites, recombination/excision sites, codon optomisiation, tags to facilitate protein purification, etc. Those skilled in the art will understand how to utilise such modifications, some of which may influence transgene expression, stability and translation. However, an art skilled worker would also understand that these modifications are not essential, and do not limit the scope of the invention.

The following are representative publications disclosing genetic transformation protocols that can be used to genetically transform the following plant species: Rice (Alam et al., 1999, Plant Cell Rep. 18, 572); apple (Yao et al., 1995, Plant Cell Reports 14, 407-412); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9: 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); grasses (U.S. Pat. Nos. 5,187,073 and 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792,935); soybean (U.S. Pat. Nos. 5,416, 011; 5,569,834; 5,824,877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); *brassica* (U.S. Pat. Nos. 5,188,958; 5,463, 174 and 5,750,871); cereals (U.S. Pat. No. 6,074,877); pear (Matsuda et al., 2005, Plant Cell Rep. 24 (1): 45-51); *Prunus* (Ramesh et al., 2006 Plant Cell Rep. 25 (8): 821-8; Song and Sink 2005 Plant Cell Rep. 2006; 25 (2): 117-23; Gonzalez Padilla et al., 2003 Plant Cell Rep. 22 (1): 38-45); strawberry (Oosumi et al., 2006 Planta. 223 (6): 1219-30; Folta et al., 2006 Planta April 14; PMID: 16614818), rose (Li et al., 2003), *Rubus* (Graham et al., 1995 Methods Mol Biol. 1995; 44:129-33), tomato (Dan et al., 2006, Plant Cell Reports V25: 432-441), apple (Yao et al., 1995, Plant Cell Rep. 14, 407-412), Canola (*Brassica napus* L.). (Cardoza and Stewart, 2006 Methods Mol Biol. 343:257-66), safflower (Orlikowska et al, 1995, Plant Cell Tissue and Organ Culture 40:85-91), ryegrass (Altpeter et al, 2004 Developments in Plant Breeding 11 (7): 255-250), rice (Christou et al, 1991 Nature Biotech. 9:957-962), maize (Wang et al 2009 In: Handbook of Maize pp. 609-639) and *Actinidia eriantha* (Wang et al., 2006, Plant Cell Rep. 25, 5:425-31). Transformation of other species is also contemplated by the invention. Suitable methods and protocols are available in the scientific literature.

Modification of Endogenous Genomes

Targeted genome editing using engineered nucleases such as clustered, regularly interspaced, short palindromic repeat (CRISPR) technology, is an important new approach for generating RNA-guided nucleases, such as Cas9, with customizable specificities. Genome editing mediated by these nucleases has been used to rapidly, easily and efficiently modify endogenous genes in a wide variety of cell types and in organisms that have traditionally been challenging to manipulate genetically. A modified version of the CRISPR-Cas9 system has been developed to recruit heterologous domains that can regulate endogenous gene expression or label specific genomic loci in living cells (Nature Biotechnology 32, 347-355 (2014). The system is applicable to plants, and can be used to regulate expression of target genes. (Bortesi and Fischer, Biotechnology Advances Volume 33, Issue 1, January-February 2015, Pages 41-52). Use of CRISPR technology in plants is also reviewed in Zhang et al., 2019, Nature Plants, Volume 5, pages 778-794.

Plants

The term "plant" is intended to include a whole plant, any part of a plant, a seed, a fruit, propagules and progeny of a plant.

The term 'propagule' means any part of a plant that may be used in reproduction or propagation, either sexual or asexual, including seeds and cuttings.

The plants of the invention may be grown and either self-ed or crossed with a different plant strain and the resulting hybrids, with the desired phenotypic characteristics, may be identified. Two or more generations may be grown to ensure that the subject phenotypic characteristics are stably maintained and inherited. Plants resulting from such standard breeding approaches also form an aspect of the present invention.

EXAMPLES

Figure 1:
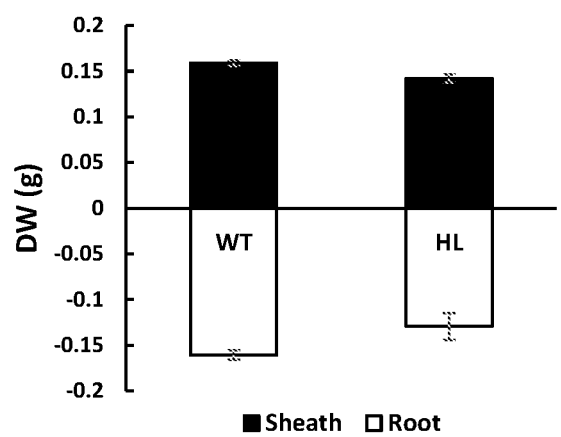
FIG. 1 shows sheath and root DW of a defoliated clonal cys-OLE/DGAT ryegrass transformant (HL) and a wild type control (WT) genotype. Plants were established from 3-4 tillers for 23 days at 2 mM $NO_3-$ supply at ambient CO2. Bars represent the average for each genotype (n=5)±S.E.*=denotes a significant difference at the $p<0.05$ level in DW, according to student's t test.

This invention will now be illustrated with reference to the following non-limiting examples.

Example 1: Construct Designs

The Garden Nasturtium (*Tropaeolum majus*) DGAT1 peptide sequence (GenBank AAM03340) with the single point mutation of serine at 197 amino acid sequence to alanine as described by Xu et al. (2008), linked with V5 epitope tag (GKPIPNPLLGLDST-SEQ ID NO: 51) at the C-terminal (DGAT1-V5), and the 15-kD sesame L-oleosin (accession no. AAD42942) with three engineered cysteine residues on each N- and C-terminal amphipathic arms (Cys-OLE; Winichayakul et al., 2013) were custom synthesized by a gene synthesizer (GeneART™) for expression in *L. perenne* (sequences 1-4) Both DGAT1-V5 and Cys-OLE coding sequences were optimized for expression in monocot grass and placed into the designed Gene Gun compatible construct. The resulting construct, labelled as LpD103-3, contained the DGAT1-V5 gene regulated by the rice ribulose-1, 5-bisphosphate carboxylase small subunit promoter (RuBisCO-Sp, GenBank AY583764) back-to-back with the Cys-OLE gene regulated by the rice chlorophyll a/b binding protein promoter (CABp; GenBank AP014965-region: 10845004-10845835).

The same peptide sequences were optimized for expression in *Glycine max* and were placed under a variety of promoter combinations including but not limited to:
- *Phaseolus vulgaris* ribulose 1,5-bisphosphate carboxylase/oxygenase small subunit (rbcS2) promoter, Accession number AF028707
- *Pisum sativum* small subunit ribulose bisphosphate carboxylase (rbcS-3A) promoter, Accession numbers M21356; M27973
- *Pisum sativum* CAB promoter, Accession number M64619
- *Glycine max* Subunit-1 ubiquitin promoter, Accession number D16248
- *Arabidopsis thaliana* polyubiquitin 10 promoter, Accession number L05399
- Cauliflower mosaic virus 35s promoter, Accession numbers V00141; J02048

These were subcloned into binary vectors for *Agrobacterium tumefaciens* assisted transformation.

The same peptide sequences were optimized for expression in *Cannabis sativa* (sequences 9-12) and were placed under a variety of promoter combinations including but not limited to:
- *Phaseolus vulgaris* ribulose 1,5-bisphosphate carboxylase/oxygenase small subunit (rbcS2) promoter, Accession number AF028707
- *Pisum sativum* small subunit ribulose bisphosphate carboxylase (rbcS-3A) promoter, Accession numbers M21356; M27973
- *Pisum sativum* CAB promoter, Accession number M64619
- *Glycine max* Subunit-1 ubiquitin promoter, Accession number D16248
- *Arabidopsis thaliana* polyubiquitin 10 promoter, Accession number L05399
- Cauliflower mosaic virus 35s promoter, Accession numbers V00141; J02048

These were subcloned into binary vectors for *Agrobacterium tumefaciens* assisted transformation.

Example 2: *Lolium perenne* Transformation, Selection and Growth Conditions

Plants over-expressing the LpDlo3-3 construct were generated by microprojectile bombardment using a method adapted from Altpeter et al. (2000). Briefly, calli for transformation were induced from immature inflorescences harvested from a single transformation-competent genotype of cvr. Impact by culture on a Murashige Skoog basal medium supplemented with 2,4-dichlorophenoxyacetic acid. Plasmids for transformation were prepared using the Invitrogen Pure Link Hi Pure Plasmid Maxiprep Kit. The plasmid pAcH1, which contains an expression cassette comprising a chimeric hygromycin phosphotransferase (HPH) gene (Bilang et al., 1991) expressed from the rice actin promoter, was used for selection and mixed in a 1:1 molar ratio with LpDlo3-3. Plasmid DNA's were coated onto M17 tungsten particles using the method of Sanford et al. (1993) and co-transformed into target tissues using a DuPont PDS-1000/He Biolistic Particle Delivery System. Multiple independent heterozygous ryegrass transformants were generated, including transgenic plants transformed with pAcH1 as a vector control (VC). Transformed plants were transferred to a contained greenhouse environment (22/17° C. diurnal cycle and 12 hour photoperiod under supplementary LED lighting providing 1000 μM/sec/m² PAR) for further analysis.

PCR analysis using primer pair's specific to the HPH and DGAT genes was performed to confirm stable integration of the transgenes into the genome of plants recovered from transformation experiments, and Southern blot hybridization was used to estimate the number of transgene copies per line. Leaves from these plants were initially analysed for total fatty acid content and recombinant DGAT1-V5 and Cys-OLE proteins.

Example 3: *Glycine max* Transformation

*Glycine max* can be transformed and selected essentially as described in Zeng, P. et al 2004, Plant Cell Reports, 22:478-482, and Paz N, M. et al., 2004, Euphytica, 136: 167-179.

Example 4: *Cannabis sativa* Transformation

*Cannabis sativa* can be transformed and selected essentially as described in Feeney and Punja (2003).

Example 5: Reduction of Water Soluble Carbohydrate in *Lolium perenne*

Plant Material and Experimental Layout

Plant material was transformed with cysteine-oleosin and DGAT1 under the control of the *Oryza sativa* CAB and RuBisCo promoters respectively as described in Roberts et al 2010; Roberts et al 2011; Beechy-Gradwell et al (2018);

The untransformed wild type (WT) control genotype 'IMPACT 566' used throughout this work was derived from the perennial ryegrass (*Lolium perenne*) cultivar 'Grasslands Impact' which was selected for its amenability to transformation and regeneration. Replicate plants in all experiments consisted of vegetative clonal ramets of WT or independent WT transformation events. Therefore, the transgenic genotypes differed genetically from the WT only in the presence of the cys-OLE/DGAT construct, while the transgenic genotypes differed genetically from one another only in the position and copy number of the cys-OLE/DGAT construct in the genome.

Experiments were conducted either in the glasshouse or in controlled environment growth chambers. Total leaf fatty acid (FA) and recombinant protein content were initially determined for WT, a vector control (VC) and 12 independent transgenic cys-OLE/DGAT genotypes, grown in the glasshouse under regular mechanical defoliation. WT, VC, and the transgenic genotypes '3501' and '3807' were also analysed for leaf TAG and root FA content, with samples taken approximately three weeks after defoliation (n=6-8). WT and the transgenic genotypes '3501' and '6205' were used in a preliminary growth trial at ambient and elevated $[CO_2]$ across two growth chambers. Then, in the main experiment described in this study, the same growth chambers (with identical settings, described below) were used for a detailed physiological comparison of WT and the high-expressing genotype '6205' (HL), in a formal regrowth trial at ambient and elevated atmospheric $[CO_2]$ under different levels of $NO_3^-$ and $NH_4^+$ supply.

Gas-Exchange Analysis

Rates of $CO_2$ assimilation were measured from plants growing 3-WAC using an infrared gas analyzer (Li6400; Li-Cor Inc.) fitted with a standard 2×3-cm$^{-2}$ leaf chamber, a leaf thermocouple, and a blue-red light-emitting diode light source at 1500 μmol·m$^{-2}$·s$^{-1}$ photosynthetically active radiation. Intrinsic water-use efficiency (iWUE) was estimated from the ratio of photosynthesis/stomata conductance (Osmond et al., 1980). Block temperature was held at 20° C., stomata ratio was set at 1, and the vapour pressure deficit was between 0.8 and 1.3 kPa.

SDS-PAGE Analysis of DGAT1 and Cys-OLE

Protein samples were prepared by collecting fresh 4 ryegrass leaf blades (approximately 2 cm long) or 10 mg DW finely ground leaf in a 2-mL screw cap micro tube containing 150 μL of sterile $H_2O$, 200 μL of 2× protein loading buffer (1:2 diluted 4× lithium dodecyl sulfate (LDS) sample buffer [Life Technologies], 8 M urea, 5% [v/v] β-mercaptoethanol, and 0.2 M dithiothreitol). The mixtures were homogenised using the Omni Bead Ruptor 24 model setting at speed level 5 until totally homogenised. The samples were heated at 70° C. for 10 min, centrifuged at 20,000 g for 30 sec and collected for the soluble protein suspension. Equal quantities of proteins were determined and separated by SDS-PAGE (Mini-PROTEAN® TGX Stain-free™ precast gels; Bio-Rad) and blotted onto Bio-Rad polyvinylidene difluoride (PVDF) membrane for the DGAT1-V5 immunoblotting. Equivalent amounts of proteins were separated on gradient 4-12% Bis-Tris gel (NU-PAGE; Life Technologies) and blotted onto nitrocellulose membrane for the Cys-OLE immunoblotting. Immunoblotting was performed as described previously in Winichayakul et al. (2013). Chemiluminescent activity was developed using Advansta WesternBright ECL spray and visualised by Bio-Rad ChemiDoc™ imaging system. To prepare protein samples for the LD fraction analysis, an equal volume of LD was mixed to the 2× protein loading buffer and heated at 70° C. for 10 min.

Ribulose 1, 5-bisphosphate carboxylase large subunit (RuBisCO-L) extraction and analysis Approximately 10 mg of freeze-dried finely ground leaf material was accurately weighed and extracted in 0.5 mL of phosphate buffer saline (PBS) pH 7.4. The extract was centrifuged at 10,000 g for 5 min at 22° C. and the soluble fraction was determined for protein content using Qubit Protein Assay Kits/Qubit 2.0

Fluorometer (ThermoFisher). Protein samples were prepared by mixing similar volumes of extract with 2× sample loading buffer (1:2 diluted 4×LDS sample buffer [Life Technologies], 5% [v/v] β-mercaptoethanol, and 0.2 M dithiothreitol) and heated at 70° C. for 10 min. Equal quantities of proteins were separated by SDS-PAGE. The amount of RuBisCo-L protein was visualised directly from the gels and confirmed by immunoblotting using anti-RuBisCo-L (1:5000 dilution; Agrisera AS03 037).

Chlorophyll Extraction

Approximately 10-15 mg of freeze-dried finely ground leaf material was accurately weighed and extracted with 2 mL of ethanol (95% v/v) in sealed glass tubes kept at 22° C. in the dark. Extraction was regularly mixed thoroughly for 3 h or until the leaf materials turned white. Chlorophyll a and b content in the extracts was measured spectrophotometrically for the absorbance at 648 and 664 nm and calculated as described by Lichtenthaler and Buschmann (2001) using the following equations chlorophyll a=(13.36 $A_{664}$-5.19 $A_{648}$), chlorophyll b=(27.43 $A_{648}$-8.12 $A_{664}$).

Stomatal Aperture Bioassays

Plants were watered well at beginning of the day light. After 3 h, leaves were harvested and immediately fixed in cold 4% (w/v) paraformaldehyde in 1×PBS with 10 min vacuum treatment and incubated in the fixing agent at 4° C. for at least overnight. Fixed leaves were washed twice with 1×PBS and stained with 20 μL of SlowFade®Gold Anti-Fade Mountant with 4',6-diamidino-2-phenylindole (DAPI; Life Technologies S36938) for fluorescence imaging and visualized using confocal microscopy with the excitation/emission max (Ex/Em) set at 359/461 nm for DAPI fluorescence. Measurements of stomatal aperture were carried out on at least 60 stomatal apertures (5 images taken from one leaf abaxial epidermis, 12 biological repeats) as described previously by Merlot et al. (2001) using the Olympus Fluoview FV10-ASW 3.1 Software.

Establishment Phase for Ryegrass Clones

In the main experiment described in this study, WT and HL clones were made from established plants by splitting them into ramets consisting of 3-4 tillers and cutting to 10 cm of combined root and shoot length. The ramets were placed in individual cylindrical plastic pots containing washed sand (1.6 L). Approximately 200 clones of each genotype were generated, of which 140 were selected (based on a uniform leaf DW) for the experiment. Following propagation, the ramets were given 23 days to establish a root system in a Conviron BDW 120 plant growth room at ambient $CO_2$ (Thermo-Fisher, Auckland, NZ). Metal halide bulbs (400 W Venture Ltd., Mount Maunganui, NZ) and soft tone, white incandescent bulbs (100 W, Philips, Auckland, NZ) provided ~500±50 μmol photosynthetically active radiation (PAR) $m^{-2}$ $s^{-1}$ as white light, under a 12 hour photoperiod, with light levels ramping at dawn/dusk for 60 minutes. The day/night temperature and humidity were 20/15° C. and 60/68% RH, respectively. A top-down airflow pattern, with a controlled flow of outdoor air, maintained ambient $CO_2$ conditions (~400 ppm. $CO_2$). During the establishment period, pots were flushed with 100 ml of basal nutrient media described in (Andrews et al., 1989) containing 2 mM $KNO_3$, three times per week. We found that supplying sub-optimal $NO_3^-$ limited establishment phase growth enough to avoid 'pot-limited' conditions (Poorter et al., 2012) early in the subsequent regrowth phase, while also avoiding severe 'transplanting shock'. At the end of the establishment phase, plants were defoliated and the DW of leaf clippings from 5 cm above the pot media surface were determined after oven-drying at 80° C. overnight. These averaged 0.118±0.036 g for the WT genotype and 0.113 g+0.020 for the HL genotype (Mean±SD, n=140). A subset of defoliated plants (n=5) were destructively sampled at this time, oven dried and weighed for 'sheath' (0-5 cm from the pot surface) and root DW, enabling the later calculation of relative growth rate (RGR).

Regrowth Phase for Ryegrass Clones

Following defoliation of the established plants, half of the material was moved into a second high $CO_2$ Conviron BDW 120 plant growth room, with identical settings to those described above, except that the $CO_2$ level was maintained at 760 ppm with G214 food grade $CO_2$ (BOC, Auckland, NZ). The two cabinets were previously tested for uniformity (Andrews et al., 2018). The $CO_2$ levels in both growth rooms were measured continuously using PP Systems WMA-4 Gas Analysers (John Morris Scientific, Auckland, NZ). Pots were randomly allocated to different N treatments (n=5) then flushed with 150 ml of basal nutrient media containing either 1, 2, 3, 4, 5, 7.5 or 10 mM of N as either $NO_3^-$ or $NH_4^+$ every two days for the regrowth phase. The pH of the nutrient media solutions was in the range of 5.4-5.6. Potassium concentrations were balanced in all cases with the highest potassium treatment (10 mM) with $K_2SO_4$ but sulphate was not balanced.

Harvest of Ryegrass Clones

Plants were destructively harvested after 29-30 days regrowth and divided into 'leaf' (5 cm above the pot surface), 'sheath' (0-5 cm from the pot surface) and roots. Leaf subsamples were taken from plants treated with 3, 5, 7.5 and 10 mM N and snap frozen in liquid N, then stored at −80° C. The remaining material was oven dried at 65° C. for 4-6 days then weighed. Roots were cleaned and oven dried at 65° C. for 4-6 days before weighing. The fraction of biomass allocated to leaves (LMF) was calculated by dividing leaf DW by total plant DW. RGR was calculated from differences in paired plant DW, determined after defoliation (FIG. 1) and after the regrowth phase. A non-biased plant pairing method (Poorter, 1989a) was used, based on end of establishment leaf DW. RGR calculation eliminated possible confounding differences in absolute DW data arising from clonal propagation (Beechey-Gradwell et al., 2018).

Lipid and Carbohydrate Analyses

The frozen leaf material was later freeze-dried and ground to a powder and analysed for fatty acids (FA) and water-soluble carbohydrates (WSC). FA were extracted from 10-15 mg of ground sample and methylated in hot methanolic HCl, then quantified against a C15:0 internal standard by GC-MS (Browse et al., 1986). Total FA concentration was calculated as the sum of palmitic acid (16:0), palmitoleic acid (16:1), stearic acid (18:0), oleic acid (18:1), linoleic acid (18:2) and linolenic acid (18:3) concentration in the leaves. The protocol for TAG extraction was as described in Winichayakul et al. (2013) without modification. For WSC, a 25 mg sample of ground material was mixed twice with 1 ml 80% ethanol and incubated at 65° C. for 30 min. After each extraction the homogenate was centrifuged at 13,000 rpm for 10 min and the supernatant containing low molecular weight (LMW) WSC was removed. High molecular weight (HMW) WSC were extracted by twice mixing the remaining insoluble residue with 1 ml of water, then incubating, centrifuging and removing the supernatant. Aliquots of these extracts were diluted then reacted with 1.25% anthrone in a mixture of $H_2SO_4$ and ethanol (3:5 V:V). The blue-green colour produced from the reaction was read at 620 nm. LMW and HMW WSC were calibrated against a series of sucrose and inulin standards, respectively.

Statistical Analysis

A complete randomised study design was used to investigate the relationship between genotype, $CO_2$, N form and N concentration on various growth parameters, leaf FA and leaf WSC. Two or three-way ANOVA were used to compare the gas exchange, leaf structure and fluorescence data (collected at a single N concentration). For growth parameters, N concentration was treated as a continuous variable. For leaf FA and leaf WSC, N concentration was treated as a factor. A forward stepwise procedure was used for selecting variables. Variables and interaction terms with a p-value of <0.05 were retained in the final model. Due to residual heteroskedasticity, total plant DW data was log-transformed before modelling. Treatment means were compared and post hoc multiple comparison p-values were adjusted using the Benjamini-Hochberg (BH) method. Raw means and SE values are presented in the tables and figures, while p-values in the tables and text were obtained from the final statistical models. All statistical analyses were performed in R (Version 3.4.3, R foundation).

Leaf Fatty Acid and Protein Expression

Figure 2:
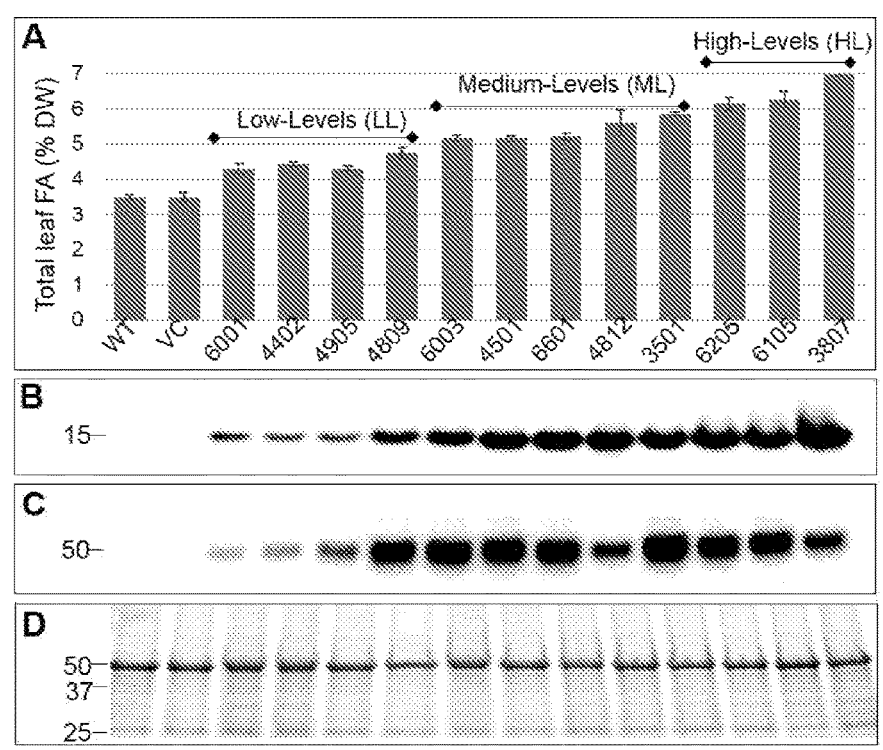
FIG. 2 shows total leaf FA and relative recombinant protein (cys-OLE and DGAT) content of 12 independent ryegrass transformants. Samples were taken from leaf regrowth three weeks after propagation and cutting. A) Total leaf FA as a percentage of DW; bars represent averages (n=6-8)±S.E., B) Relative recombinant cys-OLE content, C) Relative recombinant DGAT content, D) Bio-Rad stain-free SDS-PAGE image showing equal loading of protein in each gel. The positions of the protein molecular weight markers are indicated in kDa, wild type=WT; vector control=VC.
Figure 3:
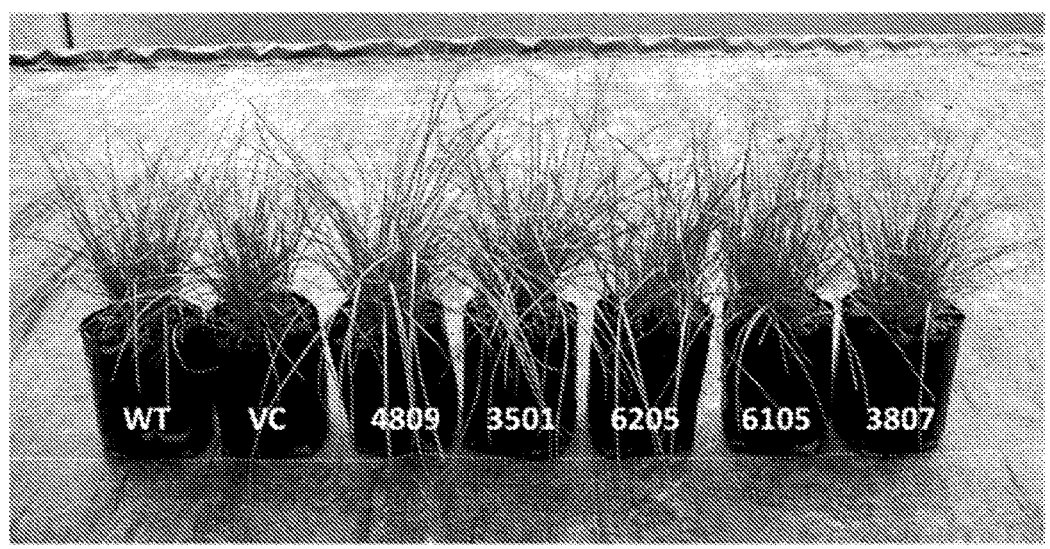
FIG. 3 shows visual comparison of shoot regrowth of cys-OLE/DGAT transformants with a WT and VC genotype. Ramets consisting of 5 tillers were placed in pots and trimmed to an even height every 3 weeks for 3 months.

In an initial screen of the transgenic material, there was no significant difference between WT and vector control leaf FA, while the cys-OLE/DGAT lines contained 23-100% more leaf FA (4.3-7.0% DW) than the WT (3.5% DW) (FIG. 2A). Leaf FA concentration correlated closely with the expression of cys-OLE (FIG. 2B), but not DGAT (FIG. 2C). Leaf TAG accumulated to 2.5% DW in the highest expressing cys-OLE/DGAT line, compared to 0.18% DW in the WT (Table 3 below). Root FA was 10 and ~50% higher in the vector control and cys-OLE/DGAT lines, respectively, than the WT (Table 3 below). Upon arranging the cys-OLE/DGAT lines according to leaf FA concentration, a possible leaf expansion and/or regrowth advantage was visually observed in the cys-OLE/DGAT lines with a leaf FA concentration of ~5-6% DW (including 3501 and 6205), while an apparent growth penalty occurred in the highest expressing cys-OLE/DGAT line (3807) with a leaf FA concentration of ~7% DW (FIG. 3).

TABLE 3

| Genotype | Total leaf FA (% DW) | Leaf TAG (% DW) | Total root FA (% DW) |
|---|---|---|---|
| WT | 3.49 ± 0.07 A | 0.18 ± 0.03 A | 0.66 ± 0.01 A |
| VC | 3.50 ± 0.13 A | 0.23 ± 0.02 A | 0.73 ± 0.01 B |
| 3501 | 5.56 ± 0.06 B | 2.20 ± 0.06 B | 0.99 ± 0.01 C |
| 3807 | 6.69 ± 0.07 C | 2.47 ± 0.06 C | 0.97 ± 0.01 C |
| p value | ** | *** | *** |

Leaf C Storage

Figure 4:
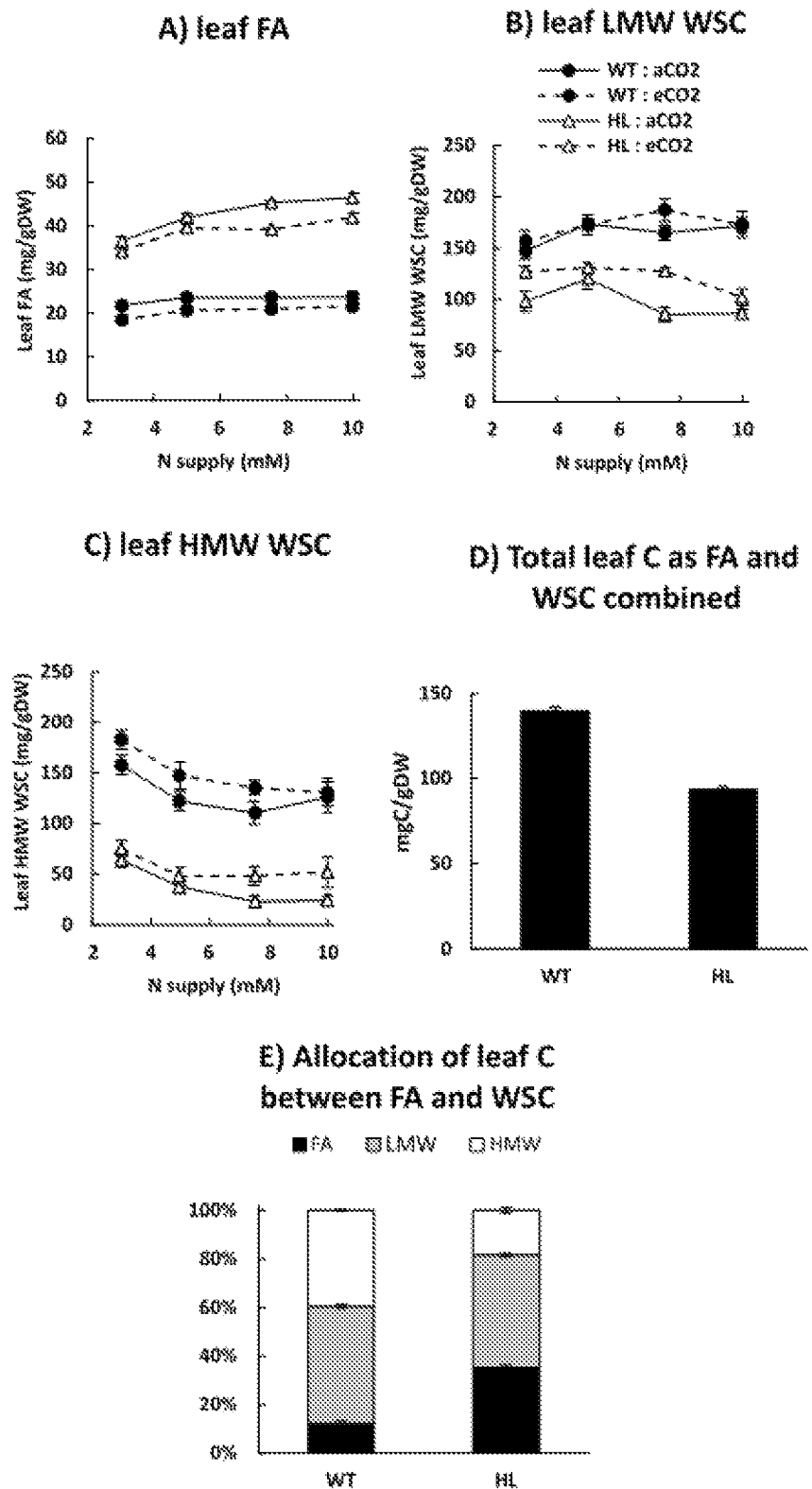
FIG. 4 shows leaf C storage of a clonal cys-OLE/DGAT ryegrass transformant (HL; open triangles) and a wild type control (WT; closed circles) genotype. A) leaf fatty acids (FA), B) LMW (low molecular weight) leaf water-soluble carbohydrates (WSC), C) HMW (high molecular weight) leaf WSC, D) total C allocated to leaf FA and WSC combined, E) the proportions of leaf C as FA and WSC relative to one another (where 100%=total leaf C allocated to these potential storage pools). Plants were regrown for 28-29 days after defoliation at 1-10 mM N supply at either ambient (400 ppm) or elevated CO2 (760 ppm). In A, B and C data points represent raw averages for plants regrown under NO3− and NH4+ (n=10)±S.E. In D and E bars represent an average over all N and CO2 treatments (n=80)+S.E. aCO2=ambient CO2, eCO2=elevated CO2.

In the main experiment described in this study, the high expressing cys-OLE/DGAT genotype '6205' (HL) had a substantially higher (67-96%) leaf FA concentration than the WT under two $CO_2$ levels and 1-10 mM N supply (Genotype effect p<0.001) (FIG. 2A). For both WT and HL, total leaf FA concentration decreased slightly at $e[CO_2]$ and increased with increasing N supply up until 5-10 mM, before stabilizing (FIG. 2A). HL leaf WSC concentration was substantially lower than in the WT under both a $[CO_2]$ and $e[CO_2]$ (Genotype effect p<0.001) (FIG. 4B, 2C), especially in the high molecular weight fraction (HMW, primarily fructans) which were 3-5 fold lower for HL than WT leaves at 7.5-10 mM N supply (FIG. 4C). Leaf WSC was higher at $e[CO_2]$ (FIG. 4B, 3C), and tended to decrease with increasing $NO_3^-$ supply (N form x N concentration interaction p<0.01) (data not shown). Since FAs contain more energy and C than carbohydrates, the total C stored as leaf FA and WSC was calculated for each genotype. The overall differences in WT and HL leaf C storage (FIG. 4E) were such that the total concentration of C stored as leaf FA and WSC was substantially less in HL than in WT (FIG. 4D).

Growth

After 28-29 days regrowth under the different $[CO_2]$ and N treatments, total plant dry biomass (DW) increased by 7 to 23-fold. For both WT and HL, DW was greater under $e[CO_2]$ than a $[CO_2]$ and increased with N supply up until 4-10 mM (N concentration effect p<0.001), then stabilized or decreased thereafter (Quadratic N concentration effect p<0.001). The DW of (defoliated) plants at the end of the establishment phase was 18% greater for WT than for HL plants (p<0.01 student's t-test, Figure S1). By the final harvest however, HL DW was greater than WT at high N supply, and similar at low N supply (Genotype x N concentration interaction p<0.05) (FIG. 5A, 5B). The relative growth rate (RGR) between post-establishment defoliation and the final harvest was also greater for HL than WT, and at most levels of N supply (Genotype effect p<0.001) (FIG. 5C, 5D). DW was slightly greater under high $NO_3^-$ supply compared to high $NH_4^+$ supply (N form x concentration interaction p<0.05, data not shown), but the increase in DW that occurred at $e[CO_2]$ relative to a $[CO_2]$ was similar with $NO_3^-$ and $NH_4^+$ (i.e. no $CO_2$×N form interaction occurred) (data not shown).

Morphology

The fraction of biomass allocated to leaves (LMF) increased with increasing N supply up until 5-7.5 mM, then stabilized thereafter (Quadratic N concentration effect p<0.001) (FIG. 5E, 5F). LMF was substantially lower for HL at low N supply, but this difference became progressively smaller as N supply increased, such that at 7.5 mM N supply HL had only a slightly lower LMF than WT (10% when averaged across $[CO_2]$ levels and N forms) (Quadratic N concentration x Genotype interaction p<0.001) (FIG. 5E, 5F). HL had a correspondingly larger fraction of biomass allocated to roots than WT and a similar fraction of biomass allocated to sheath (data not shown). At 7.5 mM N supply, HL had a substantially higher SLA than WT (52% when averaged across $[CO_2]$ levels and N forms) (Genotype effect p<0.001) (Table 1). For both WT and HL, SLA was lower at $e[CO_2]$ than a $[CO_2]$ and higher under $NO_3^-$ than $NH_4^+$ supply (Table 1). HL had a higher projected total leaf area to total plant DW ratio than WT (35% when averaged across $[CO_2]$ levels and N forms).

Gas Exchange

HL displayed a higher $A_{sat}$ than WT at a $[CO_2]$ (Genotype effect p<0.001). Similar results were also obtained when A was measured at growth room irradiance (~500 μmol m$^{-2}$ s$^{-1}$) (data not shown). For both WT and HL, $A_{sat}$ increased and stomatal conductance ($g_s$) decreased at $e[CO_2]$ ($CO_2$ effect, p<0.001), however the increase in $A_{sat}$ at $e[CO_2]$ compared to a $[CO_2]$ was greater for HL than for WT (Genotype x $CO_2$ interaction, p<0.01) (Table 1). Relative to $NO_3^-$ supply, $NH_4^+$ increased HL $A_{sat}$ (by 9%) and decreased WT $A_{sat}$ (by 29%) (Genotype x N form interaction p<0.001). Within $[CO_2]$ treatments, light saturated $g_r$ and $A_{area}$ correlated well ($R^2$=0.79 under a $[CO_2]$ and 0.74 $e[CO_2]$, respectively) (Figure S3) and the ratio of leaf intracellular $CO_2$ to ambient $CO_2$ concentration ($C_i$/Ca) did not differ between WT and HL, regardless of $[CO_2]$ level or N form (Table 4 below).

Figure 6:
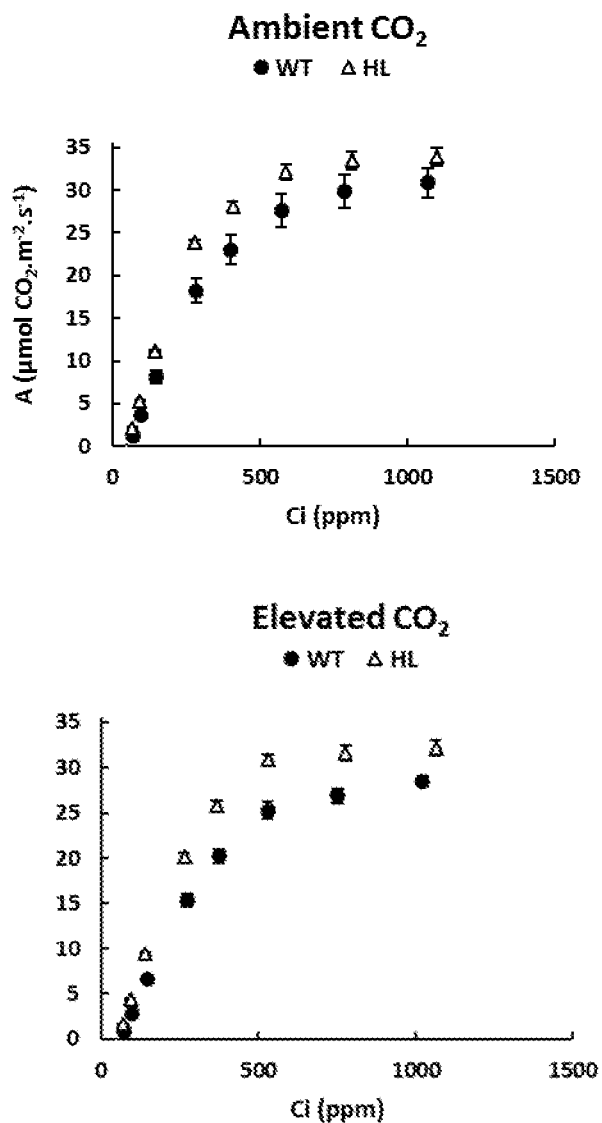
FIG. 6 shows response of net photosynthesis per unit leaf area (A) to intracellular CO2 concentration (Ci) of a clonal cys-OLE/DGAT ryegrass transformant (HL; open triangles) and a wild type control (WT; closed circles) genotype. Plants were regrown at 5 mM NO3− supply under ambient (400 ppm) and at 7.5 mM NO3− supply under elevated CO2 (760 ppm). Data points represent the raw averages (n=5)±S.E.

A/Ci analysis, determined for plants supplied with NO; only, showed that HL had a substantially higher $A_{sat}$ at low (rubisco-limited) $C_i$ (68-83% at 69-72 ppm $C_i$) compared to WT. This difference became smaller at high (RuBP regeneration-limited) $C_i$ (10-12% at 1023-1099 ppm $C_i$) (FIG. 6). The modelled maximum velocity of rubisco carboxylation ($V_{c,max}$) decreased at $e[CO_2]$ ($CO_2$ effect, p<0.01), especially for the WT (Table S3). HL had a greater Φ PSII than WT (Genotype effect, p<0.001) and a lower $V_o/V_c$ and % inhibition of $A_{amb}$ at 20% $O_2$ than the WT (Genotype effect, p<0.001) (Table 2). $V_o/V_c$ and the inhibition of $A_{amb}$ at 20% $O_2$ decreased at $e[CO_2]$ ($CO_2$ effect, p<0.001) and $V_o/V_c$ also decreased with $NH_4^+$ compared to NO; supply (N form effect, p<0.05) (Table 5 below).

TABLE 4

| $CO_2$ | N form | Genotype | SLA ($cm^2.g.DW^{-1}$) | $A_{sat}$ ($\mu mol\ CO_2.m^{-2}.s^{-1}$) | $g_s$ ($CO_2.m^{-2}.s^{-1}$) | $A_{mass}$ ($\mu mol\ CO_2.gDW^{-1}.s^{-1}$) | $C_i/C_a$ |
|---|---|---|---|---|---|---|---|
| Ambient | $NO_3^-$ | WT | 211 ± 9 C | 19.1 ± 0.9 D | 0.32 ± 0.03 B | 0.41 ± 0.03 D | 0.71 ± 0.01 AB |
| | | HL | 290 ± 8 A | 23.3 ± 0.2 C | 0.40 ± 0.01 A | 0.68 ± 0.02 B | 0.71 ± 0.01 AB |
| | $NH_4^+$ | WT | 155 ± 3 DE | 15.6 ± 0.6 E | 0.22 ± 0.01 D | 0.24 ± 0.01 E | 0.67 ± 0.01 BC |
| | | HL | 244 ± 9 B | 24.8 ± 1.2 C | 0.36 ± 0.02 AB | 0.60 ± 0.02 C | 0.66 ± 0.01 C |
| Elevated | $NO_3^-$ | WT | 174 ± 11 D | 25.3 ± 0.9 C | 0.23 ± 0.02 D | 0.44 ± 0.04 D | 0.72 ± 0.02 A |
| | | HL | 277 ± 9 A | 30.8 ± 0.6 B | 0.30 ± 0.02 BC | 0.85 ± 0.01 A | 0.73 ± 0.02 A |
| | $NH_4^+$ | WT | 150 ± 7 E | 18.8 ± 0.9 D | 0.13 ± 0.01 E | 0.29 ± 0.03 E | 0.67 ± 0.02 BC |
| | | HL | 231 ± 3 BC | 34.6 ± 1.1 A | 0.25 ± 0.02 CD | 0.80 ± 0.03 A | 0.66 ± 0.02 C |
| | | G | *** | *** | *** | *** | — |
| | | N | *** | — | *** | *** | *** |
| | | $CO_2$ | ** | *** | *** | *** | — |
| | ANOVA | G × N | — | *** | — | ** | — |
| | | G × $CO_2$ | — | ** | — | *** | — |
| | | N × $CO_2$ | — | — | — | — | — |

Data points represent the raw averages of plants regrown under $NO_3^-$ or $NH_4^+$ (n = 5) ± S.E. G = genotype effect, N = N form effect, $CO_2$ = $CO_2$ effect significant in a three-way ANOVA.
\* = p < 0.05,
\*\* = p < 0.01,
\*\*\* = p < 0.001. Different letters indicate statistically significant differences in predicted means obtained from three-way ANOVA, with p values adjusted according to BH method.

TABLE 5

| $CO_2$ | N form | Genotype | Φ PSII | Vo/Vc | % inhibition in $A_{amb}$ at 20% $O_2$ |
|---|---|---|---|---|---|
| Ambient | $NO_3^-$ | WT | 0.42 ± 0.02 | 0.35 ± 0.02 | 34 ± 1 |
| | | HL | 0.54 ± 0.01 | 0.29 ± 0.01 | 29 ± 1 |
| | $NH_4^+$ | WT | 0.40 ± 0.02 | 0.41 ± 0.02 | 37 ± 2 |
| | | HL | 0.54 ± 0.01 | 0.31 ± 0.03 | 30 ± 2 |
| Elevated | $NO_3^-$ | WT | 0.40 ± 0.01 | 0.18 ± 0.01 | 15 ± 2 |
| | | HL | 0.55 ± 0.01 | 0.13 ± 0.01 | 8 ± 2 |
| | $NH_4^+$ | WT | ND | ND | ND |
| | | HL | ND | ND | ND |
| | | G | *** | *** | *** |
| | | N | — | * | — |
| | ANOVA | $CO_2$ | — | *** | *** |
| | | G × N | — | — | — |
| | | G × $CO_2$ | — | — | |

Data points represent the raw averages of plants regrown under $NO_3^-$ or $NH_4^+$ (n = 5) ± S.E. $A_{amb}$ = photosynthesis at growth room irradiance. G = genotype effect, N = N form effect, $CO_2$ = $CO_2$ effect significant in a three-way ANOVA. * = p < 0.05,  = p < 0.01, * = p < 0.001. ND = Not determined.

The applicant has demonstrated that Cys-OLE/DGAT expression can be used to reduce water soluble carbohydrate and thereby confers a growth advantage with increased SLA and $A_{area}$ that improved yield. In addition the photosynthesis was more responsive to e[$CO_2$] at high N.

Without wishing to be bound by theory, the applicant postulate that production of a lipid carbon microsink leads to reduction in water soluble carbohydrate.

By modifying two genes involved in lipid biosynthesis and storage (cys-OLE/DGAT) the accumulation of stable lipid droplets in perennial ryegrass (Lolium perenne) leaves was achieved. Growth, biomass allocation, leaf structure, gas exchange parameters, fatty acids and water-soluble carbohydrates were quantified for a high-expressing cys-OLE/DGAT ryegrass transformant (HL) and a wild type (WT) control grown in controlled conditions under 1-10 mM N supply at ambient and elevated atmospheric $CO_2$. A dramatic shift in leaf C storage occurred in HL leaves, away from readily mobilizable carbohydrates and towards stable lipid droplets. Our results show that under ideal growing conditions, the manipulation of lipid biosynthesis and storage, and the resulting reduction in water soluble carbohydrate, can drive greater C assimilation. The applicant considers that lowering of WSC has a direct influence on the activity of photosynthetic machinery. The applicant's data predicate the present invention thus providing a more robust way of determining the influence on $CO_2$ assimilation as compared to measuring either accumulation of the cysteine oleosin protein or the accumulation of additional lipids within the leaf both of which have indirect influences on photosynthesis.

Example 6: Elevated Fatty Acids Over a Range of Levels in Leaves Comes at the Expense of Leaf Sugar and Coincides with Increase Carbon Assimilation and Growth Plant Material Lolium perenne, transformed with DGAT+Cysteine Oleosin (CO) using both agro-bacterium and gene-gun mediated transformation were used in these comparisons.

Relative Growth Rates

Five Lolium perenne lines containing DGAT+CO (labelled DGAT+CO1, DGAT+CO2, DGAT+CO3, DGAT+CO4, DGAT+CO5) were selected from three genetic backgrounds (Table 6). Three Lolium perenne containing DGAT+CO lines contained a single loci with the Lolium perenne containing transgenes and two containing multiple-loci (see Table 6). To eliminate growth form or tiller age differences between ramets, all *Lolium perenne* lines, and respective WT controls, underwent three rounds of propagation over 4 months. During each round, 5 ramets of five tillers each were potted and grown for 4 weeks. All plants were grown in a controlled temperature room with 600 µmol photons $m^{-2} s^{-1}$ red/blue light provided by **, 20° C./15° C. day/night temperature and 12 h day length. After the final round of propagation 40×5-tiller ramets were produced for each line, 10 of which were immediately harvested to confirm comparable starting weights (Table 7 below). The remaining 30 were transplanted into 1.3 L sand and flushed thrice weekly with 100 ml 2 mM $KNO_3$ in a complete nutrient solution. Three weeks after propagation, shoot material was harvested 5 cm above sand, and used to rank plants from smallest to largest. The five smallest and five largest plants per line were discarded and 10 of the remaining 20 plants per line were randomly selected and harvested (post-establishment harvest). The remaining ten plants per line were grown for another three weeks, with 8 mM $KNO_3$ applied as described above, and harvested (final harvest). Relative growth weight was calculated as per Poorter (1989a); $RGR=(\ln W_2-\ln W_1)/(t_2-t_1)$ where $W_1$=post-establishment dry weight, $W_2$=final harvest dry weight, $t_1$=day 22 and $t_2$=day 43.

TABLE 7

|  | Propagation DW (mg) | Post-Establishment DW (g) |
|---|---|---|
| WT1 | 92.8 (±5.1) | 0.82 (±0.04) |
| DGAT + CO1 | 101.7 (±5) | 0.7 * (±0.02) |
| DGAT + CO2 | 101.8 (±4.7) | 0.82 (±0.04) |
| WT2 | 107 (±7.7) | 0.57 (±0.03) |
| DGAT + CO3 | 114.3 (±5.5) | 0.73 ** (±0.03) |
| DGAT + CO4 | 105.6 (±5) | 0.72 * (±0.05) |
| WT3 | 114.9 (±10.6) | 0.55 (±0.02) |
| DGAT + CO5 | 94.1 (±5.1) | 0.65 (±0.05) |

Photosynthetic Gas Exchange

One week prior to the final harvest, three tillers were selected per plant, and on the youngest fully expanded leaves, net photosynthesis per unit leaf area (A), net photosynthesis per unit leaf mass ($A_{mass}$) stomatal conductance (gsw) and transpiration (E) was analysed using a Licor 6800 infrared gas exchange system (Licor Biosciences Ltd, Nebraska, USA). Leaves were acclimated under growing conditions; 600 µmol photons $m^{-2} s^{-1}$ red/blue light, at 400 ppm $CO_2$, 70% relative humidity and 20° C. for 15 minutes prior to data-logging. The three leaves were then abscised, photographed, dried and weighed. Leaf area was calculated using GIMP 2.8.22 (GNU Image Manipulation Program, gimp.org) and specific leaf area was calculated as SLA=LA/DW.

Fatty Acid Analysis

Leaf material was collected on the final day of our growth trial, freeze dried and ground via bead mill. 10 mg was sub-sampled per plant and from this, fatty acids (FA) were extracted in hot methanolic HCl (modified after Browse et al., 1986). FA were quantified by GC-MS (QP 2010 SE, Shimadzu Corp., Kyoto, Japan) against an internal standard of 10 mg C15:0 and total FA was calculated as the sum of palmitic acid (16:0), palmitoleic acid (16:1), stearic acid (18:0), oleic acid (18:1), linoleic acid (18:2) and linolenic acid (18:3).

Sugar Quantification

Total water soluble carbohydrates (WSC) were analysed using the anthrone method (Hedge Hofreiter, 1962). Using 25 mg freeze-dried, ground leaf material, low molecular weight carbohydrates (LMW) were twice extracted in 1 ml, 4:1 $EtOH:H_2O$ at 65° C. for 30 mins, centrifuged and supernatant collected and combined at each extraction. Using the sample pellet, high molecular weight carbohydrates (HMW) were twice extracted in 1 ml $H_2O$ at 65° C. for 30 mins, centrifuged and supernatant collected and combined at each extraction. The soluble carbohydrate extracts were mixed with anthrone reagent (Sigma-Aldrich, St Louis, MO, USA) for 25 mins at 65° C., A620 determined using a Versamax tunable plate reader (Molecular Devices Corporation, Sunnyvale, CA, USA) and compared to LMW and HMW standards, prepared using sucrose and inulin respectively.

Chlorophyll Quantification

Using 15 mg freeze-dried, ground leaf material, chlorophylls were extracted in $ethanol:H_2O$ (19:1), clarified by centrifugation and absorbance peaks measured using a Versamax tunable plate reader (Molecular Devices Corporation, Sunnyvale, CA, USA). Chlorophyll concentrations were determined from A664 and A648 using the formulae described by Lichtenthaler (1987).

Leaf Fatty Acid and Sugar Profiles

Figure 7:
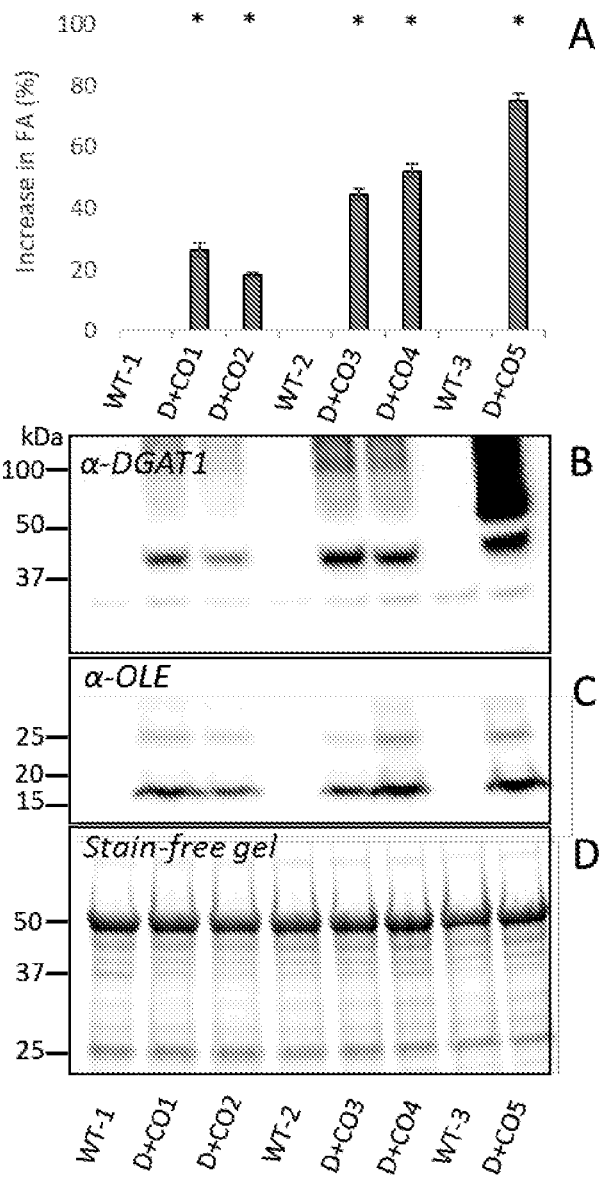
FIG. 7 shows percent difference (±SE) in leaf fatty acids compared to respective WT (A), recombinant protein contents for DGAT (B) and cysteine-oleosin (C), and stain free gel showing equal protein loading for each cell (D), for five DGAT+CO lines and three respective controls. *, P<0.01.

All HME lines displayed a significant increase in leaf fatty acids (FIG. 7), ranging from 118%-174% of respective WT controls. For HME, total fatty acids represented 4.7%-5.1% of total leaf DW, whereas WT lines ranged from 2.9%-4% total leaf DW (Table 6 below). The composition of fatty acids was significantly altered by HME expression, with all lines exhibiting a significant increase in the ratios of long-chain fatty acids C18:1, C18:2 and a decrease in the ratios of C16:0, C16:1 and C18:3 (Table 6 below).

TABLE 6

|  | C16:0 | C16:1 | C18:0 | C18:1 | C18:2 | C18:3 | Total FA (% DW) |
|---|---|---|---|---|---|---|---|
| WT1 | 11.52 (± 0.1) | 2.22 (± 0.04) | 1.04 (± 0.01) | 1.66 (± 0.04) | 12.8 (± 0.1) | 70.76 (± 0.2) | 4.04 (± 0.1) |
| DGAT + CO1 | 10.41 ** (± 0.1) | 1.96 ** (± 0.08) | 1.05 (± 0.02) | 5.8 ** (± 0.19) | 19.95 ** (± 0.21) | 60.83 ** (± 0.39) | 5.12 ** (± 0.09) |
| DGAT + CO2 | 10.67 ** (± 0.02) | 1.99 ** (± 0.04) | 0.91 ** (± 0.02) | 5.29 ** (± 0.1) | 18.56 ** (± 0.1) | 62.58 ** (± 0.19) | 4.78 ** (± 0.03) |
| WT2 | 11.38 (± 0.1) | 2.7 (± 0.05) | 0.99 (± 0.02) | 1.44 (± 0.05) | 13.96 (± 0.3) | 69.52 (± 0.3) | 3.64 (± 0.1) |
| DGAT + CO3 | 10.38 ** (± 0.1) | 2.47 ** (± 0.05) | 0.96 (± 0.03) | 4.28 ** (± 0.05) | 18.7 ** (± 0.09) | 63.2 ** (± 0.13) | 5.25 ** (± 0.06) |
| DGAT + CO4 | 8.95 ** (± 1) | 2.07 ** (± 0.23) | 0.88 (± 0.11) | 6.36 ** (± 0.16) | 22.49 ** (± 0.08) | 57.97 ** (± 0.21) | 5.54 ** (± 0.08) |
| WT3 | 13.03 (± 0.1) | 2.2 (± 0.05) | 0.93 (± 0.01) | 1.05 (± 0.02) | 14.62 (± 0.2) | 68.17 (± 0.2) | 2.92 (± 0.1) |
| DGAT + CO5 | 12.29 ** (± 0.1) | 2.01 ** (± 0.04) | 0.97 (± 0.02) | 3.63 ** (± 0.08) | 22.47 ** (± 0.12) | 58.61 ** (± 0.19) | 5.11 ** (± 0.08) |

Figure 8:
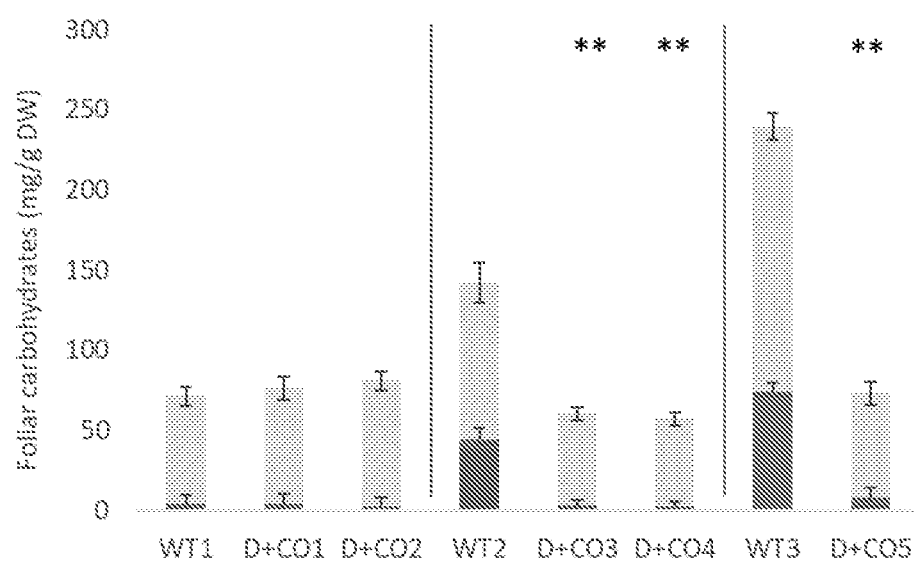
FIG. 8 shows stacked means (±SE) of high molecular weight carbohydrates (■) and low molecular weight carbohydrates ( ) in the leaves of five DGAT+CO transformed *Lolium perenne* lines and respective wild type controls. Matching genetic backgrounds are grouped together. n=10. **=statistically differs from WT, P<0.01.
Figure 11:
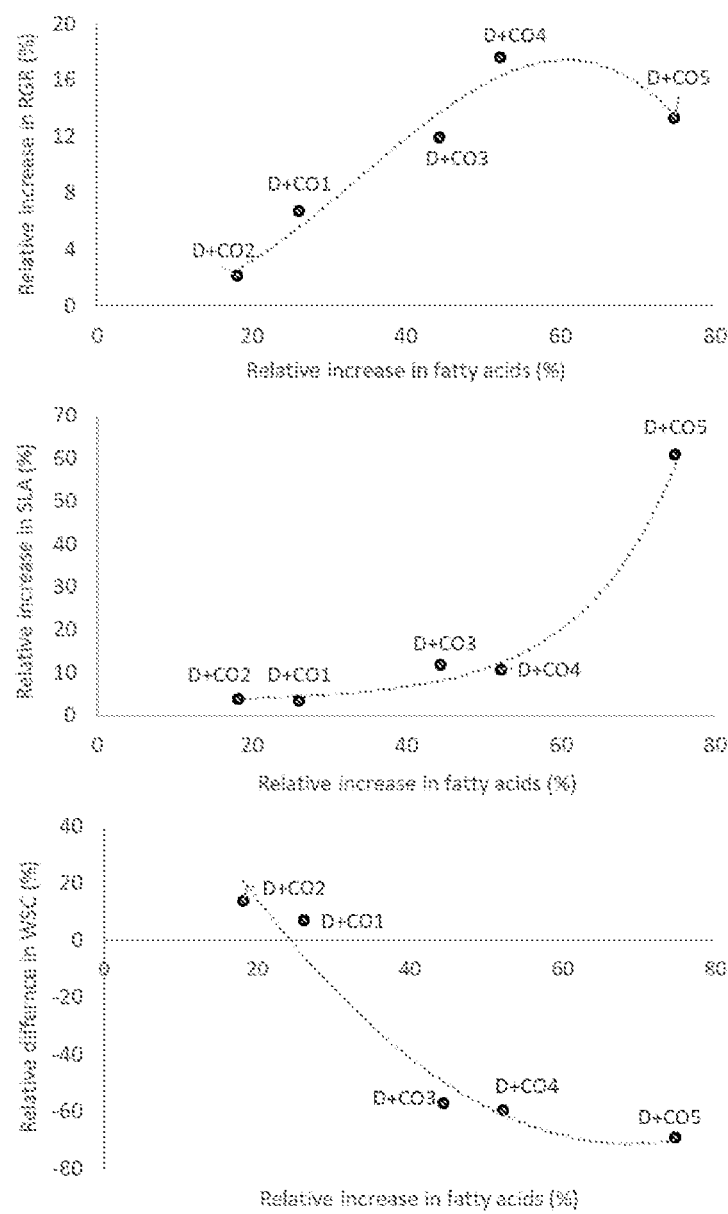
FIG. 11 shows relative increase in leaf fatty acids for each DGAT+cys-ole line, compared to respective WT, compared to the relative increase in relative growth rate (top), relative increase in SLA (middle) and relative difference in water soluble carbohydrates (bottom), to that of respective WT.

Low molecular weight carbohydrates (LMW) and high molecular weight carbohydrates (HMW) were significantly lower in DGAT+CO3, DGAT+CO4 and DGAT+CO5, compared to respective WT lines (FIG. 8). Collectively, this represented a reduction in total water-soluble carbohydrates of 57%, 59% and 69% for DGAT+CO3, DGAT+CO4 and DGAT+CO5 respectively, compared to respective WT controls (FIG. 8). In contrast, we found no statistical difference in LMW, HMW or total WSC between DGAT+CO1, DGAT+CO2 and their WT1 control (FIG. 8). The relative difference in WSC for each DGAT+CO line, compared to respective WT control, correlated negatively with the relative increase in total FA for each line, compared to respective WT control ($r^2=0.95$; $P=0.04$; FIG. 11) i.e. those DGAT+CO lines with the largest increase in leaf FA also displayed the largest reduction in leaf WSC. Both LMW and HMW carbohydrates were significantly lower for WT1, compared to both WT2 and WT3 (FIG. 8).

Growth, Photosynthesis and Chlorophyll

Figure 5:
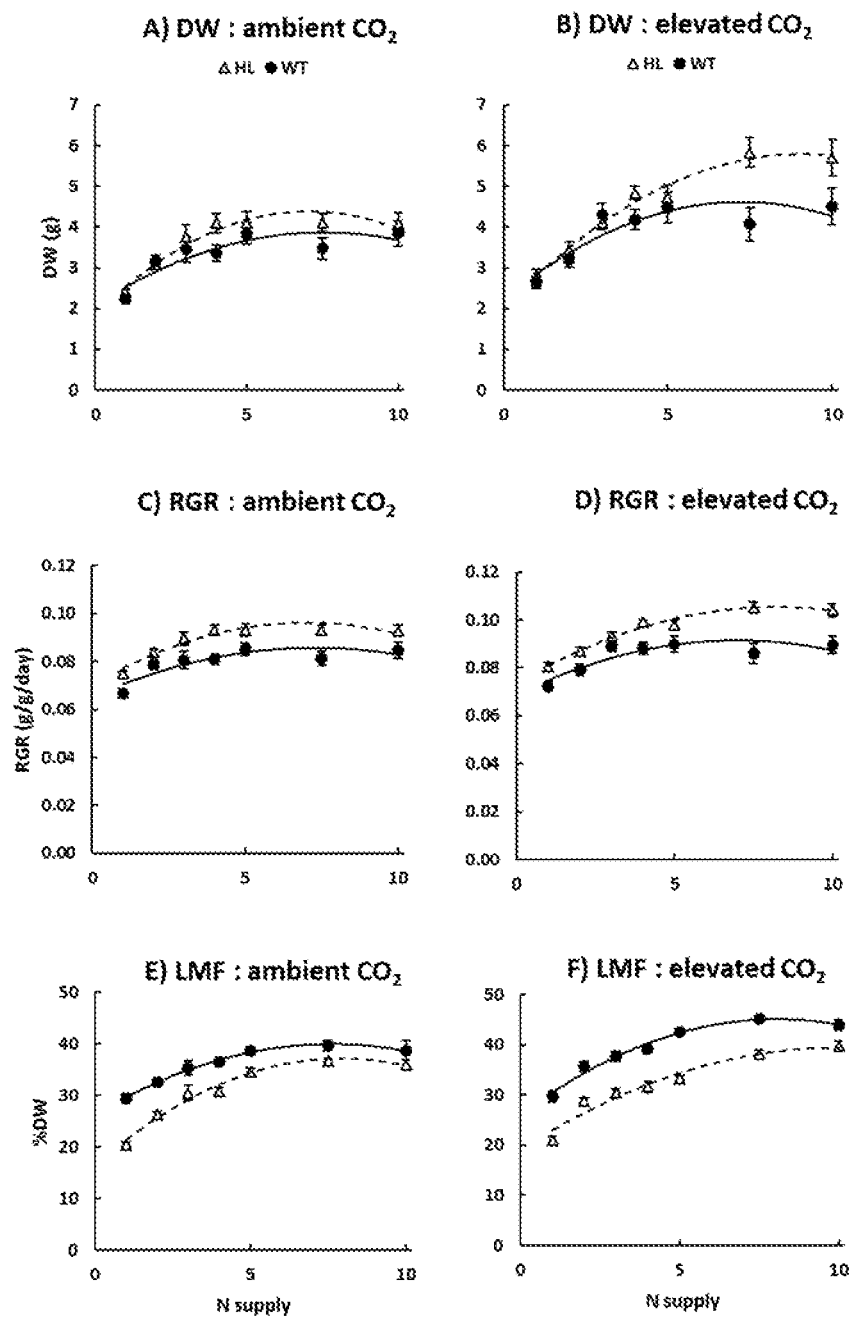
FIG. 5 shows growth parameters of a clonal cys-OLE/DGAT ryegrass transformant (HL; open triangles) and a wild type control (WT; closed circles) genotype. A) and B) Total plant DW, C) and D) relative growth rate (RGR), E) and F) the proportion of total plant DW allocated to leaves (LMF). Plants were regrown for 28-29 days after defoliation at 1-10 mM N supply at either ambient (400 ppm) or elevated CO2 (760 ppm). Data points represent raw averages for plants regrown under NO3− and NH4+ (n=10)±S.E.
Figure 9:
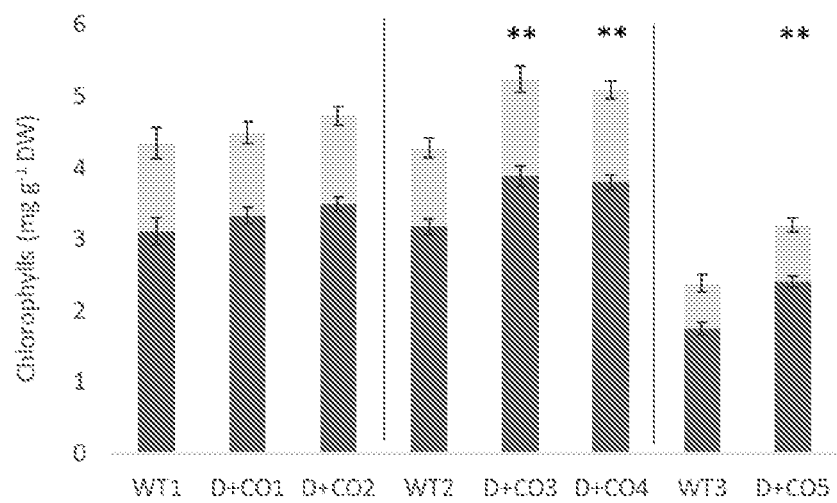
FIG. 9 shows stacked means (±SE) of chlorophyll a (■) and chlorophyll b ( ) in the leaves of five DGAT+CO transformed *Lolium perenne* lines and respective wild type controls. Matching genetic backgrounds are grouped together. n=10. **=statistically differs from WT,P<0.01.
Figure 10:
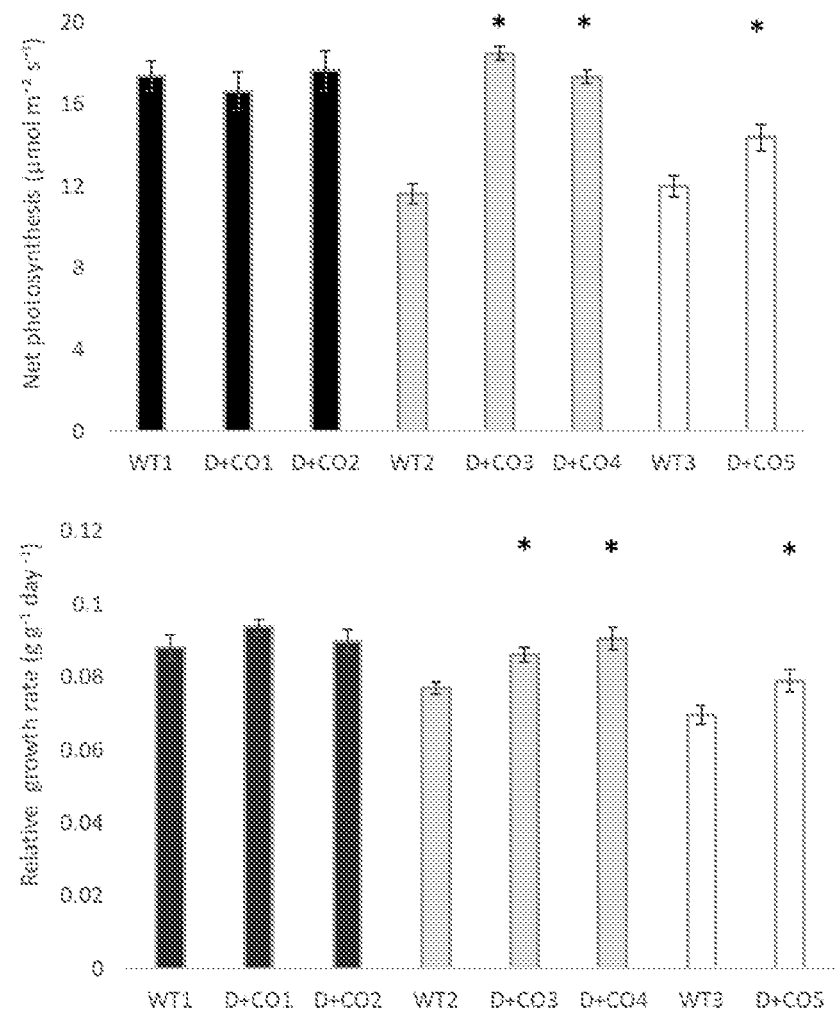
FIG. 10 shows net photosynthesis (above) and relative growth rate (below) for five DGAT+cys-ole lines and three WT lines. Means±SE. *, P=0.05. n=10. Matching genetic backgrounds are shaded together.

Of the five DGAT+cys-ole lines examined here, two (DGAT+CO1 and DGAT+CO2) showed no significant difference in gas exchange, chlorophyll or biomass, compared to their respective WT control (Table 8 below). In contrast, after six weeks' growth, DGAT+CO3, DGAT+CO4 and DGAT+CO5 were between 59%-82% larger than their respective WT controls and displayed a significant increase in leaf dry weight (DW), total shoot DW, root DW (Table 8 below) chlorophyll a and chlorophyll b (FIG. 9). Differences in establishment (i.e. growth in the three weeks following propagation) explain a proportion the total growth difference for these lines (Table 7 above), however, the relative growth rate between the post-establishment harvest (three weeks after propagation) and final harvest (six weeks after propagation) was also significantly higher for DGAT+CO3, DGAT+CO4 and DGAT+CO5, compared to respective controls (FIG. 10). The increase in relative growth rate for each line, compared to respective WT control, correlated positively with the percent increase in leaf fatty acids (FIG. 5), however this correlation was not statistically significant at the 5% level ($r^2=0.93$; $P=0.065$). Similarly, percent increase in fatty acids correlated positively with an increase in specific leaf area (SLA; FIG. 5; $r^2=0.99$; $P=0.01$) and while SLA was significantly higher for DGAT+CO5 compared to WT (Table 2), DGAT+CO4 and DGAT+CO5 SLA did not statistically differ from WT (Table 8 below).

TABLE 8

| | Leaf DW (g) | Root DW (g) | Shoot DW (g) | Total DW (g) | LA (cm2) | SLA | Amass (µmol kg$^{-1}$ DW s$^{-1}$) | gsw (mol m$^{-2}$ s$^{-1}$) | E (mol m$^{-2}$ s$^{-1}$) |
|---|---|---|---|---|---|---|---|---|---|
| WT1 | 1.6 (± 0.1) | 0.9 (± 0.06) | 2.8 (± 0.1) | 3.7 (± 0.1) | 444 (± 19) | 274 (± 8) | 475 (± 21) | 0.27 (± 0.01) | 2.1 (± 0.1) |
| DGAT + CO1 | 1.6 (± 0.04) | 0.7 * (± 0.03) | 2.7 (± 0.1) | 3.4 (± 0.1) | 451 (± 15) | 283 (± 9) | 468 (± 28) | 0.26 (± 0.02) | 2 (± 0.2) |
| DGAT + CO2 | 1.6 (± 0.05) | 0.9 (± 0.07) | 2.7 (± 0.1) | 3.6 (± 0.2) | 454 (± 11) | 284 (± 8) | 499 (± 29) | 0.28 (± 0.02) | 2.1 (± 0.2) |
| WT2 | 0.8 (± 0.03) | 0.4 (± 0.03) | 1.4 (± 0.1) | 1.9 (± 0.1) | 206 (± 15) | 260 (± 15) | 301 (± 20) | 0.15 (± 0.01) | 1.2 (± 0.1) |
| DGAT + CO3 | 1.2 ** (± 0.03) | 0.9 ** (± 0.05) | 2.4 ** (± 0.1) | 3.3 ** (± 0.1) | 359 ** (± 9) | 290 (± 5) | 536 ** (± 11) | 0.34 ** (± 0.01) | 2.5 ** (± 0.1) |
| DGAT + CO4 | 1.4 ** (± 0.1) | 0.9 ** (± 0.06) | 2.5 ** (± 0.1) | 3.4 ** (± 0.1) | 415 ** (± 19) | 287 (± 8) | 497 ** (± 13) | 0.3 ** (± 0.01) | 2.2 ** (± 0.1) |
| WT3 | 0.9 (± 0.1) | 0.5 (± 0.04) | 2.1 (± 0.1) | 2.5 (± 0.2) | 197 (± 17) | 213 (± 8) | 256 (± 17) | 0.2 (± 0.01) | 1.5 (± 0.1) |
| DGAT + CO5 | 1.3 * (± 0.1) | 0.8 ** (± 0.06) | 3.2 ** (± 0.2) | 4 ** (± 0.3) | 433 ** (± 31) | 343 ** (± 9) | 493 ** (± 27) | 0.2 (± 0.01) | 1.5 (± 0.1) |

Regardless, DGAT+CO3, DGAT+CO4 and DGAT+CO5 all displayed a significant increase in total leaf area, compared to respective WT controls, of 74%, 101% and 120% respectively (Table 8 above).

DGAT+CO3, DGAT+CO4 and DGAT+CO5 displayed a significant increase in net photosynthesis (FIG. 10) and $A_{mass}$ (Table 6 above), compared to respective WT lines. DGAT+CO3, DGAT+CO4 also displayed a significant increase in stomatal conductance and transpiration, compared to WT controls (Table 8 above), however, no statistical difference in stomatal conductance or transpiration, on a per leaf area basis, was detected for DGAT+CO5 compared to WT (Table 8 above).

The applicant has demonstrated the combination of DGAT+cysteine oleosin dramatically increased fatty acids in the leaves of Lolium perenne and coincided with several morphological, physiological and biochemical changes in the plant. FA correlated positively with DGAT expression and for those lines with the largest increase in fatty acids, we identified a significant reduction in leaf sugar, both LMW and HMW carbohydrates, and a significant increase in A, $A_{mass}$ and chlorophyll. For DGAT+CO5, the line with the largest relative increase in fatty acids, we also identified a significant increase in specific leaf area. Collectively, the applicant shown that the elevation of fatty acids in leaves, at the expense of leaf sugar, coincides with traits that increase carbon assimilation (primarily increased SLA and photosynthesis) and subsequently, increase relative growth rate. DGAT+CO ryegrass presents a novel opportunity to increase the quality and quantity of forage production and examine the regulation of photosynthesis and other traits related to carbon capture.

The applicant has identified a strong negative correlation between relative fatty acid accumulation and water-soluble carbohydrates. This observation is consistent with Vanhercke et al. (2019), who similarly identified a trade-off in carbon allocation between lipids and sugar. Regulation of photosynthetic capacity is determined by, among other things, the availability of carbon (source strength), to the demand for carbon (sink strength) (Paul and Foyer, 2001; Arp, 1991; Ainsworth et al 2004), and sugar plays a key role in signalling this relationship (Paul and Driscoll, 2004; Iglesias et al, 2002; Roitsch, 1999; Ainsworth and Bush, 2011; Rierio et al, 2017). Here, we observed distinct morphological and physiological changes (e.g. increased chlorophyll, photosynthesis and specific leaf area) following DGAT+CO transformation, but only in those lines that displayed the largest reduction in leaf sugar. The applicant suggests that a reduction in leaf sugar, as a result of an introduced lipid carbon sink, is directly responsible for inducing those physiological and morphological acclimations (e.g. increased photosynthesis and specific leaf area), that improved carbon assimilation and subsequent growth rate. As such according to the present invention, the correlation between reduced WSC is a more robust way of determining the influence on $CO_2$ assimilation as compared to measuring either accumulation of the cysteine oleosin protein or the accumulation of additional lipids within the leaf both of which have indirect influences on photosynthesis.

REFERENCES

Abell et al., (2004). Plant J., 37:461-70.
Ainsworth and Rogers (2007). Plant, cell & environment, 30 (3), 258-270.
Ainsworth and Bush (2011). Plant Physiology 155, 64-69, doi: 10.1104/pp.110.167684 (2011).
Ainsworth et al., (2003). Plant, cell & environment, 26 (5), 705-714.
Ainsworth et al., (2004). Agricultural and forest meteorology, 122 (1-2), 85-94.
Altschul et al., (1997) Nucleic Acids Res. 25:3389-3402,
Andrews et al., (1989). Annals of applied biology, 114 (1), 195-204.
Andrews et al., (2013). Annals of applied biology, 163 (2), 174-199.
Andrews et al., (2018). Journal of Experimental Botany, 70 (2), 683-690.
Andrianov et al., (2010). Plant Biotechnol J. 8 (3): 277-87.
Arp (1991). Plant, cell & environment, 14 (8), 869-875.
Ausubel et al., (1987) Current Protocols in Molecular Biology, Greene Publishing Bairoch
Bao et al, (2000) Plant J. 22 (1): 39-50.
Bari et al., (2009). J. Exp. Bot. 55:623-630.
Beechey-Gradwell et al., (2018). Journal of New Zealand Grasslands, 80, 219-224.
Bellasio et al., (2014). Journal of Experimental Botany, 65 (13), 3769-3779.
Birch (1997) Ann Rev Plant Phys Plant Mol Biol, 48, 297
Bloom (2015). Current opinion in plant biology, 25, 10-16.
Bock & Khan (2004). Trends in Biotech. 22:311-318.
Bolton and McCarthy (1962) PNAS 84:1390
Bouvier-Nave et al., (2000) Eur. J. Biochem. 267, 85-96.
Bowie et al., (1990). Science 247, 1306
Browse et al., (1986). Analytical Biochemistry 152, 141-145, doi.org/10.1016/0003-2697 (86) 90132-6.
Bryan et al., (2007) Modification of fatty acid biosynthesis. US20070118927.
Bucher (1994), Nucleic Acids Res. 22, 3583
Capuano et al., (2007). Biotechnol Adv. 25:203-206.
Causton and Venus (1982). The Mathematical Gazette, 66:175
DOI: doi.org/10.2307/3617784
Chen et al., (1999). Plant Cell Physiol., 40:1079-1086.
Chiang et al., (2005). J Agric Food Chem 53:4799-804.
Chiang et al., (2007). Protein Expr Purif. 52:14-8.
Chisti (2007). Biotech. Adv. 25:294-306.
Colman et al., (1974). Plant Phys, 53:395-397.
Cookson et al., (2009). Improvements in and relating to oil production. PCT/NZ2008/000085 WO/2008/130248
Dahlqvist et al., (2000). Proc Natl Acad Sci USA. 97, 6487-6492.
Deckers et al., (2003). U.S. Pat. No. 6,582,710
Demeyer and Doreau, (1999). Proc Nutr Soc. 58 (3): 593-607.
Deutscher (1990) Ed, Methods in Enzymology, Vol. 182, Guide to Protein Purification
Draper et al., 1988, Plant Genetic Transformation and Gene Expression. A Laboratory Manual. Blackwell Sci. Pub. Oxford, p. 365
Durrett et al., (2011). Plant biotechnology journal, 9 (8), 874-883.
Falquet et al., 2002, Nucleic Acids Res. 30, 235
Feeney and Punja (2003). In vitro Cellular and Devlopmental Biology—Plant. 39:578-585
Feng and Doolittle, 1987, J. Mol. Evol. 25, 351
Firkins et al., (2006). J Dairy Sci. 89 Suppl 1: E31-51. Review. Greenspan.
Fischer et al., (1997). Plant, cell & environment, 20 (7), 945-952.
Frandsen et al., (2001). Physiologia Plantarum, 112:301-307.

Frohman (1993). Methods Enzymol. 218:340-56
Galun and Breiman (1997). Transgenic Plants. Imperial College Press, London
Gelvin et al., 1993, Plant Molecular Biol. Manual. Kluwer Acad. Pub. Dordrecht
Giesen et al., Nucleic Acids Res. 1998 Nov. 1; 26 (21): 5004-6
Giordano et al., (2005). Ann. Rev. Pl. Biol. 56:99-131.
Grimberg et al., (2015). BMC plant biology, 15 (1), 192.
Guo et al., (2006). Functional Plant Biology, 33 (11), 1045-1053.
Guo et al., (2007). Plant Biology, 9 (1), 21-29.
Halford & Hardie (1998). Plant Mol Biol. 37:735-48. Review
Harada et al., (2002). Oleosin/phospholipid complex and process for producing the same. WO/2002/026788.
Hedge and Hofreiter (1962). In: Methods in Carbohydrate Chemistry (eds R. L. Whistler & J. N. B. Miller) 356-378 (Academic Press).
Hellens et al., (2000). Plant Mol Biol 42:819-32
Hellens et al., (2005). Plant Meth 1:13
Herrera-Estrella et al., (1993). Nature 303, 209
Hofmann et al., (1999). Nucleic Acids Res. 27, 215
Hou et al., (2003). J Dairy Sci; 86:424-8.
Huang (1992). Ann. Rev. Plant Physiol. Plant Mol. Biol. 43:177-200.
Huang, X. (1994) Computer Applications in the Biosciences 10, 227-235
Iglesias et al., (2002). Physiologia Plantarum 116, 563-572, doi: doi: 10.1034/j.1399-3054.2002.1160416.x.
Isopp et al., (2000). Plant, cell & environment, 23 (6), 597-607.
Jeanmougin et al., (1998) Trends Biochem. Sci. 23, 403-5.
Jenkins and Bridges (2007). Eur. J. Lipid Sci. Technol. 109:778-789.
Jenkins and McGuire (2006). J Dairy Sci. 89 (4): 1302-10. Review.
Kaup et al., (2002) Plant Physiol. 129 (4): 1616-26.
Kebeish et al., (2007). Nature Biotech, 25:593-599.
Kebeish et al., (2007). Nature biotechnology, 25 (5), 593.
Kelly et al., (2013). Plant physiology, 162 (3), 1282-1289.
Kozaki & Takeba (1996). Nature, 384:557-560.
Kyte and Doolitle (1982) J. Mol. Biol. 157:105-132
Lanfranco L. (2003). Riv Biol. 96 (1): 31-54.
Lardizabal et al., (2001). J.B.C. 276, 38862-38869.
Lee et al., (2010). PLOS One, 5 (8), e12306.
Leprince et al., (1998). Planta 204 109-119.
Li and Sheen (2016). Current opinion in plant biology, 33, 116-125.
Li Shao et al., (2015). Frontiers in plant science, 6, 1015.
Lichtenthaler (1987). Methods in Enzymology 148, 350-382, dx.doi.org/10.1016/0076-6879 (87) 48036-1.
Lin and Tzen. (2004). Plant Physiology and Biochemistry. 42:601-608.
Lock and Bauman (2004). Lipids. 39 (12): 1197-206. Review.
Loer and Herman (1993). Plant Physiol. 101 (3): 993-998.
Long et al., (2006). Plant, cell & environment, 29 (3), 315-330.
Mayer and Fowler (1985). J Cell Biol. 100 (3): 965-73.
Mekhedov et al., (2000). Plant Physiol. 122 (2): 389-402).
Mullis et al., Eds. 1994 The Polymerase Chain Reaction, Birkhauser
Murphy (1993). Prog. Lipid Res. 32:247-280.
Nakamura et al., (2005). Can. J. Bot. 83:820-833.
Needleman and Wunsch, (1970) J. Mol. Biol. 48, 443-453
Nielsen et al., Science. (1991) 254 (5037): 1497-500
Notredame et al., (2000). J. Mol. Biol. 302:205-217
Ohlrogge and Jaworski (1997). Annu Rev Plant Physiol Plant Mol Biol. 48:109-136.
Onoda et al., (2017). New phytologist, 214 (4), 1447-1463.
Papapostolou and Howorka (2009). Mol Biosyst. 5 (7): 723-32. Review.
Parry et al., (2003). J. Exp. Bot., 54:1321-1333.
Paul and Driscoll (1997). Plant, Cell & Environment 20, 110-116, doi: doi: 10.1046/j.1365-3040.1997.d01-17.x.
Paul and Foyer (2001). Journal of Experimental Botany, 52 (360), 1383-1400.
Paz et al., (2004). Euphytica, 136:167-179
Peng (2004). Development and applications of artificial sesame oil body. Ph.D. Dissertation. National ChunHsing University Graduate Institute of Biotechnology. Taichung, Taiwan.
Peng et al., (2004). J Biotechnol 2004; 111:51-7.
Peng et al., (2006). Stability enhancement of native and artificial oil bodies by genipin crosslink. Taiwan patent I250466.
Peterhansel et al., (2008). Photochem. Photobiol. 84:1317-1323.
Poorter (1989a). Physiologia *plantarum*, 75 (2), 237-244.
Poorter (1989b). Causes and consequences of variation in growth rate and productivity of higher plants, 24, 45-68.
Poorter et al., (2009). New phytologist, 182 (3), 565-588.
Poorter et al., (2012). Functional Plant Biology, 39 (11), 839-850.
Potrykus and Spangenburg (1995). Gene Transfer to Plants. Springer-Verlag, Berlin
Ribeiro et al., (2017). Journal of Plant Physiology 208, 61-69, doi.org/10.1016/j.jplph.2016.11.005.
Roberts et al., (2008). The Open Biotechnology Journal 2:13-21.
Roberts et al., (2011). Modified neutral lipids encapsulating proteins and uses thereof. WO/2011/053169.
Roberts et al., (2013). Methods for Increasing $CO_2$ Assimilation And Oil Production In Photosynthetic Organisms. WO2013022053A1
Roitsch (1999). Current Opinion in Plant Biology 2, 198-206, doi.org/10.1016/S1369-5266 (99) 80036-3.
Roux et al., (2004). J Agric Food Chem. 52 (16): 5245-9.
Ruiz-Vera et al., (2017). Plant Science, 8, 998.
Saha et al., (2006). Plant Physiol. 141 (4): 1533-43.
Sambrook et al., Eds, 1987, Molecular Cloning, A Laboratory Manual, 2nd Ed. Cold Spring Harbor Press
Sarmiento et al., (1997). Plant J. 11 (4): 783-96.
Schrott (1995) In: Gene Transfer to Plants (Potrykus, T., Spangenberg. Eds) Springer Verlag. Berline, pp. 325-336
Schwender (2004). Nature, 432 (7018), 779.
Scott et al., (2007). Polyoleosins. WO2007045019.
Sharkey (2016). Plant, cell & environment, 39 (6), 1161-1163.
Sharkey et al., (2007). Plant, cell & environment, 30 (9), 1035-1040.
Shimada et al., (2008). Plant J. 55 (5): 798-809.
Shockey et al., (2006). Plant Cell., 18, 2294-2313.
Siloto et al., (2006). Plant Cell. 18 (8): 1961-74.
Singh et al., (2016). Journal of Plant Research, 129 (2), 285-293.
Slack et al., (1980). Biochem J. 190 (3): 551-561.
Slocombe et al., (2009). Plant Biotechnol J. 7 (7): 694-703.
Smith and Stitt (2007). Plant, cell & environment, 30 (9), 1126-1149.
Stahl et al., (2004). Plant Physiology, 135:1324-1335.

Stewart et al., (1969), In: Solid-Phase Peptide Synthesis, WH Freeman Co, San Francisco California
Tadege et al., (2005). Trends Plant Sci. 10 (5): 229-35.
Temme et al., (2017). Perspectives in Plant Ecology, Evolution and Systematics, 29, 41-50.
Thompson et al., (1994) Nucleic Acids Research, 22:4673-4680
Ting et al., (1997). J Biol Chem., 272:3699-3706.
Tolbert (1997). Ann. Rev. Pl. Phys. Pl. Molec. Biol. 48:1-25.
Tolbert et al., (1983). Pl. Physiol. 72:1075-1083.
Triglia et al., 1998, Nucleic Acids Res 16, 8186
Turner et al., (2001). Journal of Plant Physiology, 158 (7), 891-897.
Tzen et al., (1992). J. Biol. Chem. 267:15626-34
Tzen et al., (1997). J Biochem. 121 (4): 762-8.
Tzen et al., (2003). Adv Plant Physiol., 6:93-104.
Vanhercke et al., (2014). Biocatalysis and Agricultural Biotechnology, 3 (1), 75-80.
Vanhercke et al., (2017). Metabolic engineering, 39, 237-246.
Vanhercke et al., (2019) Plant Biotechnology Journal 17, 220-232, doi: 10.1111/pbi.12959.
Vanhercke et al., (2019). Progress in lipid research.
Voisey et al., (1994). Plant Cell Reports 13:309 314.
White et al., (2015). Journal of Experimental Botany, 67 (1), 31-45.
Winichayakul et al., (2008). Proc NZ Grassland Assoc. 70:211-216.
Winichayakul et al., (2013). Plant physiology, 162 (2), 626-639.
Wong et al., (1979). Nature, 282 (5737), 424.
Wu et al., (2019). Nature plants, 5 (4), 380.
Xu and Shanklin (2016). Annual review of plant biology, 67, 179-206.
Xu et al., (2005). Plant Cell. 17 (11): 3094-110.
Yu et al., (2018). Plant physiology, 178 (1), 118-129.
Zeng et al., (2004). Plant Cell Reports, 22:478-482.
Zhai et al., (2017). Plant physiology, 175 (2), 696-707.
Zhai et al., (2018). The Plant Cell, 30 (10), 2616-2627.
Zou et al., (1999). Plant J. 19, 645-653.
Zou et al., (2008). Plant Biotech. J. 6 (8): 799-818.

SUMMARY OF SEQUENCE LISTING

| SEQ ID NO: | Type | SPECIES | COMMENTS |
|---|---|---|---|
| 1 | Polypeptide | S. indicum | AAG23840 |
| 2 | Polypeptide | S. indicum | AAB58402 |
| 3 | Polypeptide | A. thaliana | CAA44225 |
| 4 | Polypeptide | A. thaliana | AAZ23930 |
| 5 | Polypeptide | H. annuus | CAA44224.1 |
| 6 | Polypeptide | B. napus | CAA57545.1 |
| 7 | Polypeptide | Z. mays | NP_001147032.1 |
| 8 | Polypeptide | O. sativa | AAL40177.1 |
| 9 | Polypeptide | B. oleracea | AAD24547.1 |
| 10 | Polypeptide | C. arabica | AAY14574.1 |
| 11 | Polypeptide | B. oleraceae | CAA65272.1 |
| 12 | Polypeptide | S. indicum | AAD42942 |
| 13 | Polynucleotide | S. indicum | AF302907 |
| 14 | Polynucleotide | S. indicum | U97700 |
| 15 | Polynucleotide | A. thaliana | X62353 |
| 16 | Polynucleotide | A. thaliana | BT023738 |
| 17 | Polynucleotide | H. annuus | X62352.1 |
| 18 | Polynucleotide | B. napus | X82020.1 |
| 19 | Polynucleotide | Z. mays | NM_001153560.1 |
| 20 | Polynucleotide | O. sativa | AAL40177.1 |
| 21 | Polynucleotide | B. oleracea | AF117126.1 |
| 22 | Polynucleotide | C. arabica | AY928084.1 |
| 23 | Polynucleotide | B. oleraceae | X96409 |
| 24 | Polynucleotide | S. indicum | AF091840 |
| 25 | Polypeptide | A. thaliana | NP_179535 |
| 26 | Polypeptide | T. majus | AAM03340 |
| 27 | Polypeptide | Z. mays | ABV91586 |
| 28 | Polypeptide | A. thaliana | NP_566952 |
| 29 | Polypeptide | B. napus | AC090187 |
| 30 | Polypeptide | A. hypogaea | AAX62735 |
| 31 | Polypeptide | A. thaliana | NP_196868 |
| 32 | Polypeptide | R. communis | XP_002521350 |
| 33 | Polynucleotide | A. thaliana | NM_127503 |
| 34 | Polynucleotide | T. majus | AY084052 |
| 35 | Polynucleotide | Z. mays | EU039830 |
| 36 | Polynucleotide | A. thaliana | NM_115011 |
| 37 | Polynucleotide | B. napus | FJ858270 |
| 38 | Polynucleotide | A. hypogaea | AY875644 |
| 39 | Polynucleotide | A. thaliana | NM_121367 |
| 40 | Polynucleotide | R. communis | XM_002521304 |
| 41 | Polynucleotide | O. sativa | AY583764 |
| 42 | Polynucleotide | O. sativa | AP014965 |
| 43 | Polynucleotide | P. vulgaris | AF028707 |
| 44 | Polynucleotide | P. sativum | M21356; M27973 |
| 45 | Polynucleotide | P. sativum | M64619 |
| 46 | Polynucleotide | G. max | D16248 |
| 47 | Polynucleotide | A. thaliana | L05399 |
| 48 | Polynucleotide | Cauliflower mosaic virus | V00141; J02048 |
| 49 | Polypeptide | S. indicum | Modified oleosin |
| 50 | Polypeptide | T. majus | DGAT1 |
| 51 | Polypeptide | Synthetic construct | V5 epitope tag |

What is claimed is:

1. A method for reducing water-soluble carbohydrates (WSC) in a photosynthetic cell or plant, the method comprising the steps of:
   (a) genetically modifying the photosynthetic cell or plant to express:
      a modified oleosin including at least one artificially introduced cysteine, wherein
      (i) the cysteine is introduced into at least one of the N-terminal hydrophilic region of the oleosin and the C-terminal hydrophilic region of the oleosin; and
      (ii) at least one diacylglycerol acyltransferase-1 (DGAT 1); and
   (b) measuring WSC amounts in the photosynthetic cell or plant, and
   (c) selecting a photosynthetic cell or plant with reduced WSC relative to that in a control photosynthetic cell or plant.

2. The method of claim 1, in which measurement of a reduction in WSC is indicative of increased $CO_2$ assimilation in the photosynthetic cell or plant.

3. A method for producing a photosynthetic cell or plant with increased $CO_2$ assimilation, the method comprising:
   (a) modifying the photosynthetic cell or plant to reduce water-soluble carbohydrates (WSC) by genetically modifying the photosynthetic cell or plant to express:
      (i) a modified oleosin comprising at least one artificially introduced cysteine to reduce WSC, wherein
         (i) the cysteine is introduced into at least one of the N-terminal hydrophilic region of the oleosin and the C-terminal hydrophilic region of the oleosin; and
      (ii) at least one diacylglycerol acyltransferase-1 (DGAT1); and
   (b) measuring WSC amounts in the photosynthetic cell or plant, and
   (c) selecting a photosynthetic cell or plant with increased $CO_2$ assimilation on the basis of measuring the reduction in WSC relative to that in a control photosynthetic cell or plant.

4. The method of claim 3, in which measurement of a reduction in WSC is indicative of increased $CO_2$ assimilation in the photosynthetic cell or plant.

5. The method of claim 1, wherein the modified oleosin includes at least three artificially introduced cysteines in the N-terminal hydrophilic region and at least three artificially introduced cysteines in the C-terminal hydrophilic region.

6. The method of claim 3, wherein the modified oleosin includes at least three artificially introduced cysteines in the N-terminal hydrophilic region and at least three artificially introduced cysteines in the C-terminal hydrophilic region.

7. The method of claim 1, wherein the cysteines are distributed substantially evenly over the N-terminal and C-terminal hydrophilic regions of the oleosin.

8. The method of claim 3, wherein the cysteines are distributed substantially evenly over the N-terminal and C-terminal hydrophilic regions of the oleosin.

9. The method of claim 1, wherein the modified oleosin includes up to seven (7) cysteines in the N-terminal hydrophilic region, and up to seven (7) cysteines in the C-terminal hydrophilic region.

10. The method of claim 3, wherein the modified oleosin includes up to seven (7) cysteines in the N-terminal hydrophilic region, and up to seven (7) cysteines in the C-terminal hydrophilic region.

* * * * *

UNITED STATES PATENT AND TRADEMARK OFFICE
CERTIFICATE OF CORRECTION

| | | |
|---|---|---|
| PATENT NO. | : 12,275,945 B2 | Page 1 of 1 |
| APPLICATION NO. | : 17/755168 | |
| DATED | : April 15, 2025 | |
| INVENTOR(S) | : Nicholas John Roberts et al. | |

It is certified that error appears in the above-identified patent and that said Letters Patent is hereby corrected as shown below:

In the Claims

In Claim 1, Column 143, Line 38:
Insert: --(i)-- before "a modified oleosin including at least one artificially"

In Claim 1, Column 143, Line 40:
Delete: "(i)"

Signed and Sealed this
Twenty-fourth Day of June, 2025

Coke Morgan Stewart
*Acting Director of the United States Patent and Trademark Office*

SEQUENCE LISTING

```
<160> NUMBER OF SEQ ID NOS: 51

<210> SEQ ID NO 1
<211> LENGTH: 166
<212> TYPE: PRT
<213> ORGANISM: S. indicum

<400> SEQUENCE: 1

Met Ala Asp Arg Asp Arg Pro His Pro His Gln Ile Gln Val His Pro
1               5                   10                  15

Gln His Pro His Arg Tyr Glu Gly Gly Val Lys Ser Leu Leu Pro Gln
            20                  25                  30

Lys Gly Pro Ser Thr Thr Gln Ile Leu Ala Ile Ile Thr Leu Leu Pro
```

```
                35                  40                  45
Ile Ser Gly Thr Leu Leu Cys Leu Ala Gly Ile Thr Leu Val Gly Thr
 50                  55                  60

Leu Ile Gly Leu Ala Val Ala Thr Pro Val Phe Val Ile Phe Ser Pro
 65                  70                  75                  80

Val Leu Val Pro Ala Ala Ile Leu Ile Ala Gly Ala Val Thr Ala Phe
                 85                  90                  95

Leu Thr Ser Gly Ala Phe Gly Leu Thr Gly Leu Ser Ser Leu Ser Trp
                100                 105                 110

Val Leu Asn Ser Phe Arg Arg Ala Thr Gly Gln Gly Pro Leu Glu Tyr
                115                 120                 125

Ala Lys Arg Gly Val Gln Glu Gly Thr Leu Tyr Val Gly Glu Lys Thr
                130                 135                 140

Lys Gln Ala Gly Glu Ala Ile Lys Ser Thr Ala Lys Glu Gly Gly Arg
145                 150                 155                 160

Glu Gly Thr Ala Arg Thr
                165

<210> SEQ ID NO 2
<211> LENGTH: 144
<212> TYPE: PRT
<213> ORGANISM: S. indicum

<400> SEQUENCE: 2

Met Ala Asp Glu Pro His Asp Gln Arg Pro Thr Asp Val Ile Lys Ser
1                   5                  10                  15

Tyr Leu Pro Glu Lys Gly Pro Ser Thr Ser Gln Val Leu Ala Val Val
                 20                  25                  30

Thr Leu Phe Pro Leu Gly Ala Val Leu Leu Cys Leu Ala Gly Leu Ile
                 35                  40                  45

Leu Thr Gly Thr Ile Ile Gly Leu Ala Val Ala Thr Pro Leu Phe Val
 50                  55                  60

Ile Phe Ser Pro Ile Leu Val Pro Ala Ala Leu Thr Ile Ala Leu Ala
 65                  70                  75                  80

Val Thr Gly Phe Leu Thr Ser Gly Ala Phe Gly Ile Thr Ala Leu Ser
                 85                  90                  95

Ser Ile Ser Trp Leu Leu Asn Tyr Val Arg Arg Met Arg Gly Ser Leu
                100                 105                 110

Pro Glu Gln Leu Asp His Ala Arg Arg Val Gln Glu Thr Val Gly
                115                 120                 125

Gln Lys Thr Arg Glu Ala Gly Gln Arg Ser Gln Asp Val Ile Arg Pro
130                 135                 140

<210> SEQ ID NO 3
<211> LENGTH: 173
<212> TYPE: PRT
<213> ORGANISM: A. thaliana

<400> SEQUENCE: 3

Met Ala Asp Thr Ala Arg Gly Thr His His Asp Ile Ile Gly Arg Asp
1                   5                  10                  15

Gln Tyr Pro Met Met Gly Arg Asp Arg Asp Gln Tyr Gln Met Ser Gly
                 20                  25                  30

Arg Gly Ser Asp Tyr Ser Lys Ser Arg Gln Ile Ala Lys Ala Ala Thr
                 35                  40                  45

Ala Val Thr Ala Gly Gly Ser Leu Leu Val Leu Ser Ser Leu Thr Leu
```

```
Val Gly Thr Val Ile Ala Leu Thr Val Ala Thr Pro Leu Leu Val Ile
 65                  70                  75                  80

Phe Ser Pro Ile Leu Val Pro Ala Leu Ile Thr Val Ala Leu Leu Ile
                 85                  90                  95

Thr Gly Phe Leu Ser Ser Gly Gly Phe Gly Ile Ala Ala Ile Thr Val
            100                 105                 110

Phe Ser Trp Ile Tyr Lys Tyr Ala Thr Gly Glu His Pro Gln Gly Ser
                115                 120                 125

Asp Lys Leu Asp Ser Ala Arg Met Lys Leu Gly Ser Lys Ala Gln Asp
            130                 135                 140

Leu Lys Asp Arg Ala Gln Tyr Tyr Gly Gln Gln His Thr Gly Gly Glu
145                 150                 155                 160

His Asp Arg Asp Arg Thr Arg Gly Gly Gln His Thr Thr
                165                 170
```

<210> SEQ ID NO 4
<211> LENGTH: 149
<212> TYPE: PRT
<213> ORGANISM: A. thaliana

<400> SEQUENCE: 4

```
Met Ala Asp His Gln Gln His Gln Gln Gln Gln Gln Pro Ile Met Arg
  1               5                  10                  15

Ser Leu His Glu Ser Ser Pro Ser Thr Arg Gln Ile Val Arg Phe Val
                 20                  25                  30

Thr Ala Ala Thr Ile Gly Leu Ser Leu Leu Val Leu Ser Gly Leu Thr
             35                  40                  45

Leu Thr Gly Thr Val Ile Gly Leu Ile Val Ala Thr Pro Leu Met Val
 50                  55                  60

Leu Phe Ser Pro Val Leu Val Pro Ala Val Ile Thr Ile Gly Leu Leu
 65                  70                  75                  80

Thr Met Gly Phe Leu Phe Ser Gly Gly Cys Gly Val Ala Ala Ala Thr
                 85                  90                  95

Ala Leu Thr Trp Ile Tyr Lys Tyr Val Thr Gly Lys His Pro Met Gly
            100                 105                 110

Ala Asp Lys Val Asp Tyr Ala Arg Met Arg Ile Ala Glu Lys Ala Lys
                115                 120                 125

Glu Leu Gly His Tyr Thr His Ser Gln Pro Gln Gln Thr His Gln Thr
            130                 135                 140

Thr Thr Thr Thr His
145
```

<210> SEQ ID NO 5
<211> LENGTH: 181
<212> TYPE: PRT
<213> ORGANISM: H. annuus

<400> SEQUENCE: 5

```
Thr Thr Thr Thr Tyr Asp Arg His Phe Thr Thr Thr Gln Pro His Tyr
  1               5                  10                  15

Arg Gln Asp Asp Arg Ser Arg Tyr Asp Gln Gln Thr His Ser Gln Ser
                 20                  25                  30

Thr Ser Arg Thr Leu Ala Ile Ile Ala Leu Leu Pro Val Gly Gly Ile
             35                  40                  45

Leu Leu Gly Leu Ala Ala Leu Thr Phe Ile Gly Thr Leu Ile Gly Leu
```

```
                50                  55                  60
Ala Leu Ala Thr Pro Leu Phe Val Ile Phe Ser Pro Ile Ile Val Pro
 65                  70                  75                  80

Ala Val Leu Thr Ile Gly Leu Ala Val Thr Gly Phe Leu Ala Ser Gly
                 85                  90                  95

Thr Phe Gly Leu Thr Gly Leu Ser Ser Leu Ser Tyr Leu Phe Asn Met
                100                 105                 110

Val Arg Gln Thr Ala Gly Ser Val Pro Glu Ser Leu Asp Tyr Val Lys
            115                 120                 125

Gly Thr Leu Gln Asp Ala Gly Glu Tyr Ala Gly Gln Lys Thr Lys Asp
        130                 135                 140

Phe Gly Gln Lys Ile Gln Ser Thr Ala His Glu Met Gly Asp Gln Gly
145                 150                 155                 160

Gln Val Gly Val His Ala Gln Val Gly Gly Lys Glu Gly Arg Lys
                165                 170                 175

Ser Gly Asp Arg Thr
            180

<210> SEQ ID NO 6
<211> LENGTH: 165
<212> TYPE: PRT
<213> ORGANISM: B. napus

<400> SEQUENCE: 6

Met Gly Ile Leu Arg Lys Lys His Glu Arg Lys Pro Ser Phe Lys
 1               5                  10                  15

Ser Val Leu Thr Ala Ile Leu Ala Thr His Ala Ala Thr Phe Leu Leu
                 20                  25                  30

Leu Ile Ala Gly Val Ser Leu Ala Gly Thr Ala Ala Ala Phe Ile Ala
             35                  40                  45

Thr Met Pro Leu Phe Val Val Phe Ser Pro Ile Leu Val Pro Ala Gly
         50                  55                  60

Ile Thr Thr Gly Leu Leu Thr Thr Gly Leu Ala Ala Ala Gly Gly Ala
 65                  70                  75                  80

Gly Ala Thr Ala Val Thr Ile Ile Leu Trp Leu Tyr Lys Arg Ala Thr
                 85                  90                  95

Gly Lys Ala Pro Pro Lys Val Leu Glu Lys Val Leu Lys Lys Ile Ile
                100                 105                 110

Pro Gly Ala Ala Ala Ala Pro Ala Ala Ala Pro Gly Ala Ala Pro Ala
            115                 120                 125

Ala Ala Pro Ala Ala Ala Pro Ala Val Ala Pro Ala Ala Ala Pro Ala
        130                 135                 140

Ala Ala Pro Ala Pro Lys Pro Ala Ala Pro Pro Ala Pro Lys Pro Ala
145                 150                 155                 160

Ala Ala Pro Ser Ile
                165

<210> SEQ ID NO 7
<211> LENGTH: 186
<212> TYPE: PRT
<213> ORGANISM: Z. mays

<400> SEQUENCE: 7

Met Ala Asp Arg Asp Arg Ser Gly Ile Tyr Gly Gly Ala His Ala Thr
 1               5                  10                  15

Tyr Gly Gln Gln Gln Gln Gln Gly Gly Gly Gly Arg Pro Met Gly Glu
```

```
                20                  25                  30

Gln Val Lys Gly Met Leu His Asp Lys Gly Pro Thr Ala Ser Gln Ala
            35                  40                  45

Leu Thr Val Ala Thr Leu Phe Pro Leu Gly Leu Leu Val Leu
        50                  55                  60

Ser Gly Leu Ala Leu Thr Ala Ser Val Val Gly Leu Ala Val Ala Thr
 65                  70                  75                  80

Pro Val Phe Leu Ile Phe Ser Pro Val Leu Val Pro Ala Ala Leu Leu
                    85                  90                  95

Ile Gly Thr Ala Val Met Gly Phe Leu Thr Ser Gly Ala Leu Gly Leu
                100                 105                 110

Gly Gly Leu Ser Ser Leu Thr Cys Leu Ala Asn Thr Ala Arg Gln Ala
            115                 120                 125

Phe Gln Arg Thr Pro Asp Tyr Val Glu Glu Ala His Arg Arg Met Ala
        130                 135                 140

Glu Ala Ala Ala His Ala Gly His Lys Thr Ala Gln Ala Gly Gln Ala
145                 150                 155                 160

Ile Gln Gly Arg Ala Gln Glu Ala Gly Ala Gly Gly Ala Gly Ala
                165                 170                 175

Gly Ala Gly Gly Gly Gly Arg Ala Ser Ser
            180                 185

<210> SEQ ID NO 8
<211> LENGTH: 148
<212> TYPE: PRT
<213> ORGANISM: O. sativa

<400> SEQUENCE: 8

Met Gly Asp Gln His Arg Gly Val Ile Gly Gly Gly Tyr Gly Asp
 1               5                  10                  15

Arg Gly Gly Gln Glu Gln Gln Glu Lys Gln Pro Phe Met Met Thr Ala
                20                  25                  30

Leu Lys Thr Val Thr Ala Ala Thr Ala Gly Gly Ser Ile Leu Val Leu
            35                  40                  45

Ser Gly Leu Ile Leu Ala Gly Thr Val Ile Ala Leu Thr Val Ala Thr
 50                  55                  60

Pro Val Leu Val Ile Phe Ser Pro Val Leu Val Pro Ala Ala Ile Ala
 65                  70                  75                  80

Leu Ala Leu Met Ala Ala Gly Phe Val Thr Ser Val Gly Leu Gly Val
                85                  90                  95

Ala Ala Leu Ser Val Phe Ser Trp Met Tyr Lys Tyr Leu Thr Gly Lys
                100                 105                 110

His Pro Pro Gly Ala Asp His Leu Asp His Thr Lys Ala Arg Val Ala
            115                 120                 125

Ser Lys Leu Arg Asp Ile Lys Glu Ala Ala His His Leu Ile Asp Gln
130                 135                 140

Ala Gln Ala Ser
145

<210> SEQ ID NO 9
<211> LENGTH: 216
<212> TYPE: PRT
<213> ORGANISM: B.oleracea

<400> SEQUENCE: 9

Arg Phe Phe Arg Met Phe Ser Phe Ile Phe Pro Leu Leu Asn Val Ile
```

```
                1               5                  10                 15
Lys Leu Ile Ile Ala Ser Val Thr Ser Leu Val Cys Leu Ala Phe Ser
                20                 25                 30

Cys Val Thr Leu Gly Gly Ser Ala Val Ala Leu Ile Val Ser Thr Pro
            35                 40                 45

Leu Phe Ile Ile Phe Ser Pro Ile Leu Val Pro Ala Thr Ile Ala Thr
    50                 55                 60

Thr Leu Ala Ser Gly Leu Met Ala Gly Thr Thr Leu Gly Leu Thr
65                 70                 75                 80

Gly Ile Gly Leu Ile Thr Gly Leu Val Arg Thr Ala Gly Gly Val Thr
                85                 90                 95

Leu Ala Glu Ser Pro Ile Arg Arg Ile Ile Asn Arg Ile Lys Ala
            100                105                110

Arg Leu Gly Gly Gly Gly Ser Arg Leu Ala Met Leu Lys Lys Ile
            115                120                125

Leu Gly Leu Ile Lys Lys Leu Arg Gly Met Ser Ser Gly Gly Ala Ala
            130                135                140

Pro Ala Leu Lys Gln His Gln Gln Leu Arg Pro Arg Met Glu Leu His
145                150                155                160

Pro Arg His Leu His Arg Pro Asn Lys Glu Arg Trp Phe Met Leu Phe
                165                170                175

Gln Tyr Val Ala His Lys Asn Cys Val Ile Ile Asn Leu Arg Ile Tyr
                180                185                190

Asp Ser Glu Thr Lys Lys Lys Ile Ala Leu Leu Leu Ser Phe Ile Gln
                195                200                205

Tyr Ser Phe Leu Cys Asn Asn Val
    210                215

<210> SEQ ID NO 10
<211> LENGTH: 148
<212> TYPE: PRT
<213> ORGANISM: C. arabica

<400> SEQUENCE: 10

Met Ala Glu His Tyr Gln Leu Gln Gln Arg Pro Thr Glu Ala Val Lys
1               5                  10                 15

Ser Phe Leu Pro Gln Lys Gly Pro Ser Thr Ser His Val Leu Ala Val
                20                 25                 30

Val Thr Leu Leu Pro Val Ala Gly Val Leu Leu Gly Leu Ser Gly Leu
            35                 40                 45

Ile Leu Val Gly Thr Val Ile Gly Leu Ala Val Thr Thr Pro Leu Phe
    50                 55                 60

Val Ile Phe Ser Pro Ile Leu Val Pro Ala Val Phe Ala Leu Gly Leu
65                 70                 75                 80

Ala Leu Ala Gly Phe Leu Thr Ser Gly Ala Phe Gly Ile Thr Ala Leu
                85                 90                 95

Ala Ser Leu Ser Trp Met Leu Asn Tyr Ile Arg Leu Met Lys Ala Ser
            100                105                110

Ser Gln Glu Gln Met Asp Leu Ala Lys Trp Arg Val Gln Asp Thr Ala
            115                120                125

Gly Gln Val Gly Gln Lys Ala Arg Asp Val Gly Gln Arg Thr Gln Asp
            130                135                140

Val Ala Arg Ala
145
```

```
<210> SEQ ID NO 11
<211> LENGTH: 380
<212> TYPE: PRT
<213> ORGANISM: B.oleraceae

<400> SEQUENCE: 11

Met Arg Asn Glu Ile Gln Asn Glu Thr Ala Gln Thr Asp Gln Thr Gln
1               5                   10                  15

Gly Ser Met Phe Ser Phe Phe Asp Leu Phe Pro Phe Leu Leu Pro Met
            20                  25                  30

Phe Glu Val Ile Lys Met Val Val Ala Ser Val Ala Ser Val Val Tyr
        35                  40                  45

Leu Gly Phe Ala Gly Val Thr Leu Ser Gly Ser Ala Val Ala Leu Ala
    50                  55                  60

Val Ser Thr Pro Leu Phe Ile Ile Phe Ser Pro Ile Leu Leu Pro Ala
65                  70                  75                  80

Ile Ala Ala Thr Thr Val Leu Ala Ala Gly Leu Gly Ser Lys Lys Val
                85                  90                  95

Ala Ala Ala Pro Ala Ala Ser Pro Ser Leu Ser Leu Leu Gly Ile Pro
            100                 105                 110

Glu Ser Ile Lys Pro Ser Asn Val Ile Pro Glu Ser Ile Lys Pro Ser
        115                 120                 125

Asn Ile Ile Pro Glu Ser Ile Lys Pro Ser Asn Ile Ile Pro Glu Ser
    130                 135                 140

Val Lys Pro Ser Asn Ile Lys Asp Lys Ile Lys Asp Thr Ile Gly Lys
145                 150                 155                 160

Val Lys Asn Lys Ile Asn Ala Lys Lys Glu Glu Lys Ser Lys Gly Lys
                165                 170                 175

Ser Glu Asp Ser Ser Lys Gly Lys Gly Lys Ser Lys Gly Glu Asp Thr
            180                 185                 190

Thr Thr Asp Glu Asp Lys Pro Gly Ser Gly Gly Lys His Gly Lys Gly
        195                 200                 205

Glu Ser Lys His Gly Lys Gly Glu Ser Thr His Gly Lys Gly Gly Lys
    210                 215                 220

His Gly Ser Glu Gly Ser Ser Met Asp Glu Gly Lys His Gly Gly Lys
225                 230                 235                 240

His Gly Ser Gly Gly Ser Pro Met Gly Val Gly Lys His Gly Ser Gly
                245                 250                 255

Gly Lys His Glu Ser Gly Gly Ser Pro Met Gly Gly Gly Lys His Gly
            260                 265                 270

Ser Gly Gly Lys His Glu Ser Gly Gly Ala Ser Met Gly Gly Gly Lys
        275                 280                 285

His Gly Ser Gly Gly Arg His Glu Gly Gly Gly Ser Ala Met Gly Gly
    290                 295                 300

Gly Lys His Gly Ser Gly Gly Lys His Gly Ser Glu Gly Lys His Gly
305                 310                 315                 320

Gly Glu Gly Ser Ser Met Gly Lys Asn Ser Leu Ser Lys Asn Lys Lys
                325                 330                 335

Glu Phe His Tyr Arg Asp Gln Ala Met Asp Ala Ser Ser Thr Ser Glu
            340                 345                 350

Ser Ser Asp Gly Ser Ser Asp Gly Ser Ser Asp Gly Ser Ser Ser
        355                 360                 365

Asp Gly Ser Ser His Gly Ser Gly Gly Lys His Ile
    370                 375                 380
```

<210> SEQ ID NO 12
<211> LENGTH: 145
<212> TYPE: PRT
<213> ORGANISM: S. indicum

<400> SEQUENCE: 12

```
Met Ala Glu His Tyr Gly Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
            100                 105                 110

Leu Glu Ser Ala Lys Thr Lys Leu Ala Ser Lys Ala Arg Glu Met Lys
        115                 120                 125

Asp Arg Ala Glu Gln Phe Ser Gln Gln Pro Val Ala Gly Ser Gln Thr
    130                 135                 140

Ser
145
```

<210> SEQ ID NO 13
<211> LENGTH: 501
<212> TYPE: DNA
<213> ORGANISM: S. indicum

<400> SEQUENCE: 13

```
atggcggacc gcgaccgtcc acaccccac caaattcaag tccaccctca acatccgcac    60
cgctatgaag gtggcgtcaa gtctctcctc cctcaaaagg cccctccac cacccagatt   120
ctcgccataa tcaccctcct tcccatcagc ggcacgcttc tttgcctagc tgggatcacg   180
ctcgtcggga ccctcatcgg acttgcagtc gccaccccag tcttcgtgat cttcagccct   240
gttctggttc ccgcagccat actgatagcc ggcgcggtca cggcgttttt gacgtccggg   300
gcttttgggc tgacggggct ttcgtcgctt tcttgggttc tgaattcatt cagacgggcg   360
acggggcagg ggccgttgga gtacgcgaag cgaggcgtgc aggaggggac tttgtatgtg   420
ggagagaaga cgaagcaagc gggcgaagcg attaagagca cagccaagga aggagggcga   480
gaagggactg cacggacttg a                                             501
```

<210> SEQ ID NO 14
<211> LENGTH: 559
<212> TYPE: DNA
<213> ORGANISM: S. indicum

<400> SEQUENCE: 14

```
ggcacgagcg ccgtccccat ggcggacgaa ccccacgacc agcgccccac cgacgtcatc    60
aagagctacc tccccgaaaa gggtccctcc acctctcaag tcctcgccgt cgtgaccctc   120
ttccccctcg gcgccgtcct cctctgccta gccggtctca ttcttaccgg gaccatcatc   180
```

```
ggcctcgccg tcgccacccc gctcttcgtc atcttcagcc ccatcttggt ccccgccgcc      240
ctaaccatcg ccctagccgt caccggtttc ttgacctccg gagctttcgg catcaccgcc      300
ctgtcctcga tttcgtggtt gctgaactac gttaggcgaa tgcggggag cttgccagag       360 cagctggatc atgcacggcg gcgcgtgcag gagacggtgg gccagaagac aagggaggcg      420
gggcagagaa gccaagatgt aataagaccg tgaggttttt ggatattaga tgttggttaa     480
tttgtgtgtt taatgtatat atgaggggtt gaataagtta ataaaattgc ggatttggta      540 caaaaaaaa aaaaaaaaa                                                    559
```

<210> SEQ ID NO 15
<211> LENGTH: 1800
<212> TYPE: DNA
<213> ORGANISM: A. thaliana
<400> SEQUENCE: 15

```
ccatggctat acccaacctc ggtcttggtc acaccaggaa ctctctggta agctagctcc       60
actccccaga aacaaccggc gccaaattgc cggaattgct gacctgaaga cggaacatca     120
tcgtcgggtc cttgggcgat gcggcggaa gatgggtcag cttgggcttg aggacgagac      180
ccgaatcgag tctgttgaaa ggttgttcat tgggatttgt atacggagat tggtcgtcga    240
gaggtttgag ggaaaggaca aatgggtttg gctctggaga agagagtgc ggctttagag      300 agagaattga gaggtttaga gagagatgcg gcggcgatga cggggaggaga gacgacgagg    360 acctgcatta tcaaagcagt gacgtggtga aatttggaac ttttaagagg cagatagatt     420
tattatttgt atccattttc ttcattgttc tagaatgtcg cggaacaaat tttaaaacta     480
aatcctaaat ttttctaatt ttgttgccaa tagtggatat gtgggccgta tagaaggaat    540
ctattgaagg cccaaaccca tactgacgag cccaaaggtt cgttttgcgt tttatgtttc     600
ggttcgatgc caacgccaca ttctgagcta ggcaaaaaac aaacgtgtct ttgaatagac     660
tcctctcgtt aacacatgca gcggctgcat ggtgacgcca ttaacacgtg gcctacaatt    720
gcatgatgtc tccattgaca cgtgacttct cgtctccttt cttaatatat ctaacaaaca    780
ctcctacctc ttccaaaata tatacacatc tttttgatca atctctcatt caaaatctca    840
ttctctctag taaacaagaa caaaaaaatg gcggatacag ctagaggaac ccatcacgat     900
atcatcggca gagaccagta cccgatgatg gccgagacc gagaccagta ccagatgtcc      960
ggacgaggat ctgactactc caagtctagg cagattgcta aagctgcaac tgctgtcaca    1020
gctggtggtt ccctccttgt tctctccagc cttacccttg ttggaactgt catagctttg    1080
actgttgcaa cacctctgct cgttatcttc agcccaatcc ttgtcccggc tctcatcaca    1140
gttgcactcc tcatcaccgg ttttctttcc tctggagggt ttggcattgc cgctataacc   1200
gttttctctt ggatttacaa gtaagcacac atttatcatc ttacttcata attttgtgca    1260
atatgtgcat gcatgtgttg agccagtagc tttggatcaa ttttttttggt cgaataacaa   1320 atgtaacaat aagaaattgc aaattctagg gaacatttgg ttaactaaat acgaaatttg   1380
acctagctag cttgaatgtg tctgtgtata tcatctatat aggtaaaatg cttggtatga   1440
tacctattga ttgtgaatag gtacgcaacg ggagagcacc cacagggatc agacaagttg    1500
gacagtgcaa ggatgaagtt gggaagcaaa gctcaggatc tgaaagacag agctcagtac   1560 tacgacagc aacatactgg tgggaacat gaccgtgacc gtactcgtgg tggccagcac     1620
actacttaag ttaccccact gatgtcatcg tcatagtcca ataactccaa tgtcggggag   1680
ttagtttatg aggaataaag tgtttagaat ttgatcaggg ggagataata aaagccgagt   1740
```

```
ttgaatcttt tgttataag taatgtttat gtgtgtttct atatgttgtc aaatggtacc    1800
```

<210> SEQ ID NO 16
<211> LENGTH: 450
<212> TYPE: DNA
<213> ORGANISM: A. thaliana

<400> SEQUENCE: 16

```
atggcggatc atcaacaaca tcagcaacaa caacaaccaa taatgaggag tctccatgaa     60
tcatcaccat cgactcggca gatagtgaga ttcgtaacgg cagctacgat cggcctatca    120
ctcctcgtgc tctcaggact aacactaacc ggaacggtga tcggtttgat cgtagcgacg    180
ccgttgatgg ttctgttcag cccggtgttg gtaccggcag tgataacgat agggcttctg    240
acgatgggat tcctattctc cggtggttgt ggggtggcag cagctacggc gttaacgtgg    300
atttataagt acgttaccgg aaaacacccg atgggagcgg ataaggtgga ttacgcgagg    360
atgaggatag cggagaaagc caaagagttg gacattata cgcactcgca gccacaacaa    420
acacaccaaa ccacaacaac tactcattag                                    450
```

<210> SEQ ID NO 17
<211> LENGTH: 625
<212> TYPE: DNA
<213> ORGANISM: H. annuus

<400> SEQUENCE: 17

```
actaccacca cttacgaccg tcatttcacc accaccaac cccactaccg ccaagacgac      60
aggtcccgct acgaccagca aacccattcc cagtccacca gcaggacact cgccatcatc    120
gccctacttc ctgtcggcgg aatcttactc ggcttagccg ctctcacatt catcgggacg    180
cttatcgggc tcgccctcgc caccccgctt ttcgtcatat tcagcccgat catcgtgccg    240
gccgttctaa caatcgggct tgctgttaca ggcttttttgg cgtcggggac gttcgggttg    300
acgggtttga gctcattgtc gtatttgttc aatatggtta ggcagacggc tgggtcggtg    360
cccgagtcct tggattatgt taaggggacg ttgcaggatg ccggtgagta tgccgggcag    420
aagacgaagg atttcgggca gaagattcag agcacggctc atgagatggg tgatcagggg    480
caggttggtg ttcatgctca agttggtggc gggaagaag ggcgaaaaag cggtgatcgg    540
acttgaggat tcaaggttga tattgtggaa taataatgtt gatgtaagtt tttagtgtta    600
tcaaagcttt gtttgtttgt ttgta                                          625
```

<210> SEQ ID NO 18
<211> LENGTH: 737
<212> TYPE: DNA
<213> ORGANISM: B. napus

<400> SEQUENCE: 18

```
gaattccatt caaactagta aacaatgggg atactcagga agaaaaaaca cgagcgaaag     60
ccgtcgttta agagtgtttt aaccgcaata ttagctacac atgccgcaac attcctcttg    120
ttgatcgccg tgtatccct cgccggcaca gccgccgcat ttatcgctac catgccacta    180
ttcgtagtat tcagtccgat tctcgtacca gctggtatta ccactggttt actgactacg    240
ggtttagcag ccgccggtgg cgccggcgcg actgctgtca ccatcatcct gtggctctac    300
aagcgagcaa cgggcaaggc gccgccaaaa gtcctagaaa aagtcttgaa aaagataata    360
ccaggtgctg cagctgcacc agcagccgct ccaggagccg ctccagcagc ggcgccagca    420
```

| | |
|---|---|
| gccgcaccag ctgtggcgcc agcagccgca ccagctgctg cgccagcacc taagccagca | 480 |
| gccccaccag cacctaagcc agcagccgca ccgagtatat gaaaagaagt ggtgggcatg | 540 |
| agtaaaggtt gatatggaaa actggataca tagaaaaaag agtaatccaa cttttaaaaa | 600 |
| ataaataaca acttcacgtg gggatagaaa aattttcaaa tattatttta ctaatggatg | 660 |
| tcgcggtaca aaataataac aaatgtaagc ctttttattg tatagtattt taagaacgaa | 720 |
| gctatgtagc gttgaca | 737 |

<210> SEQ ID NO 19
<211> LENGTH: 1153
<212> TYPE: DNA
<213> ORGANISM: Z. mays

<400> SEQUENCE: 19

| | |
|---|---|
| aactactccg tcactttgtt tgcaaagctc ctcctcgatc catcgatcac tgcaccggcc | 60 |
| ggcggcaccg cgctcgcagg ggctagccaa cgagacggca gcaatggcgg accgtgaccg | 120 |
| cagcggcatc tacggcggcg cccacgccac ctacgggcag cagcagcagc agggaggagg | 180 |
| cgggcgcccg atgggtgagc aggtgaaggg catgctccac gacaaggggc cgacggcgtc | 240 |
| gcaggcgctg acggtggcga cgctgttccc gctgggcggg ctgctgctgg tgctgtcggg | 300 |
| gctggcgctg acggcctccg tggtggggct ggccgtggcc acgccggtgt tcctgatctt | 360 |
| cagccccgtg ctggtccccg ccgcgctgct catcgggacg gccgtcatgg ggttcctcac | 420 |
| gtcgggcgcg ctggggctcg ggggcctgtc ctcgctcacg tgcctcgcca acacggcgcg | 480 |
| gcaggcgttc cagcgcaccc cggactacgt ggaggaggcg caccgcagga tggcggaggc | 540 |
| cgcggcgcac gcgggccaca gaccgcgca ggcaggccag gccatccagg gcagggcgca | 600 |
| ggaggccggc gccgggggag gtgcaggtgc cggcgctggc ggcggcggca gggcttcctc | 660 |
| gtaagcaagt catccatgca tggattatgg atagatgcgc gcgtgcgtgt ctatcagtat | 720 |
| cagcagccag cagggtcgtc gcggaatgct gtgttcctgt acgtgtgggt gaccgtcctt | 780 |
| ccgtccttcg tctttctccc cccgagtgtg tgttacgtat gtcctggtgt cgtcgtgtg | 840 |
| tgttcatcgc cgctccagtt gaattccggt gtctgttcat cgccgctcca ggtcgtagat | 900 |
| gtgaatatac tttgctaggg gaataagtga taagtctgtc tggaaggtaa tgtttgagct | 960 |
| ttgctagtgt ggctgggcac tctggtcact ggttgtgttg tgcatgcatc agctgtatga | 1020 |
| tcgtcgtctg ttgtggaaaa ttggtcaatg tattctcttg ctgataatt tgtgacatct | 1080 |
| aattgttatg tatcgtctct ttgctgaata atcagtttct gatttatctt gcattaaaaa | 1140 |
| aaaaaaaaaa aaa | 1153 |

<210> SEQ ID NO 20
<211> LENGTH: 447
<212> TYPE: DNA
<213> ORGANISM: O. sativa

<400> SEQUENCE: 20

| | |
|---|---|
| atgggtgatc agcacagagg agtgatcggc ggtggcggct acggtgaccg tggtggccag | 60 |
| gagcagcagg agaagcagcc cttcatgatg acggctctga agacggtgac cgcggcgacg | 120 |
| gccgggggct cgattctggt gctgtccggg ctgatcctgg ccgggaccgt catcgcgctc | 180 |
| acggtggcca ccccggtgtt ggtcatcttc agcccgtgc tggtaccggc ggccatcgcg | 240 |
| ctggcgctca tggcggccgg gttcgtcacc tcggttggtc tcggtgtagc cgcgctctcc | 300 |
| gttttctcgt ggatgtacaa gtacctcacc gggaagcacc cgccgggcgc cgaccatctg | 360 |

```
gaccacacca aggcgagggt cgcgtccaag ctccgcgaca tcaaggaggc ggcgcatcac    420
ctcatcgacc aggcgcaggc gtcttag                                       447

<210> SEQ ID NO 21
<211> LENGTH: 709
<212> TYPE: DNA
<213> ORGANISM: B. oleracea

<400> SEQUENCE: 21
gccgtttttt cagaatgttc tcttttatct tcccattgct gaacgttata aagcttatta    60
tagcttccgt gacctcctta gtctgcttag cgtttcttg tgtgacactc ggtggttcag    120
ccgtggcatt aatcgtatcc acaccacttt tcatcatatt tagtccaatt ctcgtacctg    180
ccactattgc cactaccctc ctagccagtg ggctcatggc gggtaccacc ctcggactga    240
ccggcatagg tctcatcacg gggctcgtta ggacggcagg aggagttaca ttggccgaat    300
caccgataag aagaattata ataaatagaa ttaaagcaag acttgggggt ggcggcggtt    360
cacgtctggc aatgctcaaa aaaattctgg gactcattaa aaagttgcgt ggtatgtctt    420
caggtggagc agcacctgcg ctgaagcagc accagcagct gcgcccgcgg atggagctgc    480
acccgcggca cctgcaccga cctaacaaag aacgttggtt catgctgttc caatatgtag    540
cacataaaaa ttgtgtaata attaacttaa gaatttatga ttcggaaact aaaaagaaaa    600
tagccctttt actatctttt atacaatata gttttctatg taataatgtt taatttgctt    660
ataactataa aagactcatg catagttgat taggaaaaaa aaaaaaaaa               709

<210> SEQ ID NO 22
<211> LENGTH: 447
<212> TYPE: DNA
<213> ORGANISM: C. arabica

<400> SEQUENCE: 22
atggctgagc actaccagct gcagcaacgc cccacagagg ccgtcaaaag cttccttcct    60
cagaagggtc catcaacttc acatgtgtta gcagttgtca cgctcctccc agttgcggga    120
gtcctgctag gcctttccgg gctgattctc gtcggaacgg tcatcggtct ggcggtgaca    180
acccgctttt tcgttatctt tagccccatt ttggtcccag ctgtatttgc cctagggctg    240
gccctggccg ggttcttgac ctccggtgct ttcgggatca ctgcacttgc ttcattgtcg    300
tggatgctga actacatccg actcatgaag gcgtcttccc aggagcaaat ggacctcgca    360
aagtggcgcg tgcaggacac tgccggccaa gttggtcaga agcgagaga cgtgggccag    420 agaactcaag atgtagccag agcatga                                       447

<210> SEQ ID NO 23
<211> LENGTH: 1000
<212> TYPE: DNA
<213> ORGANISM: B. oleraceae

<400> SEQUENCE: 23
atgagaaacg aaattcaaaa cgaaacagct cagactgatc agacacaggg aagtatgttt    60
tcttttttcg atttgttccc tttcctcctc ccaatgtttg aggttatcaa gatggttgtt    120
gcttccgttg cgtccgtagt ctatttaggc ttcgccggtg taacactcag tggttcagcc    180
gtggcattag ccgtatctac ccctcttttc atcatattca gtccgattct cttacctgct    240
attgcagcca ctactgtcct agccgcaggg ctcggcagta aaaagttgc ggcggctccg    300
```

-continued

| | |
|---|---|
| gcagcttcac catccctatc tctgttgggc ataccggaga gtattaaacc aagtaatgtt | 360 |
| ataccggaga gtattaaacc aagtaatatt ataccggaga gtattaaacc aagtaatatt | 420 |
| ataccggaga gtgttaaacc aagtaatatt aaggacaaaa ttaaggatac gataggcaaa | 480 |
| gttaagaata agatcaatgc taaaaaggaa gaaaaatcaa aaggtaaaag tgaagattct | 540 |
| tccaagggta aaggtaaatc aaagggtgaa gatacgacta cggatgaaga taaacccgga | 600 |
| agtggaggta aacacggaaa gggtgagagt aaacacggaa agggtgagag tacacacgga | 660 |
| aagggaggta aacatggaag tgaaggttcg tcaatggatg aaggtaaaca cggaggtaag | 720 |
| catgaagcg gaggttcgcc tatggtgta ggtaaacacg gaagcggagg taaacatgaa | 780 |
| agtggaggtt cgcctatggg tggaggtaaa cacggaagcg gaggtaaaca tgaaagtgga | 840 |
| ggtgcgtcta tgggtggagg taaacacgga agcggaggta gacatgaagg tggaggttcg | 900 |
| gctatgggtg gaggtaagca cggaagtgga ggcaaacacg gaagtgaagg taaacacggg | 960 |
| ggtgagggct cttctatggg taaaaatagt ctatccaaga | 1000 |

<210> SEQ ID NO 24
<211> LENGTH: 706
<212> TYPE: DNA
<213> ORGANISM: S. indicum

<400> SEQUENCE: 24

| | |
|---|---|
| tcacctcaaa gtttgctccg ttcttgacag aaatggctga gcattatggt caacaacagc | 60 |
| agaccagggc gcctcacctg cagctgcagc cgcgcgccca gcgggtagtg aaggcggcca | 120 |
| ccgccgtgac agccggcggc tcgcttctcg tcctctctgg cctcacttta gccggaactg | 180 |
| ttattgcgct caccatcgcc actccgctgc ttgtgatctt tagccccgtt ctggtgccgg | 240 |
| cggtcataac catttttcttg ctgggtgcgg gttttctggc atccggaggc ttcggcgtgg | 300 |
| cggcgctgag tgtgctgtcg tggatttaca gatatctgac agggaaacac ccgccggggg | 360 |
| cggatcagct ggaatcggca aagacgaagc tggcgagcaa ggcgcgagag atgaaggata | 420 |
| gggcagagca gttctcgcag cagcctgttg cggggtctca aacttcttga gctctttttc | 480 |
| tgttgtatga aaatcttaaa ctgtgtggcc cttcgctagt tggtttgatg tctggttcag | 540 |
| agtgctgatt attttggcgac attcggaggg cgttggagat gataagcttt caatttgttt | 600 |
| ttcgaagtta atattttgttc ttgatttttga tgtctttggt atatatggtc ttttagtaca | 660 |
| ttatgttatc aataaacaag tcattttcaa aaaaaaaaaa aaaaaa | 706 |

<210> SEQ ID NO 25
<211> LENGTH: 520
<212> TYPE: PRT
<213> ORGANISM: A. thaliana

<400> SEQUENCE: 25

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

```
Asn Asn Gly Gly Gly Asp Asn Gly Gly Gly Arg Gly Gly Glu
                85                  90                  95
Gly Arg Gly Asn Ala Asp Ala Thr Phe Thr Tyr Arg Pro Ser Val Pro
            100                 105                 110
Ala His Arg Arg Ala Arg Glu Ser Pro Leu Ser Ser Asp Ala Ile Phe
            115                 120                 125
Lys Gln Ser His Ala Gly Leu Phe Asn Leu Cys Val Val Leu Ile
        130                 135                 140
Ala Val Asn Ser Arg Leu Ile Ile Glu Asn Leu Met Lys Tyr Gly Trp
145                 150                 155                 160
Leu Ile Arg Thr Asp Phe Trp Phe Ser Ser Arg Ser Leu Arg Asp Trp
                165                 170                 175
Pro Leu Phe Met Cys Cys Ile Ser Leu Ser Ile Phe Pro Leu Ala Ala
                180                 185                 190
Phe Thr Val Glu Lys Leu Val Leu Gln Lys Tyr Ile Ser Glu Pro Val
                195                 200                 205
Val Ile Phe Leu His Ile Ile Thr Met Thr Glu Val Leu Tyr Pro
            210                 215                 220
Val Tyr Val Thr Leu Arg Cys Asp Ser Ala Phe Leu Ser Gly Val Thr
225                 230                 235                 240
Leu Met Leu Leu Thr Cys Ile Val Trp Leu Lys Leu Val Ser Tyr Ala
                245                 250                 255
His Thr Ser Tyr Asp Ile Arg Ser Leu Ala Asn Ala Ala Asp Lys Ala
                260                 265                 270
Asn Pro Glu Val Ser Tyr Tyr Val Ser Leu Lys Ser Leu Ala Tyr Phe
            275                 280                 285
Met Val Ala Pro Thr Leu Cys Tyr Gln Pro Ser Tyr Pro Arg Ser Ala
        290                 295                 300
Cys Ile Arg Lys Gly Trp Val Ala Arg Gln Phe Ala Lys Leu Val Ile
305                 310                 315                 320
Phe Thr Gly Phe Met Gly Phe Ile Ile Glu Gln Tyr Ile Asn Pro Ile
                325                 330                 335
Val Arg Asn Ser Lys His Pro Leu Lys Gly Asp Leu Leu Tyr Ala Ile
            340                 345                 350
Glu Arg Val Leu Lys Leu Ser Val Pro Asn Leu Tyr Val Trp Leu Cys
        355                 360                 365
Met Phe Tyr Cys Phe Phe His Leu Trp Leu Asn Ile Leu Ala Glu Leu
        370                 375                 380
Leu Cys Phe Gly Asp Arg Glu Phe Tyr Lys Asp Trp Trp Asn Ala Lys
385                 390                 395                 400
Ser Val Gly Asp Tyr Trp Arg Met Trp Asn Met Pro Val His Lys Trp
                405                 410                 415
Met Val Arg His Ile Tyr Phe Pro Cys Leu Arg Ser Lys Ile Pro Lys
                420                 425                 430
Thr Leu Ala Ile Ile Ile Ala Phe Leu Val Ser Ala Val Phe His Glu
            435                 440                 445
Leu Cys Ile Ala Val Pro Cys Arg Leu Phe Lys Leu Trp Ala Phe Leu
    450                 455                 460
Gly Ile Met Phe Gln Val Pro Leu Val Phe Ile Thr Asn Tyr Leu Gln
465                 470                 475                 480
Glu Arg Phe Gly Ser Thr Val Gly Asn Met Ile Phe Trp Phe Ile Phe
                485                 490                 495
Cys Ile Phe Gly Gln Pro Met Cys Val Leu Leu Tyr Tyr His Asp Leu
```

-continued

```
                500             505             510
Met Asn Arg Lys Gly Ser Met Ser
            515             520

<210> SEQ ID NO 26
<211> LENGTH: 518
<212> TYPE: PRT
<213> ORGANISM: T. majus

<400> SEQUENCE: 26

Met Ala Val Ala Glu Ser Ser Gln Asn Thr Thr Met Ser Gly His
1               5                   10                  15

Gly Asp Ser Asp Leu Asn Asn Phe Arg Arg Lys Pro Ser Ser Ser
            20                  25                  30

Val Ile Glu Pro Ser Ser Ser Gly Phe Thr Ser Thr Asn Gly Val Pro
            35                  40                  45

Ala Thr Gly His Val Ala Glu Asn Arg Asp Gln Asp Arg Val Gly Ala
        50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                    85                  90                  95

Phe Thr Tyr Arg Pro Ser Phe Pro Ala His Arg Arg Val Arg Glu Ser
                100                 105                 110

Pro Leu Ser Ser Asp Ala Ile Phe Lys Gln Ser His Ala Gly Leu Phe
            115                 120                 125

Asn Leu Cys Ile Val Val Leu Ile Ala Val Asn Ser Arg Leu Ile Ile
        130                 135                 140

Glu Asn Leu Met Lys Tyr Gly Trp Leu Ile Asp Thr Gly Phe Trp Phe
145                 150                 155                 160

Ser Ser Arg Ser Leu Gly Asp Trp Ser Ile Phe Met Cys Cys Leu Thr
                    165                 170                 175

Leu Pro Ile Phe Pro Leu Ala Ala Phe Ile Val Glu Lys Leu Val Gln
                180                 185                 190

Arg Asn His Ile Ser Glu Leu Val Ala Val Leu Leu His Val Ile Val
            195                 200                 205

Ser Thr Ala Ala Val Leu Tyr Pro Val Ile Val Ile Leu Thr Cys Asp
        210                 215                 220

Ser Val Tyr Met Ser Gly Val Val Leu Met Leu Phe Gly Cys Ile Met
225                 230                 235                 240

Trp Leu Lys Leu Val Ser Tyr Ala His Thr Ser Ser Asp Ile Arg Thr
                    245                 250                 255

Leu Ala Lys Ser Gly Tyr Lys Gly Asp Ala His Pro Asn Ser Thr Ile
                260                 265                 270

Val Ser Cys Ser Tyr Asp Val Ser Leu Lys Ser Leu Ala Tyr Phe Met
            275                 280                 285

Val Ala Pro Thr Leu Cys Tyr Gln Pro Ser Tyr Pro Arg Ser Ser Cys
        290                 295                 300

Ile Arg Lys Gly Trp Val Val Arg Gln Phe Val Lys Leu Ile Val Phe
305                 310                 315                 320

Ile Gly Leu Met Gly Phe Ile Ile Glu Gln Tyr Ile Asn Pro Ile Val
                    325                 330                 335

Arg Asn Ser Lys His Pro Leu Lys Gly Asp Phe Leu Tyr Ala Ile Glu
                340                 345                 350
```

-continued

Arg Val Leu Lys Leu Ser Val Pro Asn Leu Tyr Val Trp Leu Cys Met
355                 360                 365

Phe Tyr Ser Phe Phe His Leu Trp Leu Asn Ile Leu Ala Glu Leu Leu
370                 375                 380

Arg Phe Gly Asp Arg Glu Phe Tyr Lys Asp Trp Trp Asn Ala Lys Thr
385                 390                 395                 400

Val Ala Glu Tyr Trp Lys Met Trp Asn Met Pro Val His Arg Trp Met
                405                 410                 415

Val Arg His Leu Tyr Phe Pro Cys Leu Arg Asn Gly Ile Pro Lys Glu
                420                 425                 430

Gly Ala Ile Ile Ile Ala Phe Leu Val Ser Gly Ala Phe His Glu Leu
                435                 440                 445

Cys Ile Ala Val Pro Cys His Val Phe Lys Leu Trp Ala Phe Ile Gly
            450                 455                 460

Ile Met Phe Gln Val Pro Leu Val Leu Ile Thr Asn Tyr Leu Gln Glu
465                 470                 475                 480

Lys Phe Ser Asn Ser Met Val Gly Asn Met Ile Phe Trp Phe Ile Phe
                485                 490                 495

Cys Ile Leu Gly Gln Pro Met Cys Val Leu Tyr Tyr His Asp Leu
            500                 505                 510

Ile Asn Leu Lys Glu Lys
            515

<210> SEQ ID NO 27
<211> LENGTH: 494
<212> TYPE: PRT
<213> ORGANISM: Z. mays

<400> SEQUENCE: 27

Met Ala Pro Pro Pro Ser Met Pro Ala Ala Ser Asp Arg Ala Gly Pro
1               5                   10                  15

Gly Arg Asp Ala Gly Asp Ser Ser Ser Leu Arg Leu Arg Arg Ala Pro
                20                  25                  30

Ser Ala Asp Ala Gly Asp Leu Ala Gly Asp Ser Ser Gly Gly Leu Arg
                35                  40                  45

Glu Asn Gly Glu Pro Gln Ser Pro Thr Asn Pro Pro Gln Glu Gln
50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Arg Gln Ser
                85                  90                  95

His Ala Gly Leu Leu Asn Leu Cys Ile Val Val Leu Ile Ala Val Asn
                100                 105                 110

Ser Arg Leu Ile Ile Glu Asn Leu Met Lys Tyr Gly Leu Leu Ile Arg
                115                 120                 125

Ala Gly Phe Trp Phe Ser Ala Arg Ser Leu Gly Asp Trp Pro Leu Leu
                130                 135                 140

Met Cys Cys Leu Thr Leu Pro Val Phe Pro Leu Val Ala Leu Met Ala
145                 150                 155                 160

Glu Lys Leu Ile Thr Arg Lys Leu Ile Gly Glu His Val Ile Leu
                165                 170                 175

Leu His Ile Ile Ile Thr Thr Ser Ala Ile Val Tyr Pro Val Val Val
                180                 185                 190

Thr Leu Lys Cys Asp Ser Ala Val Leu Ser Gly Phe Val Leu Met Phe
                195                 200                 205

Leu Ala Ser Ile Met Trp Met Lys Leu Val Ser Tyr Ala His Thr Asn
            210                 215                 220

Tyr Asp Ile Arg Val Leu Ser Lys Ser Thr Glu Lys Gly Ala Ala Tyr
225                 230                 235                 240

Gly Asn Tyr Val Asp Pro Glu Asn Met Lys Asp Pro Thr Phe Lys Ser
                245                 250                 255

Leu Val Tyr Phe Met Leu Ala Pro Thr Leu Cys Tyr Gln Pro Thr Tyr
            260                 265                 270

Pro Gln Thr Thr Cys Ile Arg Lys Gly Trp Val Thr Gln Gln Leu Ile
        275                 280                 285

Lys Cys Val Val Phe Thr Gly Leu Met Gly Phe Ile Ile Glu Gln Tyr
290                 295                 300

Ile Asn Pro Ile Val Lys Asn Ser Lys His Pro Leu Lys Gly Asn Phe
305                 310                 315                 320

Leu Asn Ala Ile Glu Arg Val Leu Lys Leu Ser Val Pro Thr Leu Tyr
                325                 330                 335

Val Trp Leu Cys Met Phe Tyr Cys Phe Phe His Leu Trp Leu Asn Ile
            340                 345                 350

Val Ala Glu Leu Leu Cys Phe Gly Asp Arg Glu Phe Tyr Lys Asp Trp
        355                 360                 365

Trp Asn Ala Lys Thr Val Glu Glu Tyr Trp Arg Met Trp Asn Met Pro
370                 375                 380

Val His Lys Trp Ile Ile Arg His Ile Tyr Phe Pro Cys Ile Arg Lys
385                 390                 395                 400

Gly Phe Ser Arg Gly Val Ala Ile Leu Ile Ser Phe Leu Val Ser Ala
                405                 410                 415

Val Phe His Glu Ile Cys Ile Ala Val Pro Cys His Ile Phe Lys Phe
            420                 425                 430

Trp Ala Phe Ser Gly Ile Met Phe Gln Ile Pro Leu Val Phe Leu Thr
        435                 440                 445

Arg Tyr Leu His Ala Thr Phe Lys His Val Met Val Gly Asn Met Ile
450                 455                 460

Phe Trp Phe Phe Phe Ser Ile Val Gly Gln Pro Met Cys Val Leu Leu
465                 470                 475                 480

Tyr Tyr His Asp Val Met Asn Arg Gln Ala Gln Ala Ser Arg
                485                 490

<210> SEQ ID NO 28
<211> LENGTH: 314
<212> TYPE: PRT
<213> ORGANISM: A. thaliana

<400> SEQUENCE: 28

Met Gly Gly Ser Arg Glu Phe Arg Ala Glu Glu His Ser Asn Gln Phe
1               5                   10                  15

His Ser Ile Ile Ala Met Ala Ile Trp Leu Gly Ala Ile His Phe Asn
            20                  25                  30

Val Ala Leu Val Leu Cys Ser Leu Ile Phe Leu Pro Pro Ser Leu Ser
        35                  40                  45

Leu Met Val Leu Gly Leu Leu Ser Leu Phe Ile Phe Ile Pro Ile Asp
    50                  55                  60

His Arg Ser Lys Tyr Gly Arg Lys Leu Ala Arg Tyr Ile Cys Lys His
65                  70                  75                  80

Ala Cys Asn Tyr Phe Pro Val Ser Leu Tyr Val Glu Asp Tyr Glu Ala

```
                    85                  90                  95
Phe Gln Pro Asn Arg Ala Tyr Val Phe Gly Tyr Glu Pro His Ser Val
                100                 105                 110

Leu Pro Ile Gly Val Val Ala Leu Cys Asp Leu Thr Gly Phe Met Pro
            115                 120                 125

Ile Pro Asn Ile Lys Val Leu Ala Ser Ser Ala Ile Phe Tyr Thr Pro
        130                 135                 140

Phe Leu Arg His Ile Trp Thr Trp Leu Gly Leu Thr Ala Ala Ser Arg
145                 150                 155                 160

Lys Asn Phe Thr Ser Leu Leu Asp Ser Gly Tyr Ser Cys Val Leu Val
                165                 170                 175

Pro Gly Gly Val Gln Glu Thr Phe His Met Gln His Asp Ala Glu Asn
            180                 185                 190

Val Phe Leu Ser Arg Arg Gly Phe Val Arg Ile Ala Met Glu Gln
        195                 200                 205

Gly Ser Pro Leu Val Pro Val Phe Cys Phe Gly Gln Ala Arg Val Tyr
    210                 215                 220

Lys Trp Trp Lys Pro Asp Cys Asp Leu Tyr Leu Lys Leu Ser Arg Ala
225                 230                 235                 240

Ile Arg Phe Thr Pro Ile Cys Phe Trp Gly Val Phe Gly Ser Pro Leu
                245                 250                 255

Pro Cys Arg Gln Pro Met His Val Val Val Gly Lys Pro Ile Glu Val
            260                 265                 270

Thr Lys Thr Leu Lys Pro Thr Asp Glu Glu Ile Ala Lys Phe His Gly
        275                 280                 285

Gln Tyr Val Glu Ala Leu Arg Asp Leu Phe Glu Arg His Lys Ser Arg
    290                 295                 300

Val Gly Tyr Asp Leu Glu Leu Lys Ile Leu
305                 310

<210> SEQ ID NO 29
<211> LENGTH: 317
<212> TYPE: PRT
<213> ORGANISM: B. napus

<400> SEQUENCE: 29

Met Gly Lys Val Arg Asp Phe Gly Ala Glu Asp His Ile Pro Ser Asn
1               5                   10                  15

Ile Phe His Ala Val Thr Ala Ile Ser Ile Cys Leu Ser Ala Ile Tyr
                20                  25                  30

Leu Asn Leu Ala Leu Val Leu Ile Ser Leu Phe Phe Leu Pro Thr Ser
            35                  40                  45

Leu Ser Leu Leu Val Leu Gly Leu Leu Ser Leu Phe Ile Ile Ile Pro
        50                  55                  60

Ile Asp Asp Arg Ser Lys Tyr Gly Leu Lys Leu Ala Arg Tyr Ile Cys
65                  70                  75                  80

Lys His Ala Ala Ser Tyr Phe Pro Val Thr Leu His Val Glu Asp Tyr
                85                  90                  95

Glu Ala Phe Lys Pro Asp Arg Ser Tyr Val Phe Gly Tyr Glu Pro His
                100                 105                 110

Ser Val Trp Pro Ile Gly Ala Val Ala Leu Val Asp Leu Ala Gly Phe
            115                 120                 125

Met Pro Leu Pro Asn Ile Lys Leu Leu Ala Ser Asn Ala Ile Phe Tyr
        130                 135                 140
```

```
Thr Pro Phe Leu Arg His Met Trp Ala Trp Leu Gly Leu Ala Ser Ala
145                 150                 155                 160

Ser Arg Lys Ser Phe Ser Ser Leu Leu Glu Ser Gly Tyr Ser Cys Ile
            165                 170                 175

Leu Val Pro Gly Gly Val Gln Glu Thr Phe His Leu Gln His Asp Val
        180                 185                 190

Glu Asn Val Phe Leu Ser Ser Arg Arg Gly Phe Val Arg Ile Ala Met
    195                 200                 205

Glu Gln Gly Ala Pro Leu Val Pro Val Phe Cys Phe Gly Gln Ser Arg
210                 215                 220

Ala Tyr Lys Trp Trp Lys Pro Asp Cys Asp Leu Tyr Phe Lys Leu Ala
225                 230                 235                 240

Arg Ala Ile Arg Phe Thr Pro Ile Cys Phe Trp Gly Val Phe Gly Ser
                245                 250                 255

Pro Ile Pro Tyr Arg His Pro Ile His Val Val Gly Lys Pro Ile
            260                 265                 270

Gln Val Ala Lys Ser Leu Gln Pro Thr Asp Glu Glu Ile Asp Glu Leu
        275                 280                 285

His Gly Gln Phe Val Glu Ala Leu Lys Asp Leu Phe Glu Arg His Lys
    290                 295                 300

Ala Gly Ala Gly Tyr Ser Asp Leu Gln Leu Asn Ile Leu
305                 310                 315

<210> SEQ ID NO 30
<211> LENGTH: 345
<212> TYPE: PRT
<213> ORGANISM: A. hypogaea

<400> SEQUENCE: 30

Met Glu Val Ser Gly Ala Val Leu Arg Asn Val Thr Cys Pro Ser Phe
1               5                   10                  15

Ser Val His Val Ser Ser Arg Arg Gly Gly Asp Ser Cys Val Thr
            20                  25                  30

Val Pro Val Arg Met Arg Lys Lys Ala Val Val Arg Cys Cys Cys Gly
        35                  40                  45

Phe Ser Asp Ser Gly His Val Gln Tyr Tyr Gly Asp Glu Lys Lys Lys
    50                  55                  60

Glu Asn Gly Thr Ala Met Leu Ser Thr Lys Lys Lys Leu Lys Met Leu
65                  70                  75                  80

Lys Lys Arg Val Leu Phe Asp Asp Leu Gln Gly Asn Leu Thr Trp Asp
                85                  90                  95

Ala Ala Met Val Leu Met Lys Gln Leu Glu Gln Val Arg Ala Glu Glu
            100                 105                 110

Lys Glu Leu Lys Lys Lys Arg Lys Gln Glu Lys Lys Glu Ala Lys Leu
        115                 120                 125

Lys Ala Ser Lys Met Asn Thr Asn Pro Asp Cys Glu Ser Ser Ser Ser
    130                 135                 140

Ser Ser Ser Ser Glu Ser Glu Ser Glu Ser Glu Ser Glu Ser Glu Cys Asp
145                 150                 155                 160

Asn Glu Val Val Asp Met Lys Lys Asn Ile Lys Val Gly Val Ala Val
                165                 170                 175

Ala Val Ala Asp Ser Pro Arg Lys Ala Glu Thr Met Ile Leu Tyr Thr
            180                 185                 190

Ser Leu Val Ala Arg Asp Val Ser Ala Asn His His His His Asn Ala
        195                 200                 205
```

-continued

```
Val Glu Leu Phe Ser Arg Asn Asn Asp Ile Ser Val Gly Ser Ile Asn
    210                 215                 220

Gly Gly Leu Lys Asn Glu Asn Thr Ala Val Ile Thr Thr Glu Ala Ile
225                 230                 235                 240

Pro Gln Lys Arg Ile Glu Val Cys Met Gly Asn Lys Cys Lys Lys Ser
                245                 250                 255

Gly Ser Ile Ala Leu Leu Gln Glu Phe Glu Arg Val Val Gly Ala Glu
                260                 265                 270

Gly Gly Ala Ala Ala Ala Val Val Gly Cys Lys Cys Met Gly Lys Cys
                275                 280                 285

Lys Ser Ala Pro Asn Val Arg Ile Gln Asn Ser Thr Ala Asp Lys Ile
    290                 295                 300

Ala Glu Gly Phe Asn Asp Ser Val Lys Val Pro Ala Asn Pro Leu Cys
305                 310                 315                 320

Ile Gly Val Ala Trp Arg Met Leu Lys Pro Leu Trp Leu Arg Phe Leu
                325                 330                 335

Gly Glu Asn Gln Glu Ser Thr Asn Glu
                340                 345

<210> SEQ ID NO 31
<211> LENGTH: 671
<212> TYPE: PRT
<213> ORGANISM: A. thaliana

<400> SEQUENCE: 31

Met Pro Leu Ile His Arg Lys Lys Pro Thr Glu Lys Pro Ser Thr Pro
1               5                   10                  15

Pro Ser Glu Glu Val Val His Asp Glu Asp Ser Gln Lys Lys Pro His
                20                  25                  30

Glu Ser Ser Lys Ser His His Lys Lys Ser Asn Gly Gly Gly Lys Trp
            35                  40                  45

Ser Cys Ile Asp Ser Cys Cys Trp Phe Ile Gly Cys Val Cys Val Thr
    50                  55                  60

Trp Trp Phe Leu Leu Phe Leu Tyr Asn Ala Met Pro Ala Ser Phe Pro
65              70                  75                  80

Gln Tyr Val Thr Glu Arg Ile Thr Gly Pro Leu Pro Asp Pro Pro Gly
                85                  90                  95

Val Lys Leu Lys Lys Glu Gly Leu Lys Ala Lys His Pro Val Val Phe
                100                 105                 110

Ile Pro Gly Ile Val Thr Gly Gly Leu Glu Leu Trp Glu Gly Lys Gln
            115                 120                 125

Cys Ala Asp Gly Leu Phe Arg Lys Arg Leu Trp Gly Gly Thr Phe Gly
    130                 135                 140

Glu Val Tyr Lys Arg Pro Leu Cys Trp Val Glu His Met Ser Leu Asp
145                 150                 155                 160

Asn Glu Thr Gly Leu Asp Pro Ala Gly Ile Arg Val Arg Ala Val Ser
                165                 170                 175

Gly Leu Val Ala Ala Asp Tyr Phe Ala Pro Gly Tyr Phe Val Trp Ala
            180                 185                 190

Val Leu Ile Ala Asn Leu Ala His Ile Gly Tyr Glu Glu Lys Asn Met
                195                 200                 205

Tyr Met Ala Ala Tyr Asp Trp Arg Leu Ser Phe Gln Asn Thr Glu Val
    210                 215                 220

Arg Asp Gln Thr Leu Ser Arg Met Lys Ser Asn Ile Glu Leu Met Val
```

```
            225                 230                 235                 240
Ser Thr Asn Gly Gly Lys Lys Ala Val Ile Val Pro His Ser Met Gly
                245                 250                 255

Val Leu Tyr Phe Leu His Phe Met Lys Trp Val Glu Ala Pro Ala Pro
                260                 265                 270

Leu Gly Gly Gly Gly Pro Asp Trp Cys Ala Lys Tyr Ile Lys Ala
                275                 280                 285

Val Met Asn Ile Gly Gly Pro Phe Leu Gly Val Pro Lys Ala Val Ala
        290                 295                 300

Gly Leu Phe Ser Ala Glu Ala Lys Asp Val Ala Val Ala Arg Ala Ile
305                 310                 315                 320

Ala Pro Gly Phe Leu Asp Thr Asp Ile Phe Arg Leu Gln Thr Leu Gln
                    325                 330                 335

His Val Met Arg Met Thr Arg Thr Trp Asp Ser Thr Ser Met Leu
                340                 345                 350

Pro Lys Gly Gly Asp Thr Ile Trp Gly Gly Leu Asp Trp Ser Pro Glu
                355                 360                 365

Lys Gly His Thr Cys Cys Gly Lys Lys Gln Lys Asn Asn Glu Thr Cys
        370                 375                 380

Gly Glu Ala Gly Glu Asn Gly Val Ser Lys Lys Ser Pro Val Asn Tyr
385                 390                 395                 400

Gly Arg Met Ile Ser Phe Gly Lys Glu Val Ala Glu Ala Ala Pro Ser
                    405                 410                 415

Glu Ile Asn Asn Ile Asp Phe Arg Gly Ala Val Lys Gly Gln Ser Ile
                420                 425                 430

Pro Asn His Thr Cys Arg Asp Val Trp Thr Glu Tyr His Asp Met Gly
            435                 440                 445

Ile Ala Gly Ile Lys Ala Ile Ala Glu Tyr Lys Val Tyr Thr Ala Gly
        450                 455                 460

Glu Ala Ile Asp Leu Leu His Tyr Val Ala Pro Lys Met Met Ala Arg
465                 470                 475                 480

Gly Ala Ala His Phe Ser Tyr Gly Ile Ala Asp Asp Leu Asp Asp Thr
                    485                 490                 495

Lys Tyr Gln Asp Pro Lys Tyr Trp Ser Asn Pro Leu Glu Thr Lys Leu
                500                 505                 510

Pro Asn Ala Pro Glu Met Glu Ile Tyr Ser Leu Tyr Gly Val Gly Ile
            515                 520                 525

Pro Thr Glu Arg Ala Tyr Val Tyr Lys Leu Asn Gln Ser Pro Asp Ser
        530                 535                 540

Cys Ile Pro Phe Gln Ile Phe Thr Ser Ala His Glu Glu Asp Glu Asp
545                 550                 555                 560

Ser Cys Leu Lys Ala Gly Val Tyr Asn Val Asp Gly Asp Glu Thr Val
                565                 570                 575

Pro Val Leu Ser Ala Gly Tyr Met Cys Ala Lys Ala Trp Arg Gly Lys
            580                 585                 590

Thr Arg Phe Asn Pro Ser Gly Ile Lys Thr Tyr Ile Arg Glu Tyr Asn
        595                 600                 605

His Ser Pro Pro Ala Asn Leu Leu Glu Gly Arg Gly Thr Gln Ser Gly
    610                 615                 620

Ala His Val Asp Ile Met Gly Asn Phe Ala Leu Ile Glu Asp Ile Met
625                 630                 635                 640

Arg Val Ala Ala Gly Gly Asn Gly Ser Asp Ile Gly His Asp Gln Val
                645                 650                 655
```

-continued

```
His Ser Gly Ile Phe Glu Trp Ser Glu Arg Ile Asp Leu Lys Leu
            660                 665                 670

<210> SEQ ID NO 32
<211> LENGTH: 685
<212> TYPE: PRT
<213> ORGANISM: R. communis

<400> SEQUENCE: 32

Met Pro Val Ile Arg Arg Lys Lys Pro Thr Ser Glu Pro Asn Lys Asn
1               5                   10                  15

Ser Ala Ser Asp Ser Lys Thr Pro Ser Glu Glu Glu His Glu Gln
            20                  25                  30

Glu Gln Glu Gln Glu Glu Asp Lys Asn Asn Lys Lys Lys Tyr Pro Lys
            35                  40                  45

Lys Lys Ser Ser Glu Ile Asn Ala Lys Lys Trp Ser Cys Ile Asp Ser
50                  55                  60

Cys Cys Trp Phe Val Gly Cys Ile Cys Val Thr Trp Trp Val Leu Leu
65                  70                  75                  80

Phe Leu Tyr Asn Ala Val Pro Ala Ser Leu Pro Gln Tyr Val Thr Glu
                85                  90                  95

Ala Ile Thr Gly Pro Leu Pro Asp Pro Pro Gly Val Lys Leu Lys Lys
            100                 105                 110

Glu Gly Leu Thr Ala Lys His Pro Val Val Phe Val Pro Gly Ile Val
            115                 120                 125

Thr Ala Gly Leu Glu Leu Trp Glu Gly His Gln Cys Ala Asp Gly Leu
130                 135                 140

Phe Arg Lys Arg Leu Trp Gly Gly Thr Phe Gly Glu Val Tyr Lys Arg
145                 150                 155                 160

Pro Leu Cys Trp Val Glu His Met Ser Leu Asp Asn Glu Thr Gly Leu
                165                 170                 175

Asp Pro Pro Gly Ile Arg Val Arg Pro Val Ser Gly Leu Val Ala Ala
            180                 185                 190

Asp Tyr Phe Ala Pro Gly Tyr Phe Val Trp Ala Val Leu Ile Ala Asn
            195                 200                 205

Leu Ala Arg Ile Gly Tyr Glu Glu Lys Thr Met Phe Met Ala Ser Tyr
210                 215                 220

Asp Trp Arg Leu Ser Phe Gln Asn Thr Glu Val Arg Asp Gln Thr Leu
225                 230                 235                 240

Ser Arg Met Lys Ser Asn Ile Glu Leu Met Val Ser Ile Asn Gly Gly
                245                 250                 255

Asn Lys Ala Val Ile Val Pro His Ser Met Gly Val Leu Tyr Phe Leu
            260                 265                 270

His Phe Met Lys Trp Val Glu Ala Pro Ala Pro Met Gly Gly Gly Gly
            275                 280                 285

Gly Pro Asp Trp Cys Ala Lys His Ile Lys Ala Val Met Asn Ile Gly
            290                 295                 300

Gly Pro Phe Leu Gly Val Pro Lys Ala Val Ala Gly Leu Phe Ser Ala
305                 310                 315                 320

Glu Ala Arg Asp Ile Ala Val Ala Arg Ala Ile Ala Pro Gly Phe Leu
                325                 330                 335

Asp Asn Asp Met Phe Arg Leu Gln Thr Leu Gln His Met Met Arg Met
            340                 345                 350

Ser Arg Thr Trp Asp Ser Thr Met Ser Met Ile Pro Arg Gly Gly Asp
```

```
                355                 360                 365
Thr Ile Trp Gly Asp Leu Asp Trp Ser Pro Glu Glu Gly Tyr Ile Pro
370                 375                 380

Arg Lys Lys Arg Gln Arg Asn Asn Ala Thr Asp Asn Val Asn Glu Gly
385                 390                 395                 400

Gly Ala Glu Ser Glu Ile Ser Gln Arg Lys Ile Val Arg Tyr Gly Arg
                405                 410                 415

Met Ile Ser Phe Gly Lys Asn Ile Ala Glu Ala Pro Ser Tyr Asp Ile
                420                 425                 430

Glu Arg Ile Asp Phe Arg Asp Ala Val Lys Gly Arg Ser Val Ala Asn
                435                 440                 445

Asn Thr Cys Leu Asp Val Trp Thr Glu Tyr His Glu Met Gly Phe Gly
                450                 455                 460

Gly Ile Lys Ala Val Ala Glu Tyr Lys Val Tyr Thr Ala Gly Ser Thr
465                 470                 475                 480

Ile Glu Leu Leu Gln Phe Val Ala Pro Lys Met Met Glu Arg Gly Ser
                485                 490                 495

Ala His Phe Ser Tyr Gly Ile Ala Asp Asn Leu Glu Asp Pro Lys Tyr
                500                 505                 510

Glu His Tyr Lys Tyr Trp Ser Asn Pro Leu Glu Thr Lys Leu Pro Asn
                515                 520                 525

Ala Pro Glu Met Glu Ile Phe Ser Met Tyr Gly Val Gly Ile Pro Thr
                530                 535                 540

Glu Arg Ala Tyr Val Tyr Glu Phe Ser Pro Ala Ala Glu Cys Tyr Ile
545                 550                 555                 560

Pro Phe Gln Ile Asp Thr Ser Ala Asn Asp Gly Asp Glu Asp Gly Cys
                565                 570                 575

Leu Lys Asp Gly Val Tyr Thr Val Asp Gly Asp Glu Thr Val Pro Val
                580                 585                 590

Leu Ser Ala Gly Phe Met Cys Ala Lys Ala Trp Arg Gly Lys Thr Arg
                595                 600                 605

Phe Asn Pro Ser Gly Ser Arg Thr Tyr Ile Arg Glu Tyr Asp His Ser
610                 615                 620

Pro Pro Ala Asn Leu Leu Glu Gly Arg Gly Thr Gln Ser Gly Ala His
625                 630                 635                 640

Val Asp Ile Met Gly Asn Phe Ala Leu Ile Glu Asp Ile Met Arg Val
                645                 650                 655

Ala Ala Gly Ala Thr Gly Glu Asp Leu Gly Gly Asp Gln Val Tyr Ser
                660                 665                 670

Asp Ile Phe Lys Trp Ser Gln Lys Ile Lys Leu Pro Leu
                675                 680                 685

<210> SEQ ID NO 33
<211> LENGTH: 2074
<212> TYPE: DNA
<213> ORGANISM: A. thaliana

<400> SEQUENCE: 33
tgaatccttt ttcctttctt cttcttcttc tcttcagaga aaactttgct tctctttcta      60
taaggaacca gacacgaatc ccattcccac cgatttctta gcttcttcct tcaatccgct     120
ctttccctct ccattagatt ctgtttcctc tttcaatttc ttctgcatgc ttctcgattc     180
tctctgacgc ctctttttctc ccgacgctgt ttcgtcaaac gcttttcgaa atggcgattt     240
tggattctgc tggcgttact acggtgacgg agaacggtgg cggagagttc gtcgatcttg     300
```

```
ataggcttcg tcgacggaaa tcgagatcgg attcttctaa cggacttctt ctctctggtt      360
ccgataataa ttctccttcg gatgatgttg gagctcccgc cgacgttagg gatcggattg      420
attccgttgt taacgatgac gctcagggaa cagccaattt ggccggagat aataacggtg      480
gtggcgataa taacggtggt ggaagaggcg gcggagaagg aagaggaaac gccgatgcta      540
cgtttacgta tcgaccgtcg gttccagctc atcgagggc gagagagagt ccacttagct       600
ccgacgcaat cttcaaacag agccatgccg gattattcaa cctctgtgta gtagttctta      660
ttgctgtaaa cagtagactc atcatcgaaa atcttatgaa gtatggttgg ttgatcagaa      720
cggatttctg gttagttcca agatcgctgc gagattggcc gcttttcatg tgttgtatat      780
ccctttcgat ctttcctttg gctgccttta cggttgagaa attggtactt cagaaataca     840
tatcagaacc tgttgtcatc tttcttcata ttattatcac catgacagag gttttgtatc      900
cagtttacgt cacgctaagg tgtgattctg cttttttatc aggtgtcact ttgatgctcc      960
tcacttgcat tgtgtggcta aagttggttt cttatgctca tactagctat gacataagat     1020
ccctagccaa tgcagctgat aaggccaatc ctgaagtctc ctactacgtt agcttgaaga     1080
gcttggcata tttcatggtc gctcccacat tgtgttatca gccaagttat ccacgttctg     1140
catgtatacg gaagggttgg gtggctcgtc aatttgcaaa actggtcata ttcaccggat     1200
tcatgggatt tataatagaa caatatataa atcctattgt caggaactca aagcatcctt     1260
tgaaaggcga tcttctatat gctattgaaa gagtgttgaa gctttcagtt ccaaatttat     1320
atgtgtggct ctgcatgttc tactgcttct tccacctttg gttaaacata ttggcagagc     1380
ttctctgctt cggggatcgt gaattctaca aagattggtg gaatgcaaaa agtgtgggag     1440
attactggag aatgtggaat atgcctgttc ataaatggat ggttcgacat atatacttcc     1500
cgtgcttgcg cagcaagata ccaaagacac tcgccattat cattgctttc ctagtctctg     1560
cagtctttca tgagctatgc atcgcagttc cttgtcgtct cttcaagcta tgggcttttc     1620
ttgggattat gtttcaggtg cctttggtct tcatcacaaa ctatctacag gaaaggtttg     1680
gctcaacggt ggggaacatg atcttctggt tcatcttctg cattttcgga caaccgatgt     1740
gtgtgcttct ttattaccac gacctgatga accgaaaagg atcgatgtca tgaaacaact     1800
gttcaaaaaa tgactttctt caaacatcta tggcctcgtt ggatctccgt tgatgttgtg     1860
gtggttctga tgctaaaacg acaaatagtg ttataaccat tgaagaagaa aagaaaatta     1920
gagttgttgt atctgcaaaa attttggtag agacacgcga acccgtttgg attttgttat     1980
ggtgtaaaga aatttcaatc aaaaaactgt tgtaataatt gttaccaaaa agaaatgctt     2040
ttctggaaac gaggggaaaa atagtagttt tgtt                                  2074
```

<210> SEQ ID NO 34
<211> LENGTH: 2090
<212> TYPE: DNA
<213> ORGANISM: T. majus

<400> SEQUENCE: 34

```
acgcggggag ttttcaaaat catattatgc ttttcttca ctactgcatg aactttcttt        60
ctacttcttg caactgattt gtaatcctta cacatgtttc tagttttctc catataaaaa     120
aaatattctc tgagcttctc gattctctag agagagaagg ccaaaaaaaa atggcggtgg     180
cagagtcgtc acagaacacg acaaccatga gtggtcacgg cgactcggat ctcaacaatt     240
tccgtagaag gaaaccgagt tcctccgtga ttgaaccttc gtcgtccggt tttacatcca     300
```

```
ccaatggcgt accggcgact ggccacgtgg ctgagaatcg tgaccaggat cgggtagggg      360
ctatggagaa cgcaacagga tcggtcaact taattggaaa tggtggaggc gtggttatcg      420
ggaatgaaga gaaacaggta ggggagactg atatacgatt cacttaccgg ccttcgtttc      480
cggctcatcg gagggtgagg gagagtcctc ttagctctga tgcaatcttc aaacagagcc      540
atgcgggttt attcaacttg tgtatagtag tgctcattgc agtaaacagt aggcttatca      600
tcgaaaatct tatgaagtat ggttggttga tcgatactgg tttctggttt agctcaagat      660
cactgggtga ttggtccatc tttatgtgct gtcttacact cccaattttc ccacttgctg      720
cttttattgt tgaaaagctg gtgcagcgaa atcatatatc tgaacttgtt gctgttctcc      780
ttcatgtaat cgtttctacc gctgcagttt tatatccagt tattgtgatc ttaacgtgtg      840
attcggtgta tatgtctggt gtggtattga tgctctttgg ttgcattatg tggttgaagc      900
tggtgtcata tgcacatact agttctgata ttagaacact ggccaaatct ggctataagg      960
gggatgcgca ccccaattca accattgtga gttgctcata tgatgttagc ttgaagagtt     1020
tggcatactt catggttgct ccgacattat gttaccagcc tagctatcct cgttcgtcgt     1080
gtatccgcaa gggttgggtt gttcgtcaat ttgtcaaact aatagttttc ataggactca     1140
tggggttcat tatagaacaa tatattaatc ctatcgttcg aaattccaaa cacccattga     1200
aaggagattt tttatatgca atagaaagag ttttgaagct ttcagttcca aatctatatg     1260
tttggctttg catgttctac tcttttttcc acctctggtt gaacatactg gctgagcttc     1320
ttcgctttgg tgatcgtgaa ttctacaaag attggtggaa tgcaaaaact gttgcggagt     1380
attggaaaat gtgaatatg cctgttcata gatggatggt tcgtcatcta tattttccct     1440
gtttgaggaa tgggataccc aaggaaggtg ccattattat cgcgttctta gtttctggtg     1500 cttttccatga gctctgcatt gcagttcctt gccacgtatt caagttatgg gcctttatag     1560
gcattatgtt tcaggttccc ttggtattga ttacgaatta tctacaagaa aagttcagta     1620
attctatggt gggcaatatg atcttctggt tcatcttctg catacttggc caacctatgt     1680
gtgtccttct atattaccat gacctgataa atctaaagga aaagtgaaaa atggaagtt     1740 gcctatgctc agagtattcc tatcccaatg cacacattat atggttctgt acaatctgtg     1800
cccccttcat cctttacacg tacccatgct ggttcctgca cgatgatttg ccttttgttt     1860
gtaagcaata tttggagaga gtccaattta ggaagtgact agtgtggctt atatcttgta     1920
tactaccttt agtcatgggg gggtttttat attactagta ccaaaagtca agttgtatat     1980
gatttacggt ttagtttctt tcatgttttt tgttttgtg taaatatacg tttcatatat     2040
cactgttttt tcaaagtaaa atcaataata ccccatagat gttgaaactg               2090
```

<210> SEQ ID NO 35
<211> LENGTH: 1485
<212> TYPE: DNA
<213> ORGANISM: Z. mays

<400> SEQUENCE: 35

```
atggccccgc cccctccat gcctgccgcc tccgatcgcg ccggccctgg ccgcgacgcg       60
ggcgactcgt cctcccttcg cctccgccgc gcccctcag ccgacgccgg cgaccttgcc      120
ggcgattcct cgggaggctt gcgggagaac ggcgagccgc aatcgccgac gaatccgccg      180
ccgcaggagc agcagcagca cgagatgcta tactaccgcg cgtcggcgcc cgcccaccgc      240
cgcgtcaagg agagcccct cagctctgac gccatcttcc ggcagagcca tgctggtctt      300
ctgaatctat gcattgttgt tctgatcgca gtgaacagca gactcattat tgagaattta      360
```

| | | |
|---|---|---|
| atgaagtatg gcctgttgat aagagctgga ttttggttta gtgcaagatc gctgggtgac | 420 |
| tggccccttc taatgtgctg cctcactcta ccagttttcc cactagttgc actcatggct | 480 |
| gagaagctga tcacaagaaa gctcattggt gaacatgtgg ttattctact ccatatcatt | 540 |
| attacaacat ctgccattgt ctatccagtt gttgtgactc ttaagtgtga ctcagcagta | 600 |
| ctatctggat tgtgctaat gtttcttgcg agcatcatgt ggatgaagct tgtctcttat | 660 |
| gcacatacaa attatgatat aagggtattg tccaaaagta ctgaaaaggg tgctgcatat | 720 |
| ggaaattatg tcgatcctga aatatgaaa gatccaacct ttaaaagtct agtgtacttt | 780 |
| atgttggccc caacactttg ttaccagcca acttatcctc aaactacatg tattagaaag | 840 |
| ggttgggtga cccagcaact cataaagtgc gtggttttta caggcttgat gggcttcata | 900 |
| attgagcaat atataaaccc aattgtgaag aattccaaac atccactgaa agggaatttt | 960 |
| ttgaatgcta tagaaagagt cttaaaactc tcagtgccaa cattatatgt atggctttgc | 1020 |
| atgttctatt gcttttttca tttatggctg aacattgtag ctgaactcct ctgtttcggt | 1080 |
| gaccgtgaat tctataagga ctggtggaat gccaaaactg ttgaagagta ctggaggatg | 1140 |
| tggaacatgc ctgttcataa gtggatcatc agacacatat attttccatg tataaggaaa | 1200 |
| ggcttttcca ggggtgtagc tattctaatc tcgtttctgg tttcagctgt atttcatgag | 1260 |
| atatgtattg cggtgccttg ccacattttc aaattctggg cattttctgg gatcatgttt | 1320 |
| cagatacccct tggtattctt gacaagatat ctccatgcta cgttcaagca tgtaatggtg | 1380 |
| ggcaacatga tattttggtt cttcttcagt atagtcggac agccgatgtg tgtccttcta | 1440 |
| tactaccatg acgtcatgaa caggcaggcc caggcaagta gatag | 1485 |

<210> SEQ ID NO 36
<211> LENGTH: 1330
<212> TYPE: DNA
<213> ORGANISM: A. thaliana

<400> SEQUENCE: 36

| | | |
|---|---|---|
| agttaaaaga ttggttattt gggctctgca ctcaagtgag agagaagata gatagatctg | 60 |
| agtagaatct tcgattcatt attcgttgtc gtcgttcatc tgtgagaagc ggacaaacca | 120 |
| aagaatccac cggagctagt gatatgggtg gttccagaga gttccgagct gaggaacatt | 180 |
| caaatcaatt ccactctatc atcgccatgg ccatctggct tggcgccatt cacttcaacg | 240 |
| tcgctcttgt tctctgttct ctcatttttcc ttcctccttc tctatctctc atggtcttgg | 300 |
| gcttgctctc tctgtttatc tttatcccaa tcgatcatcg tagcaaatat ggtcgtaagc | 360 |
| tcgctaggta catatgcaag cacgcgtgta attatttccc cgtctctctg tacgtcgagg | 420 |
| attacgaagc tttccagcct aatcgtgcct atgtctttgg ttatgaacca cattcggtgc | 480 |
| taccgattgg agttgttgct ctttgtgatc tcacagggtt tatgcctatt cctaacatta | 540 |
| aagttcttgc aagtagtgct atattctaca ctcccttttct aaggcatata tggacatggt | 600 |
| tagggctcac cgctgcttct aggaagaatt tcacttccct tttggattct ggctacagtt | 660 |
| gtgttcttgt acctggtggt gtgcaggaga cttttcatat gcaacatgat gctgagaatg | 720 |
| tcttcctttc aaggagaaga ggatttgtgc gcatagccat ggaacagggg agccctctgg | 780 |
| ttccagtatt ctgctttggt caggcacgcg tgtacaaatg gtggaagccg gattgtgatc | 840 |
| tctatcttaa actatctaga gcaatcagat tcaccccgat ctgcttctgg ggagttttg | 900 |
| gatcaccatt accgtgtcga cagcctatgc atgtggtcgt tggtaaacca atagaagtca | 960 |

| | |
|---|---|
| caaaaactct gaagccaact gacgaagaga ttgctaagtt tcatggccag tatgtggaag | 1020 |
| cgcttaggga tctgtttgag aggcacaagt cccgagtcgg ctatgatctt gagctgaaaa | 1080 |
| ttctttgaac aaaatctcca atggaaataa ttacttgtgt gtatccttca ttaattgtta | 1140 |
| ccttggagct ggatttggac ttaatataaa tgactacatc atgtagtcta catgtattgc | 1200 |
| atgtctttag catcgactgt tgaagtaatg gaatacgttt ataaagcctg taaattacat | 1260 |
| gtcgtcttgc acaagagtat gtggtaataa taacatttga cccaaaaata atactagtta | 1320 |
| aatttttcct | 1330 |

```
<210> SEQ ID NO 37
<211> LENGTH: 954
<212> TYPE: DNA
<213> ORGANISM: B. napus

<400> SEQUENCE: 37
```

| | |
|---|---|
| atgggcaaag tcagagactt tggagctgag gatcatatcc catcaaacat attccatgca | 60 |
| gtgaccgcca tatccatctg cctcagcgcc atttacttga acctcgctct tgttctcatc | 120 |
| tccctcttct tcctcccaac ttctctctcc ctcctggtct tgggcctgct ctctctgttt | 180 |
| atcatcatcc ctatagatga tcgtagcaag tacggtctta agctggctag gtacatatgc | 240 |
| aagcacgcgg ctagttactt ccccgttact ctgcatgtcg aagactacga agctttcaag | 300 |
| cctgatcgct cctatgtatt tggttatgaa ccacactcgg tgtggcccat ggagctgtt | 360 |
| gcacttgttg atctggcagg gtttatgcct cttcctaaca tcaaacttct tgcaagcaat | 420 |
| gctatattct acacgccgtt tctaaggcac atgtgggcat ggttagggct cgcctctgct | 480 |
| tctaggaaga gtttctcttc tcttctggag tctggctata gttgtatcct tgtacctggt | 540 |
| ggtgtgcagg aaacatttca cttgcaacat gatgttgaga acgtcttcct ttcatcgaga | 600 |
| agaggatttg tgcgcatcgc catggaacaa ggggcacctc ttgttccagt tttctgcttt | 660 |
| ggtcagtccc gtgcgtacaa gtggtggaag ccggattgtg accttattt taaactagca | 720 |
| agagcgatca ggtttactcc tatctgtttc tggggagttt tcggatcccc aataccatat | 780 |
| agacacccta ttcatgtggt ggttggtaaa ccaatacaag ttgcaaagtc tctgcagcca | 840 |
| actgatgaag agattgatga gttgcatggc cagtttgtgg aagcgcttaa ggatctgttt | 900 |
| gagaggcaca aggccggagc aggctactct gatctgcagt tgaacattct ttga | 954 |

```
<210> SEQ ID NO 38
<211> LENGTH: 1637
<212> TYPE: DNA
<213> ORGANISM: A. hypogaea

<400> SEQUENCE: 38
```

| | |
|---|---|
| aatgaacttg acataaagtg gttgtttgta acaccccatt tagtgttttg cttagatgtt | 60 |
| gagagttcta taaacttttg tactatttgg tacccgtaa ttaatagaaa tagaaatgtg | 120 |
| ataatggttc tatgtttcat tccagaaaaa aattgtcatt ttaaaagtt ttcttaaatt | 180 |
| ctgaatggga atgatgatca ttcagatcaa taaggttaac acttttttat atgatatttt | 240 |
| atgtaatctg attaattttt ttttggtgac aaaaaactcg tgccgaattc ggcacgaggt | 300 |
| caaaacctca gaagagagaa aaggagaatt tggttcctaa ttaattctca ccatcaacga | 360 |
| tggaggtttc aggcgccgtt ctaaggaatg tcacgtgccc ttcctttct gtgcacgtga | 420 |
| gttcccgtcg tcgtggtggt gatagttgtg ttacagtgcc ggtgaggatg agaaaaaagg | 480 |
| cggtggtgcg ttgttgctgc gggttcagtg attcggggca tgtgcagtat tacggggacg | 540 |

```
agaagaagaa ggagaatgga accgctatgt tgagcaccaa gaagaagctc aagatgctga      600
agaaacgtgt ccttttcgat gatcttcaag gaaacctgac ttgggatgct gctatggttt      660
tgatgaagca gctagagcaa gtaagggcag aggagaagga attgaagaaa aaaaggaagc      720
aagagaagaa ggaggcaaaa ctcaaagcct ctaagatgaa caccaatcct gattgcgaat      780
cgtcatcgtc atcgtcatca tctgaatctg aatctgaatc aagtgagagt gaatgtgaca      840
atgaggtggt tgacatgaag aagaacatta aggttggtgt tgccgttgct gttgccgatt      900
ccccacgaaa ggcggaaacc atgattctat acacctccct tgttgcccga gatgttagtg      960
ctaatcatca tcatcataat gccgtggaat tattctctag aaacaatgac atatcagttg     1020
gaagcattaa tggtggcctt aagaatgaga atactgcggt tattaccact gaagctattc     1080
ctcagaagag gattgaggta tgcatgggaa acaagtgcaa gaaatccgga tctattgcat     1140
tgttgcaaga atttgagaga gtggttggtg ctgaaggagg tgctgctgct gcagttgttg     1200
gatgcaagtg catggggaag tgcaagagtg cacctaatgt gaggattcag aactctactg     1260
cagataaaat agctgagggg ttcaatgatt cagttaaggt tccagctaac cctctttgca     1320
ttggggttgc atggaggatg ttgaaaccat tgtggcttag attcttgggc gagaatcagg     1380
aaagtactaa tgaataattt gctggtatgc tgtttggaaa attgtatata cgtagtgcca     1440
gaacctatca gattgttgtt ttattttata taaacataga ctgcatattg ttgtgagatt     1500
cgatttcctc atttattgga acttccagag cctgatttgt gtccattcga gctcgactca     1560
aagatttaca tggcctgctc aatctatgaa ttcaaatttg agggccctgt ttggcattaa     1620
tattaatata ttaatat                                                    1637

<210> SEQ ID NO 39
<211> LENGTH: 2811
<212> TYPE: DNA
<213> ORGANISM: A. thaliana

<400> SEQUENCE: 39
cccaagtgta atattgttat taatacatgg gctatactaa aagcccacg aaaagtttac       60 tgaactattt gaggcccaac aagagcctat cggattaacg cctactgcag aagaaaatct     120
gtctgcactc cacccaagaa aacgcagact aattaatgaa atcaacgaaa cggataggtc     180
gggtctaagg ttgaccatga accgcaacct gaaccaggag caaagtggtc aagttttgcc     240
atccggtccg agtcccttgg aggaataata ccagaacaga aaaaacaga aaagtcgaca     300 ataaacaaaa gagacaaatt tgatttgatt ggttccagaa attcgcagag aaacagctct     360
ttgtctctct cgactgatct aacaatccct aatctgtgtt ctaaattcct ggacgagatt     420
tgacaaagtc cgtatagctt aacctggttt aatttcaagt gacagatatg ccccttattc     480
atcggaaaaa gccgacggag aaaccatcga cgccgccatc tgaagaggtg gtgcacgatg     540
aggattcgca aaagaaacca cacgaatctt ccaaatccca ccataagaaa tcgaacggag     600
gagggaagtg gtcgtgcatc gattcttgtt gttggttcat tgggtgtgtg tgtgtaacct     660
ggtggtttct tctcttcctt tacaacgcaa tgcctgcgag cttccctcag tatgtaacgg     720
agcgaatcac gggtccttg cctgacccgc ccggtgttaa gctcaaaaaa gaaggtctta     780
aggcgaaaca tcctgttgtc ttcattcctg ggattgtcac cggtgggctc gagctttggg     840
aaggcaaaca atgcgctgat ggtttattta gaaaacgttt gtggggtgga acttttggtg     900
aagtctacaa aaggcctcta tgttgggtgg aacacatgtc acttgacaat gaaactgggt     960
```

```
tggatccagc tggtattaga gttcgagctg tatcaggact cgtggctgct gactactttg    1020
ctcctggcta ctttgtctgg gcagtgctga ttgctaacct tgcacatatt ggatatgaag    1080
agaaaaatat gtacatggct gcatatgact ggcggctttc gtttcagaac acagaggtac    1140
gtgatcagac tcttagccgt atgaaaagta atatagagtt gatggtttct accaacggtg    1200 gaaaaaagc agttatagtt ccgcattcca tgggggtctt gtattttcta cattttatga    1260
agtgggttga ggcaccagct cctctgggtg gcggggtgg gccagattgg tgtgcaaagt    1320
atattaaggc ggtgatgaac attggtggac catttcttgg tgttccaaaa gctgttgcag    1380
ggcttttctc tgctgaagca aaggatgttg cagttgccag agcgattgcc ccaggattct    1440
tagacaccga tatatttaga cttcagacct tgcagcatgt aatgagaatg acacgcacat    1500
gggactcaac aatgtctatg ttaccgaagg gaggtgacac gatatggggc gggcttgatt    1560
ggtcaccgga gaaaggccac acctgttgtg ggaaaaagca aagaacaac gaaacttgtg    1620 gtgaagcagg tgaaacgga gtttccaaga aaagtcctgt taactatgga aggatgatat    1680
cttttgggaa agaagtagca gaggctgcgc catctgagat taataatatt gattttcgag    1740
gtgctgtcaa aggtcagagt atcccaaatc acacctgtcg tgacgtgtgg acagagtacc    1800
atgacatggg aattgctggg atcaaagcta tcgctgagta aaggtctac actgctggtg    1860 aagctataga tctactacat tatgttgctc ctaagatgat ggcgcgtggt gccgctcatt    1920
tctcttatgg aattgctgat gatttggatg acaccaagta tcaagatccc aaatactggt    1980
caaatccgtt agagacaaaa ttaccgaatg ctcctgagat ggaaatctac tcattatacg    2040
gagtggggat accaacggaa cgagcatacg tatacaagct taaccagtct cccgacagtt    2100
gcatcccctt tcagatattc acttctgctc acgaggagga cgaagatagc tgtctgaaag    2160
caggagttta caatgtggat ggggatgaaa cagtacccgt cctaagtgcc gggtacatgt    2220
gtgcaaaagc gtggcgtggc aagacaagat tcaacccttc cggaatcaag acttatataa    2280
gagaatacaa tcactctccg ccggctaacc tgttggaagg gcgcgggacg cagagtggtg    2340
cccatgttga tatcatggga aactttgctt tgatcgaaga tatcatgagg gttgccgccg    2400
gaggtaacgg gtctgatata ggacatgacc aggtccactc tggcatattt gaatggtcgg    2460
agcgtattga cctgaagctg tgaatatcat gatctcttta agctgtcctg tcagcttatg    2520
tgaatccaat actttgaaag agagatcatc atcaattcat catcatcgtc atcatcatga    2580
tgctcaactc acaaagaagc ctgagaatga tactttggtg cgaaattctc aatacctctt    2640
taatattctt attgaatgta aattatacaa tcctatctaa tgtttgaacg ataacacaaa    2700
acttgctgcg ccatgtttgt ttgtcttgtc aaaagcatca atttgtgggt tatacgtagt    2760
gtagaggatg attcaaattt gtgataaatt tggtaatcaa agttaattct g             2811
```

<210> SEQ ID NO 40
<211> LENGTH: 2473
<212> TYPE: DNA
<213> ORGANISM: R. communis

<400> SEQUENCE: 40

```
cttgaatttt gttcgatta ctttaaaaaa aattgccttt ttctgaaagc gcttctagtt      60
tgatcttaat ggattattta cttttcagaa attagtagct caaacaaaat taagagagaa     120
aaagagatcg tgggttttt caagaaaaaa gtttcaaaca gaaagcacaa actttccgat     180
gtggcttgcg aggaagttgg ggatgacata aattcttctg ccagtccgaa gttttggata     240
taaagcagtg gttttgtat tttccttttt ccttttctgt atcgtttagt aaagtcacat     300
```

```
ttggcttatt gggtttgttt tatttcctct gtatttgctt tctgtacaaa gactatcaat    360
aattagttaa taagcttaac aaatttaaaa atcttatttt tctttaaacc cagaaatgcc    420
tgtaattcgg aggaaaaaac ccacttctga acccaacaaa aattcagcat cagactcaaa    480
aacgccaagc gaggaagagg aacatgaaca agaacaggaa caagaagaag ataaaaataa    540
caaaaagaaa tacccaaaga agaagagcag tgaaatcaat gcaaaaaaat ggtcatgcat    600
agacagctgt tgttggtttg ttggttgcat ctgcgtgacg tggtgggttt tactatttct    660
ttacaatgca gtgcctgcgt ctttgcctca atacgtaact gaggcaatca cgggtccttt    720
acccgatcca cctggtgtta agctgaaaaa gagggattaa cagcaaagc atccagtggt    780 ttttgtacct gggattgtta ccgcggggct tgaattgtgg aaggccatc agtgtgctga    840 tgggctgttt aggaaacggc tctggggtgg aacttttgga gaagtttata agaggcctct    900
ctgctgggta gagcatatgt ctctagacaa tgaaactgga ttggatcctc ctggtataag    960
ggtcaggcca gtctctggac ttgtggctgc tgattacttt gctccaggct attttgtgtg   1020
ggctgttctg attgctaatt tggcacgcat tggatatgag gagaaaacaa tgttcatggc   1080
ctcatacgat tggagacttt catttcagaa cactgaggtc cgtgaccaaa cattaagccg   1140
gatgaagagt aatatagaac ttatggtttc tatcaatggt ggaaataagg cagttattgt   1200
tccacattcc atgggtgttt tgtactttct gcattttatg aagtggggttg aggcaccagc   1260 tccaatggga ggaggtggtg gaccagattg gtgtgctaag catatcaagg cagtcatgaa   1320
cattggtggg ccatttttag gtgttcccaa agctgttgct gggcttttct cggctgaagc   1380
aagagatatt gcagttgcca gggccatagc accaggtttc ttagataatg atatgttccg   1440
cctacaaaca ttgcaacaca tgatgaggat gtctcgcaca tgggattcga ccatgtcaat   1500
gataccaaga ggtggggaca ctatctgggg cgatcttgat tggtcacctg aagaaggtta   1560
cattcctaga aagaaaaggc agagaaataa tgcaactgat aatgtaaacg aaggtggggc   1620
cgaaagtgag atttctcaaa gaaagattgt tagatatgga agaatgatat catttgggaa   1680
aaatatagca gaggcacctt catatgatat tgaaaggatt gactttaggg atgctgttaa   1740
aggtcgtagt gtgcaaaata atacctgcct tgatgtgtgg actgaatacc atgaaatggg   1800
attcggaggt attaaagccg ttgcagagta taaggtctac actgctggat ctactataga   1860
gctgcttcag tttgtcgccc caaaaatgat ggagcgtggt agtgctcatt tttcttatgg   1920
aattgctgac aatttggagg acccaaaata tgagcactac aaatactggt caaatcccct   1980
ggagacaaag ttacctaatg ctccagaaat ggaaatattt tccatgtatg gagttggcat   2040
accaacagaa agagcttatg tttatgagtt ttctcctgct gctgagtgct acattccatt   2100
tcagattgat acatcagcta atgatggcga tgaagatggc tgtctgaaag atggagtcta   2160
tactgttgat ggggatgaga ctgttcctgt tttaagtgca ggcttcatgt gtgctaaagc   2220
ttggcgtggg aaaaccagat ttaatccttc aggaagtcga acatacatta gagagtacga   2280
tcattctcct ccagctaatt tgctagaggg ccgaggcacc caaagtggtg cccatgttga   2340
tataatgggt aattttgctt taatcgagga tattatgagg gtggcagccg gggctacagg   2400
agaagatttg ggaggcgatc aagtgtattc agatatcttt aagtggtctc agaagatcaa   2460
attaccactg taa                                                      2473
```

<210> SEQ ID NO 41
<211> LENGTH: 2753
<212> TYPE: DNA

<213> ORGANISM: O. sativa

<400> SEQUENCE: 41

```
aagcttttgg tggtaggaat gtagttttct gacaaagtca attactgaat ataaaaaaaa        60
tctgcacagc tctgcgtcaa cagttgtcca agggatgcct caaaaatctg tgcagattat       120
cagtcgtcac gcagaagcag aacatcatgg tgtgctaggt cagcttcttg cattgggcca       180
tgaatccggt tggttgttaa tctctcctct cttattctct tatattaaga tgcataactc       240
ttttatgtag tctaaaaaaa aatccagtgg atcggatagt agtacgtcat ggtgccatta       300
ggtaccgttg aacctaacag atatttatgc atgtgtatat atatagctat atagacaaaa       360
ttggtgccga ttatagaccc aaaagcaata ggtatatata atataataca gaccacacca       420
ccaaactaag aatcgatcaa atagacaagg catgtctcca aattgtctta aactatttcc       480
gtaggttcag ccgttcagga gtcgaatcag cctctgccgg cgttttcttt gcacgtacga       540
cggacacaca tgggcatacc atatagctgg tccatgacat taggagagag aacgtacgtg       600
ttgacctgta gctgagatat aacaaggttg attataatat caccaaacat gaaatcatcc       660
aaggatgacc cataactatc actactatag tactgcatct ggtaaaagaa attgtataga       720
ctctatttcg agcactacca cataacgcct gcaatgtgac ccctaccta ttcactaatg        780
tgcctcttcc cacacgcttt ccacccgtac tgctcacagc tttaagaacc agaacaaatg       840
agtaatatta gtgtcggttc atggctaaaa ccagcactga tgtacatgac cacatatgtc       900
aaatgctgct tctaggcatg acccgctctt actaatacct actcatcgct agaagaattt       960
tcggctgata aattttcaat ttaagcaaga gttatccgcg ttggttcata actcaaactg      1020
atggccccaa ccatattagt gcaaatttca catatgatca taaccttttc atatgaaatc      1080
ggatcgtgat gaactttata taaacattgt agctgtcgat gataacctaca attttatagt     1140
tcacaacctt tttatttcaa gtcatttaaa tgcccaaata ggtgtttcaa atctcagata      1200
gaaatgttca aaagtaaaaa aggtccctat cataacataa ttgatatgta agtgagttgg      1260
aaaatgataa gtacgtgtga gagagatcgg agatcaaatt ctggtgtaat aatgtatgta      1320
tttcagtcat aaaaattggt agcagtagtt ggggctctgt atatataccg gtaaggatgg      1380
gatggtagta gaataattct ttttttgttt ttagtttttt ctggtccaaa atttcaaatt      1440
tggatccctt acttgtacca actaatatta atgagtgttg agggcagtag aggtgcaact      1500
ttaccataat ccctctgttt caggttataa gacgttttga ctttaaattt gactaagttt      1560
atgcgcaaat atagtaatat ttataatact aaattagttt cattaaataa ataattgaat      1620
atattttcat aataaatttg tgttgagttc aaaatattat taatttttc tacaaacttg       1680
gtcaaactta aagcagtttg actttgacca aagtcaaaac gtcttataac ttgaaacgga      1740
tggattactt tttttgtggg gacaagttta caatgtttaa taaaagcaca atccatctta      1800
atgttttcaa gctgaatatt gtaaaattca tggataaacc agcttctaaa tgtttaaccg      1860
ggaaaatgtc gaacgacaaa ttaatatttt taagtgatgg ggagtattaa ttaaggagtg      1920
acaactcaac tttcaatatc gtactaaact gtgggattta ttttctaaaa ttttataccc      1980
tgccaattca cgtgttgtag atctttttt ttcactaacc gacaccaggt atatcaattt       2040
tattgaatat agcagcaaaa agaatgtgtt gtacttgtaa acaaaaagca aactgtacat      2100
aaaaaaaaat gcactcctat ataattaagc tcataaagat gctttgcttc gtgagggccc      2160
aagttttgat gaccttttgc ttgatctcga aattaaaatt taagtactgt taagggagtt      2220
cacaccacca tcaattttca gcctgaagaa acagttaaac aacgaccccg atgaccagtc      2280
```

-continued

| | |
|---|---|
| tactgctctc cacatactag ctgcattatt gatcacaaaa caaaacaaaa cgaaataaaa | 2340 |
| atcagcagcg agagtgtgca gagagagaca aaggtgatct ggcgtggata tctccccatc | 2400 |
| catcctcacc cgcgctgccc atcactcgcc gccgcatact ccatcatgtg gagagaggaa | 2460 |
| gacgaggacc acagccagag cccgggtcga gatgccacca cggccacaac ccacgagccc | 2520 |
| ggcgcgacac caccgcgcgc gcgtgagcca gccacaaacg cccgcggata ggcgcgcgca | 2580 |
| cgccggccaa tcctaccaca tccccggcct ccgcggctcg cgagcgccgc tgccatccga | 2640 |
| tccgctgagt tttggctatt tatacgtacc gcgggagcct gtgtgcagag cagtgcatct | 2700 |
| caagaagtac tcgagcaaag aaggagagag cttggtgagc tgcagagtct aga | 2753 |

<210> SEQ ID NO 42
<211> LENGTH: 1664
<212> TYPE: DNA
<213> ORGANISM: O. sativa

<400> SEQUENCE: 42

| | |
|---|---|
| ttatataaaa gaaaggatga cttcttatcc aaacaaatcc tatagtaatg tcttttaac | 60 |
| tttcagtgac taacatataa accatcaaac gagtccatat taaaggataa tactacgaag | 120 |
| aattgtcatc ccacattttt acactgccac atatcagtta aaatgaaaac cagctcaccc | 180 |
| caagctcacc aagaatcttc gagaaactta taaactccgc cgaaaaatct cggacaaacc | 240 |
| cgcggctcac acgcctcctc gcaccaaaac ccacctagaa tatcctctcc ttggccacgc | 300 |
| gcgcacatca gctcccaatc tcccgcccca ggaggcaatc ccccctcgct tcccgcgcta | 360 |
| tttaaactcc cgcgccatct ccaactccca actcacactc gctcgctcat cgccatctct | 420 |
| ctcagctctc acagctcact gcatcaatgg ccgcggccac catggcgctc tcctccccgg | 480 |
| tgatggcccg cgcggcgccg tcgacctcct ccgcgctctt cggcgaggcg cggatcacca | 540 |
| tgcgcaagac cgccgcgaag cccaagccgg cggcgtcgtc ggggagcccg tggtacggcg | 600 |
| ccgaccgcgt cctctacctc ggcccgctct cgggccgcga gccgccgagc tacctcaccg | 660 |
| gcgagttccc cggcgactac gggtgggaca ccgcggggct ctccgccgac ccggagacgt | 720 |
| tcgccaagaa ccgggagctg gaggtgatcc actcccggtg ggcgatgctg ggcgcgctcg | 780 |
| gctgcgtctt cccggagctc ctcgcccgga acggcgtcaa gttcggcgag gccgtgtggt | 840 |
| tcaaggcggg ctcgcagatc ttcagcgagg gcgggctcga ctacctcggc aacccgagcc | 900 |
| tgatccacgc gcagagcatc ctcgccatct ggcggtgca ggtggtgctc atgggcgccg | 960 |
| tcgagggggta ccggattgct ggcgggccgc tcggcgaggt cgtcgacccg ctgtaccccg | 1020 |
| gcggcgcctt cgaccgcctc ggcctcgccg atgaccccga ggcgtgcgcg gagctcaagg | 1080 |
| tgaagaagat caagaacggc cgcctcgcca tgttctccat gttcggcttc ttcgtccagg | 1140 |
| ccatcgtcac cggcaagggc cccctcgaga acctcgccga ccacctcgcc gaccccgtca | 1200 |
| acaacaacgc ctgggcctac gccaccaact tcgtccccgg caagtgaagt ggggaccgta | 1260 |
| gcttagcagt ggttaattgt ggttggatgg atttgtggcc agcgagttcg ttgtctttgg | 1320 |
| gttggggaag atgggtttag tgcgacgaga tgatgatcga gttggtggtt gtgtacacta | 1380 |
| agaagatgaa gaagaagatg atgttttttgc aataatgatt ttattcgttt cccaactaat | 1440 |
| ggtctaggta cttatccgtg gtgttattct gattagcgga tttctcatct ctattagatc | 1500 |
| ggaaacaaat actccctcga tccccaaaat ataaccattt ctggctatgt atagtataaa | 1560 |
| tatgtagtct aaattgttta tattgtggca tggaaggatt aattagtact ttaaatttac | 1620 |

```
gtatacaata gattgggtcg aatctaggaa gatggtggat ccac                1664

<210> SEQ ID NO 43
<211> LENGTH: 1887
<212> TYPE: DNA
<213> ORGANISM: P. vulgaris

<400> SEQUENCE: 43
gaattcagtg cattgagaag gtgctgaaga gggaggaagt atgtgggagg tgcatgattt    60
taaatgggaa ggaatgatta aaagagatat aaattggctg tcaatgatga aggatttcta   120
tagggttgtg ttagtaaatt tgaaaattgt attctgttga tattttctgc acaccaatca   180
tgctagatgc ccaatggttc ctttttata tattctatga ttccatactc accttcaata   240 catgttttt ttttaaaaaa aaggtttgaa caattaactg agttgaatag tagtaaaagc   300
atgaagtgtt ttgttttgt tttgtgggga tgtatgaata agaaaaatca ttacaaccag   360
acaaagatgt aactcagaag aaagagtaat aagtctattt gcaagaacat aaccgtgcta   420
aaatcctttg aaaatacact ggaactagct gataatttta cagtttccag tggtgcaatt   480
ctcaaccatt aaccaatttt atctaaaact atcagctttc cagtcatgaa cctccatacc   540
gaaaatttgt cgcctatttc ttttattggc agtggctttt gtcatatttt tgccaggcta   600
aattataaca gtatcacact ctttgaactt catttaatac ctttgaatat tgtgttttat   660
agttatctca tggaatgtat tttaagataa ggttgttgtg aattgtttgg ttgagtgcat   720
ggatttgctg atgaccatag ctatttgtgg atattatgtt ttcaaaatgt atgcttggtc   780
attaatcaac caagaatgat aagccccatc atctactacc ccttctatac catatacata   840
ttttgcttat ctacattgca attcttgcta aacaaatcta gcagataaca tgcaaactaa   900
tgaacttttt tagtaatatt ataaaaatca gccagagtaa gctgaagaga gaaacacgtt   960
ttcagctata aaacaaaagg gataagagtg tcagttgagt gatatggttc tattttatt  1020 tttttaatt caaaatcacc tttaaaatat aaaacattac tgtaggaaaa ggacaaaggg  1080 tattccaccat aaaagagaaa tggtcacaaa atatgtaagg taaatatgga atgagggcac  1140
agtgcaaact actcacaaat aacctcaact ccaccagcat cacacattta cattcttcca  1200
aggaagagat aagataatgg agctcctcca cgtgtcactt ccacatggta cctaaggata  1260
aggctagctt tcaaaatttt gctgactcgt gtggccagta tgctgtaatg tcatcactta  1320
tagaatccga cggttgtaac atctcagcaa gcaatcccct ccatctcaca ccattggatc  1380
agtactatac aaatgatagt attatataaa gcaagtagga gcagaagctt gggcatctag  1440
cagcagaaca gcaagtgatt cagaagtaag aagaagaaga aggaaatggc ttcttcaatg  1500
atctcctccc ccgctgtgac gaccgttaac cgtgccggtg ccggtgccgg tatggtggct  1560
cctttcactg ggctgaagtc cctgggaggg ttcccaagca ggaagatgaa caatgatatt  1620
acttccgttg cgaacaacgg tggaagagtg caatgcattc aggtaagaga agatatttat  1680
gtgataggaa aatgtgaaga tttggaagtt ggttggttag ttagtttgtt aactgaatta  1740
tgatggaaat gaaatgagta ggtgtggcca acagttggga agaagaagtt cgagactctt  1800
tcgtacctgc caccctgac aaaacaacaa ttggcaaagg aagtagacta ccttcttcgg  1860
aaaggatggg ttccgtgctt ggaattc                                    1887

<210> SEQ ID NO 44
<211> LENGTH: 435
<212> TYPE: DNA
<213> ORGANISM: P. sativum
```

<400> SEQUENCE: 44

```
gatccaaaag cttggacagg aacaaatgtt acccatacat aaaagatatt tgtgaagtaa      60
cagtcacaaa attccatgag gccaacatac tacaattgaa ttttcatgga tacaattctt     120
acaaataaa aatatcgaca taaccaccat cacacattta cactcttcac atgaaaagat     180
aagatcagtg aggtaatatc cacatggcac tgtcctattg gtggcttatg ataaggctag     240
cacacaaaat ttcaaatctt gtgtggttaa tatggctgca aactttatca ttttcactat     300
ctaacaagat tggtactagg cagtagctaa gtaccacaat attaagacca taatattgga     360
aatagataaa taaaaacatt atatatagca agttttagca gaagctttgc aattcataca     420
gaagtgagaa aaatg                                                       435
```

<210> SEQ ID NO 45
<211> LENGTH: 1666
<212> TYPE: DNA
<213> ORGANISM: P. sativum

<400> SEQUENCE: 45

```
ctgcagtttt tcaaagaaat tatcttttgt tccttttgc cttgtaactt aacaataatg      60
gcgtaaataa taataaccat gattgacttg aactttggta aacaattata attaaccata     120
tactagtata ttagatttca gtaatcatga attaaaattg acgagtgcat gtctaaccaa     180
ccatcaagta ttacttggtt cttttcacaa tttgtctacc ttacctttat cttctttatt     240
acacttggtt cttttctcaa atttcgacgc gtgttgatgt aatattggta taaacagaaa     300
ctacaaaacg cagctgtcca taacagtcac aattttctc aaatcttgtg gctctcaaac     360
actgtataaa acatgacaaa tgtggaccca aaatagagaa agcatagccc cataaattaa     420
gccattttat gaaaaataa tattatgttg agtcatatat ccataagaat ccccacagtc     480
acacatggaa gagcagcatt ggatacaaat gatatgaaga ttttgatcca tgaacggatt     540
ctagaattgc aagaaaatc tccaactagc catagcttta gataacacac gataagagca     600
tctgcattat aaatacagac tcatattcat cttacaaaat caccattgat aaggatacaa     660
ttatcaaaag cataacaatc ttttcaattt cattgcaata taatacacga tggccgcatc     720
atcatcatca tccatggctc tctcttctcc aaccttggct ggcaagcaac tcaagctgaa     780
cccatcaagc caagaattgg gagctgcaag gttcaccatg aggaagtctg ctaccaccaa     840
gaaagtagct tcctctggaa gcccatggta cggaccagac cgtgttaagt acttaggccc     900
attccggt gagtctccat cctacttgac aggagagttc cccggtgact acggttggga     960
cactgccgga ctctctgctg acccagagac attctccaag aaccgtgagc ttgaagtcat    1020
ccactccaga tgggctatgt tgggagcttt gggatgtgtc ttcccagagc ttttgtctcg    1080
caacggtgtt aaattcggcg aagctgtgtg gttcaaggca ggatctcaaa tctttagtga    1140
gggtggactt gattacttgg gcaacccaag cttggtccat gctcaaagca tccttgccat    1200
atgggccact caggttatct tgatgggagc tgtcgaaggt taccgtattg ccggtgggcc    1260
tctcggtgag gtggttgatc cacttaccc aggtggaagc tttgatccat gggcttagc    1320
tgatgatcca gaagcattcg cagaattgaa ggtgaaggaa ctcaagaacg gtagattagc    1380
catgttctca atgtttggat tcttcgttca agctattgta actggaaagg gtcctttgga    1440
gaaccttgct gatcatcttg cagacccagt caacaacaat gcatggtcat atgccaccaa    1500
cttttgttccc ggaaaataa cactcttata tttatatgtt tttgtgatag taatcttctt    1560
```

```
cccaattcaa tgtgaattat tatcattatc attatcatgt gggtatgcat aggttcacta   1620
atacaagatc atggatgttt tcttttacc aaatttaaa ttttat                   1666

<210> SEQ ID NO 46
<211> LENGTH: 4955
<212> TYPE: DNA
<213> ORGANISM: G. max

<400> SEQUENCE: 46
tcgacgtgta cttaaaacct ccgccgcagc tggtggtgtt gaagctgacg gtgttgccgg     60
tgaactcgaa ggagaagata gagattattc tgtcatcagt gttggcggga tacaccaaag    120
ggttacacca acacgaggag ccaaataaat gcatgtgggt tacgccaaca gcaccaagga    180 gaaatacccca tgcatgcatc attatcaccg atccatagtt gtgcatccgg taacgaactt    240
agcggggaag ttagttagtt gttgcatatt aaggaataag aatttagagc tgtatgagtc    300
atgagtaata tacagcttag ctagctgaac ttcgacaata gaaacacagc aacctttccg    360
gtcatattta atttcaatca gaaattttga ataagggta atccaattct catgtaattt     420
atatatttca caacagtttt caaaattagg aaaagaaaa ataaaaagt atgaaactaa      480 taagttattt tatatatttc acaacagttt tcagaattta aataagagt aatccaattc     540 tcatgtatct tttttatttt tttttaacac tccaaacttt aaacacttaa ccaacatgat    600
ccttgaatat gtaacaagtt attattgtct atgatgagtt gagttgtttg gcaccagtta    660
aaaacttctt aaaattagcc tcaaatgaag gattaaaata ggtttaatat agattaattt    720
gagcaataaa aataaataaa tgaaactttt tttagaaaga cttgctgacg gaaaatgaat    780
agccctcaaa aaattgaaat atgaacaaat tgaaaaacta aatctcaatt ttaaaaaact    840
atatatatgc atacgggcta acatggttag gggcttaggc ttcctcattg tcctaaaagc    900
aaatattcgt ttgggccttg gttctccagt aagttttta attgggctca agaactttag    960
gatttagatg aggatcaata aaaattgata tattgcgctt gcttgttttt ttttttcat   1020 taaatttacg caaaaatgaa agaaaaaggt attcacgctc ttaaaataaa ttaataagca  1080
gaaattccaa aattttcagt tagtccttac taattattaa attatagtat taatccaatg  1140
tgattgcggt tacatcatgt acggaaaaat aattctaatc cttgatttaa atttgatctt  1200
gactatttat ttattcttta tttcatttg taaatcattt tatgtatccc ctggcaaggc   1260
aattttatcc accttgcacc caacacttcg ggtcccataa atcaaaccac cttaacttca  1320
cacaatgctg taactcacac cgcccagcat ctccaatgtg aaagaagcta aaatttaata  1380
aacaatcata cgaagcagtg acaaaatacc agatggtatt aatgctttga taaaattaat  1440
tggaaagtat aaaatggtag gaaataatta attataatta atttaaataa gattaaaaat  1500
aatttaaaac taaaatgtta aaatttaag aaaattattt taaataatat ttaaaaacat    1560
ttaaaatcat tttaaaaaat ttatttatag gacaattaaa tgaatatttc agctaattaa   1620
aaacaaaagc ttacctagcc ttagaagaca acttgtccaa caattagatg atacccattg    1680
cccttacgtt ttctttaaca tcaattattg ttttttgtcaa caagctatct tttagttta    1740 ttttattggt aaaaaatatt gtcgccttca agttgcatca tttaacacat ctcgtcatta    1800
gaaaataaaa actcttccct aaacgattag tagaaaaaat cattcgataa taaataagca    1860
agcaaaatta ggaaaaaata acttcatttt aaaaaaatca ttaaggctat attttttaaa   1920
tgactaattt tatatagact gtaactaaaa gtatacaatt tattatgcta tgtatcttaa    1980
agaattactt ataaaaatct acggaagaat atcttacaaa gtgaaaaaca aatgagaaag   2040
```

```
aatttagtgg gatgattatg attttatttg aaaattgaaa aaataattat taaagacttt      2100
agtggagtaa gaaagctttc ctattagtct tttcttatcc ataaaaaaaa aaaaaaaaat      2160
ctagcgtgac agcttttcca tagattttaa taatgtaaaa tactggtagc agccgaccgt      2220
tcaggtaatg gacactgtgg tcctaacttg caacgggtgc gggcccaatt taataacgcc      2280
gtggtaacgg ataaagccaa gcgtgaaggg gtgaaggtac atctctgact ccgtcaagat      2340
tacgaaaccg tcaactacga aggactcccc gaaatatcat ctgtgtcata aacaccaagt      2400
cacaccatac atgggcacgc gtcacaatat gattggagaa cggttccacc gcatatgcta      2460
taaattgccc ccacacccct cgaccctaat cgcacttgaa ttgcaatcaa attagttcat      2520
tctctttgcg cagttcccta cctcccccctt tcaaggtccg tagattcctc ctgttttttt      2580
ttcttcttct ttattgtttg ttctacatca gcatgatgtt gatttgattg tgttttctat      2640
cgtttcatcg attataaatt ttcataatca gaagattcag cttttattaa tgcaagaacg      2700
tccttaattg atgattttat aaccgtaaat taggtctaat tagagttttt ttcataaaga      2760
ttttcagatc cgtttacaac aagccttaat tgttgattct gtagtcgtag attaaggttt      2820
ttttcatgaa ctacttcaga tccgttaaac aacagcctta tttgttgata cttcagtcgt      2880
ttttcaagaa attgttcaga tccgttgata aaagccttat tcgttgattc tgtatggtat      2940
ttcaagagat attgctcagg tcctttagca actaccttat ttgttgattc tgtggccata      3000
gattaggatt tttttttcacg aaattgcttc ttgaaattac gtgatggatt ttgattctga      3060
tttatcttgt gattgttgac tctacagatg cagatcttcg tcaagaccct caccggaaag      3120
accatcaccc ttgaggtgga aagctctgac accatcgaca acgtcaaggc caagatccag      3180
gacaaggaag gaattccccc ggaccagcaa cgtctcatct ttgccggaaa gcagctcgag      3240
gacggccgta ccctcgccga ctacaacatc cagaaggagt caacccttca ccttgtcctt      3300
cgtctccgtg gtggcatgca gatcttcgtc aagactctca ctggcaaaac cataacccta      3360
gaggtcgaaa gctctgacac cattgacaac gtcaaggcca agatccagga caaggaggga      3420
atcccccccag accagcaacg tctcatcttc gccggaaagc aacttgagga cgggcgcacc      3480
ctcgccgact acaacatcca gaaggaatca acccttcacc tcgtcctccg tctccgtggt      3540
ggcatgcaga tcttcgttaa gaccctcacc ggcaagacta taaccctaga agtcgagagc      3600
tccgacacca tcgacaacgt caaggctaag atccaggaca aggagggtat ccccccagac      3660
cagcagaggc tgatcttcgc cggcaagcag ctcgaggacg gacgtaccct tgctgactac      3720
aacatccaga aggagtcaac tctccacttg gtgttgcgtc ttcgtggtgg tatgcagatc      3780
ttcgtcaaga cccttacggg taagactatt accctcgagg tggagagctc cgacaccatt      3840
gacaatgtga aggcgaagat ccaggacaag gaaggaatcc caccggacca gcagaggctt      3900
atttttgctg gcaaacagct agaggatgga aggaccctcg ctgactacaa catccagaag      3960
gagtcaactc tgcacttggt gttgcgtctt cgtggggggt tttaagctgg agctgatttc      4020
tgtgtgatgt tcgatgttgg attttcccaa acatttttaag aagaaatgtg atgtgtaatg      4080
ggtctgtaat gaccttttgaa aataagtttg gtttgtgttg aactctattg tcccattaat      4140
gttactactg tttgttatca atttgtggag ctgatatata attatcaact gtatgctggc      4200
atattgtgtt tgaattttgt tctcaatcca gtgaattggc gtatattagt gggtttttta      4260
ttcttcatgc ttatcacgga ggaaaagcag ggatgagttg tgtgaaggat ggtgatcatc      4320
ccacgaatta ttagattttg gtattatagg ttaaagatat ttattaggta gggagaactc      4380
```

| | |
|---|---|
| ttggattaga ttctaaagtg atattttgaa aacacaccaa aggattttg aacaaacgga | 4440 |
| gatcatgatc cctagtttca attagctgcc ccttaccaag aggtagcaac ttaaaaatta | 4500 |
| tgctcgtgaa gcatatttgg tatcgtatat aaattatgta agcaatctgc ttcagttgga | 4560 |
| acattaattg gcttgcggaa tgcacattta gatgatccac acaggtccac ataaaaattc | 4620 |
| ctaatcaatt ttagttatgc aatctttctg cttcaggtag tccttgtctt acagaaagca | 4680 |
| cattgagatg atccccacac agatcccaca taaaaaattc ctaatcaata taacttgaa | 4740 |
| aatcattaaa agatgtaatg ccatactaat ccctaattt tgtgcaagtt tttgtatact | 4800 |
| gggccccaaa aaataccaaa aagaaaaaac aagttattca gtgatatttt tctgctccaa | 4860 |
| tataaatttg attaccaaat accaaaaaat aaaaacacta ttcagtggta tttttctgct | 4920 |
| ccaatactgg accccaaatt aattagaatc ggatc | 4955 |

<210> SEQ ID NO 47
<211> LENGTH: 1351
<212> TYPE: DNA
<213> ORGANISM: A. thaliana

<400> SEQUENCE: 47

| | |
|---|---|
| aggatattct tgtttaagat gttgaactct atggaggttt gtatgaactg atgatctagg | 60 |
| accggataag ttcccttctt catagcgaac ttattcaaag aatgttttgt gtatcattct | 120 |
| tgttacattg ttattaatga aaaaatatta ttggtcattg gactgaacac gagtgttaaa | 180 |
| tatggaccag gccccaaata agatccattg atatatgaat taaataacaa gaataaatcg | 240 |
| agtcaccaaa cccacttgcct tttttaacga gacttgttca ccaacttgat acaaaagtca | 300 |
| ttatcctatg caaatcaata atcatacaaa aatatccaat aacactaaaa aattaaaaga | 360 |
| aatggataat ttcacaatat gttatacgat aaagaagtta cttttccaag aaattcactg | 420 |
| atttttataag cccacttgca ttagataaat ggcaaaaaaa aacaaaaagg aaaagaaata | 480 |
| aagcacgaag aattctagaa aatacgaaat acgcttcaat gcagtgggac ccacggttca | 540 |
| attattgcca attttcagct ccaccgtata tttaaaaaat aaaacgataa tgctaaaaaa | 600 |
| atataaatcg taacgatcgt taaatctcaa cggctggatc ttatgacgac cgttagaaat | 660 |
| tgtggttgtc gacgagtcag taataaacgg cgtcaaagtg gttgcagccg gcacacacga | 720 |
| gtcgtgttta tcaactcaaa gcacaaatac ttttcctcaa cctaaaaata aggcaattag | 780 |
| ccaaaaacaa cttttgcgtgt aaacaacgct caatacacgt gtcatttat tattagctat | 840 |
| tgcttcaccg ccttagcttt ctcgtgacct agtcgtcctc gtctttctt cttcttcttc | 900 |
| tataaaacaa tacccaaaga gctcttcttc ttcacaattc agatttcaat ttctcaaaat | 960 |
| cttaaaaact ttctctcaat tctctctacc gtgatcaagg taaatttctg tgttccttat | 1020 |
| tctctcaaaa tcttcgattt tgttttcgtt cgatcccaat ttcgtatatg ttctttggtt | 1080 |
| tagattctgt taatcttaga tcgaagacga ttttctgggt ttgatcgtta gatatcatct | 1140 |
| taattctcga ttagggtttc atagatatca tccgatttgt tcaaataatt tgagttttgt | 1200 |
| cgaataatta ctcttcgatt tgtgatttct atctagatct ggtgttagtt tctagttttgt | 1260 |
| gcgatcgaat ttgtcgatta atctgagttt ttctgattaa cagatgcaga tctttgttaa | 1320 |
| gactctcacc ggaaagacaa tcaccctcga g | 1351 |

<210> SEQ ID NO 48
<211> LENGTH: 8024
<212> TYPE: DNA
<213> ORGANISM: Cauliflower mosaic virus

<400> SEQUENCE: 48

```
ggtatcagag ccatgaatcg gtttaagacc aaaactcaag agggtaaaac ctcaccaaaa      60
tacgaaagag ttcttaactc taaaaataaa agatctttca agatcaaaca tagttccctc     120
acaccggtga ccgacaggat taccaccgta aggtttcaga acaacatcga aagcgtttac     180
gccaacttcg actctcaact caagtcgtcg tacgatggta gatctaaaaa gatcaagact     240
ctaagcctta aaaatcttag atgttacgaa gccttcctca ggaagtacct tctggaacaa     300
taaatctctc tgagaatagt actctattga gtatccacag gaaaaataac cttctgtgtt     360
gagatggatt tgtatccaga agaaaatacc caaagcgagc aatcgcagaa ttctgaaaat     420
aatatgcaaa tatttaaatc agaaaattcg gatggattct cctccgatct aatgatctca     480
aacgatcaat taaaaaatat ctctaaaacc caattaacct tggagaaaga aaagatattt     540
aaaatgccta acgttttatc tcaagttatg aaaaaagcgt ttagcaggaa aaacgagatt     600
ctctactgcg tctcgacaaa agaattatca gtggacattc acgatgccac aggtaaggta     660
tatcttccct taatcactaa ggaagagata aataaaagac tttccagctt aaaacctgaa     720
gtcagaaaga ccatgtccat ggttcatctt ggagcggtca aaatattgct taaagctcaa     780
tttcgaaatg ggattgatac cccaatcaaa attgctttaa tcgatgatag aatcaattct     840
agaagagatt gtcttcttgg tgcagccaaa ggtaatctag catacggtaa gtttatgttt     900
actgtatacc ctaagtttgg aataagcctt aacacccaaa gacttaacca aaccctaagc     960
cttattcatg atttttgaaaa taaaaatctt atgaataaag gtgataaagt tatgaccata    1020
acctatgtcg taggatatgc attaactaat agtcatcata gcatagatta tcaatcaaat    1080
gctacaattg aactagaaga cgtatttcaa gaaattggaa atgtccagca atctgagttc    1140
tgtacaatac agaatgatga atgcaattgg gccattgata tagcccaaaa caaagcctta    1200
ttaggagcta aaaccaagac tcaaattggt aataaccttc aaataggtaa cagtgcttca    1260
tcctctaata ctgaaaatga attagctagg gtaagccaga acatagatct tttaaagaat    1320
aaattaaaag aaatctgtgg agaataatat gagcattacg ggacaaccgc atgtttataa    1380
aaaagatact attattagac taaaaccatt gtctcttaat agtaataata gaagttatgt    1440
ttttagttcc tcaaaaggga acattcaaaa tataattaat catcttaaca acctcaatga    1500
gattgtagga agaagcttac tcggaatatg gaagatcaac tcatacttcg gattaagcaa    1560
agacccttcg gagtccaaat caaaaaaccc gtcagttttt aatactgcaa aaaccatttt    1620
taagagtggg ggggttgatt actcgagcca actaaaggaa ataaaatccc ttttagaagc    1680
tcaaaacact agaataaaaa gtctagaaaa agcaattcaa tccttagaaa ataagattga    1740
accagagccc ttaactaaag aggaagttaa agagctaaaa gaatcgatta actcgatcaa    1800
agaaggatta agaatatta ttggctaaaa tggctaatct taatcagatc caaaagaag     1860
tctctgaaat cctcagtgac caaaaatcca tgaaagcgga tataaagct atcttagaat     1920
tattaggatc ccaaaatcct attaaagaaa gcttagaaac cgttgcagca aaaatcgtta    1980
atgacttaac caagctcatc aatgattgtc cttgtaacaa agagatatta gaagccttag    2040
gtacccaacc taaagagcaa ctaatagaac aacctaaaga aaaaggtaaa ggccttaact    2100
taggaaaata ctcttacccc aattacggag taggaaatga agaattagga tcctctggaa    2160
accctaaagc tttaacctgg cccttcaaag ctccagcagg atggccgaat caattttaga    2220
cagaaccatt aataggtttt ggtataatct gggagaagat tgtctctcag aaagtcaatt    2280
```

```
cgatcttatg ataagattga tggaagagtc ccttgacggg gaccaaatta ttgatctaac    2340
ctctctacct agtgataatt tgcaggttga acaggttatg acaactaccg aagactcaat    2400
ctcggaagaa gaatcagaat tccttctagc aataggagaa acatctgaag aagaaagcga    2460
ttcaggagaa gaacctgaat tcgagcaagt tcgaatggat cgaacaggag aacggagat    2520
tccaaaagaa gaagatggtg aaggaccatc tagatacaat gagagaaaga gaaagacccc    2580
ggaggaccgg tactttccaa ctcaaccaaa gaccattcca ggacaaaagc aaacgtctat    2640
gggaatgctc aacattgact gccaaaccaa tcgaagaact ctaatcgacg actgggcagc    2700
agaaatcgga ttgatagtca agaccaaatag agaagactat ctcgatccag aaacaattct    2760
actcttgatg gaacacaaaa catcaggaat agccaaggag ttaatccgaa atacaagatg    2820
gaaccgcact accggagaca tcatagaaca ggtgatcgat gcgatgtaca ccatgttctt    2880
aggactaaac tactccgaca acaaagttgc tgagaagatt gacgagcaag agaaggccaa    2940
gatcagaatg accaagctcc agctctgcga catctgctac cttgaggaat ttacatgtga    3000
ttatgaaaag aacatgtata agacagaact ggcggatttc ccaggatata tcaaccagta    3060
cctgtcaaaa atccccatca ttggagaaaa agcgttaaca cgctttaggc atgaagctaa    3120
cggaaccagc atctacagtt taggtttcgc ggcaaagata gtcaagaag aactatctaa    3180
aatctgcgac ttatccaaga agcagaagaa gttgaagaaa ttcaacaaga agtgttgtag    3240
catcggagaa gcttcaacag aatatggatg caagaagaca tccacaaaga agtatcacaa    3300
gaagcgatac aagaaaaaat ataaggctta caaaccttat aagaagaaaa agaagttccg    3360
atcaggaaaa tacttcaagc ccaaagaaaa gaagggctca aagcaaaagt attgcccaaa    3420
aggcaagaaa gattgcagat gttggatctg caacattgaa ggccattacg ccaacgaatg    3480
tcctaatcga caaagctcgg agaaggctca catccttcaa caagcagaaa aattgggtct    3540
ccagcccatt gaagaaccct atgaaggagt tcaagaagta ttcattctag aatacaaaga    3600
agaggaagaa gaaacctcta cagaagaaag tgatggatca tctacttctg aagactcaga    3660
ctcagactga gcaggtgatg aacgtcacca atcccaattc gatctacatc aagggaagac    3720
tctacttcaa gggatacaag aagatagaac ttcactgttt cgtagacacg ggagcaagcc    3780
tatgcatagc atccaagttc gtcataccag aagaacattg ggtcaatgca gaaagaccaa    3840
ttatggtcaa aatagcagat ggaagctcaa tcaccatcag caaagtctgc aaagacatag    3900
acttgatcat agccggcgag atattcagaa ttcccaccgt ctatcagcaa gaaagtggca    3960
tcgatttcat tatcggcaac aacttctgtc agctgtatga accattcata cagtttacgg    4020
atagagttat cttcacaaag aacaagtctt atcctgttca tattgcgaag ctaaccagag    4080
cagtgcgagt aggcaccgaa ggatttcttg aatcaatgaa gaaacgttca aaaactcaac    4140
aaccagagcc agtgaacatt tctacaaaca agatagaaaa tccactagaa gaaattgcta    4200
ttctttcaga ggggaggagg ttatcagaag aaaaactctt tatcactcaa caaagaatgc    4260
aaaaaatcga agaactactt gagaaagtat gttcagaaaa tccattagat cctaacaaga    4320
ctaagcaatg gatgaaagct tctatcaagc tcagcgaccc aagcaaagct atcaaggtta    4380
aaccatgaa gtatagccca atggatcgcg aagaatttga caagcaaatc aaagaattac    4440
tggacctaaa agtcatcaag cccagtaaaa gccctcacat ggcaccagcc ttcttggtca    4500
acaatgaagc cgagaagcga agaggaaaga aacgtatggt agtcaactac aaagctatga    4560
acaaagctac tgtaggagat gcctacaatc ttcccaacaa agacgagtta cttcactca    4620
ttcgaggaaa gaagatcttc tcttccttcg actgtaagtc aggattctgg caagttctgc    4680
```

```
tagatcaaga atcaagacct ctaacggcat tcacatgtcc acaaggtcac tacgaatgga    4740
atgtggtccc tttcggctta aagcaagctc catccatatt ccaaagacac atggacgaag    4800
catttcgtgt gttcagaaag ttctgttgcg tttatgtcga cgacattctc gtattcagta    4860
acaacgaaga agatcatcta cttcacgtag caatgatctt acaaaagtgt aatcaacatg    4920
gaattatcct ttccaagaag aaagcacaac tcttcaagaa gaagataaac ttccttggtc    4980
tagaaataga tgaaggaaca cataagcctc aaggacatat cttggaacac atcaacaagt    5040
tccccgatac ccttgaagac aagaagcaac ttcagagatt cttaggcata ctaacatatg    5100
cctcggatta catcccgaag ctagctcaaa tcagaaagcc tctgcaagcc aagcttaaag    5160
aaaacgttcc atggagatgg acaaagagg ataccctcta catgcaaaag gtgaagaaaa    5220
atctgcaagg atttcctcca ctacatcatc ccttaccaga ggagaagctg atcatcgaga    5280
ccgatgcatc agacgactac tggggaggta tgttaaaagc tatcaaaatt aacgaaggta    5340
ctaatactga gttaatttgc agatacgcat ctggaagctt taaagctgca gaaaagaatt    5400
accacagcaa tgacaaagag acattggcgg taataaatac tataaagaaa tttagtattt    5460
atctaactcc tgttcatttt ctgattagga cagataatac tcatttcaag agtttcgtta    5520
atctcaatta caaaggagat tcgaaacttg aagaaacat cagatggcaa gcatggctta    5580
gccactattc atttgatgtt gaacacatta aggaaccga caaccacttt gcggacttcc    5640
tttcaagaga attcaataag gttaattcct aattgaaatc cgaagataag attcccacac    5700
acttgtggct gatatcaaaa ggctactgcc tatttaaaca catctctgga gactgagaaa    5760
atcagacctc caagcatgga gaacatagaa aaactcctca tgcaagagaa aatactaatg    5820
ctagagctcg atctagtaag agcaaaaata agcttagcaa gagctaacgg ctcttcgcaa    5880
caaggagacc tctctctcca ccgtgaaaca ccggaaaaag aagaagcagt tcattctgca    5940
ctggctactt ttacgccatc tcaagtaaaa gctattccag agcaaacggc tcctggtaaa    6000
gaatcaacaa atccgttgat ggctaatatc ttgccaaaag atatgaattc agttcagact    6060
gaaattaggc ccgtaaagcc atcggacttc ttacgtccac atcagggaat tccaatccca    6120
ccaaaacctg aacctagcag ttcagttgct cctctcagag acgaatcggg tattcaacac    6180
cctcatacca actactacgt cgtgtataac ggacctcatg ccggtatata cgatgactgg    6240
ggttgtacaa aggcagcaac aaacggtgtt cccggagttg cgcataagaa gtttgccact    6300
attacagagg caagagcagc agctgacgcg tatacaacaa gtcagcaaac agataggttg    6360
aacttcatcc ccaaaggaga agctcaactc aagcccaaga gctttgcgaa ggccttaaca    6420
agcccaccaa agcaaaaagc ccactggctc atgctaggaa ctaaaaagcc cagcagtgat    6480
ccagccccaa aagagatctc ctttgcccca gagatcacaa tggacgactt cctctatctc    6540
tacgatctag tcaggaagtt cgacggagaa ggtgacgata ccatgttcac cactgataat    6600
gagaagatta gccttttcaa tttcagaaag aatgctaacc cacagatggt tagagaggct    6660
tacgcagcag gtctcatcaa gacgatctac ccgagcaata atctccagga gatcaaatac    6720
cttcccaaga aggttaaaga tgcagtcaaa agattcagga ctaactgcat caagaacaca    6780
gagaaagata tatttctcaa gatcagaagt actattccag tatggacgat tcaaggcttg    6840
cttcacaaac caaggcaagt aatagagatt ggagtctcta aaaaggtagt tcccactgaa    6900
tcaaaggcca tggagtcaaa gattcaaata gaggacctaa cagaactcgc cgtaaagact    6960
ggcgaacagt tcatacagag tctcttacga ctcaatgaca agaagaaaat cttcgtcaac    7020
```

-continued

```
atggtggagc acgacacgct tgtctactcc aaaaatatca agatacagt ctcagaagac    7080 caaagggcaa ttgagacttt tcaacaaagg gtaatatccg gaaacctcct cggattccat    7140
tgcccagcta tctgtcactt tattgtgaag atagtggaaa aggaaggtgg ctcctacaaa    7200
tgccatcatt gcgataaagg aaaggccatc gttgaagatg cctctgccga cagtggtccc    7260
aaagatggac ccccacccac gaggagcatc gtggaaaaag aagacgttcc aaccacgtct    7320
tcaaagcaag tggattgatg tgatatctcc actgacgtaa gggatgacgc acaatcccac    7380
tatccttcgc aagacccttc ctctatataa ggaagttcat ttcatttgga gaggacacgc    7440
tgaaatcacc agtctctctc tacaaatcta tctctctcta taataatgtg tgagtagttc    7500
ccagataagg gaattagggt tcttataggg tttcgctcat gtgttgagca tataagaaac    7560
ccttagtatg tatttgtatt tgtaaaatac ttctatcaat aaaatttcta attcctaaaa    7620
ccaaaatcca gtactaaaat ccagatctcc taaagtccct atagatcttt gtggtgaata    7680 taaccagac acgagacgac taaacctgga gcccagacgc cgtttgaagc tagaagtacc    7740
gcttaggcag gaggccgtta gggaaaagat gctaaggcag ggttggttac gttgactccc    7800
ccgtaggttt ggtttaaata tcatgaagtg gacggaagga aggaggaaga caaggaagga    7860
taaggttgca ggccctgtgc aaggtaagac gatggaaatt tgatagaggt acgttactat    7920
acttatacta tacgctaagg gaatgcttgt atttacccta tatacctaa tgaccccta    7980 tcgatttaaa gaataatcc gcataagccc ccgcttaaaa aatt                     8024
```

<210> SEQ ID NO 49
<211> LENGTH: 145
<212> TYPE: PRT
<213> ORGANISM: S. indicum

<400> SEQUENCE: 49

```
Met Ala Cys His Tyr Gly Gln Gln Gln Thr Cys Ala Pro His Leu
1               5                   10                  15

Gln Leu Gln Pro Arg Ala Cys Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Cys
            100                 105                 110

Leu Glu Ser Ala Lys Thr Lys Leu Ala Ser Cys Ala Arg Glu Met Lys
        115                 120                 125

Asp Arg Ala Glu Gln Phe Ser Cys Gln Pro Val Ala Gly Ser Gln Thr
    130                 135                 140

Ser
145
```

<210> SEQ ID NO 50
<211> LENGTH: 518
<212> TYPE: PRT
<213> ORGANISM: T. majus

<400> SEQUENCE: 50

```
Met Ala Val Ala Glu Ser Ser Gln Asn Thr Thr Met Ser Gly His
1               5                   10                  15

Gly Asp Ser Asp Leu Asn Asn Phe Arg Arg Lys Pro Ser Ser Ser
            20                  25                  30

Val Ile Glu Pro Ser Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly
65                  70                  75                  80

Val Val Ile Gly Asn Glu Glu Lys Gln Val Gly Glu Thr Asp Ile Arg
            85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Ile Val Val Leu Ile Ala Val Asn Ser Arg Leu Ile Ile
        130                 135                 140

Glu Asn Leu Met Lys Tyr Gly Trp Leu Ile Asp Thr Gly Phe Trp Phe
145                 150                 155                 160

Ser Ser Arg Ser Leu Gly Asp Trp Ser Ile Phe Met Cys Cys Leu Thr
            165                 170                 175

Leu Pro Ile Phe Pro Leu Ala Ala Phe Ile Val Glu Lys Leu Val Gln
        180                 185                 190

Arg Asn His Ile Ala Glu Leu Val Ala Leu Leu His Val Ile Val
        195                 200                 205

Ser Thr Ala Ala Val Leu Tyr Pro Val Ile Val Leu Thr Cys Asp
210                 215                 220

Ser Val Tyr Met Ser Gly Val Val Leu Met Leu Phe Gly Cys Ile Met
225                 230                 235                 240

Trp Leu Lys Leu Val Ser Tyr Ala His Thr Ser Ser Asp Ile Arg Thr
            245                 250                 255

Leu Ala Lys Ser Gly Tyr Lys Gly Asp Ala His Pro Asn Ser Thr Ile
            260                 265                 270

Val Ser Cys Ser Tyr Asp Val Ser Leu Lys Ser Leu Ala Tyr Phe Met
            275                 280                 285

Val Ala Pro Thr Leu Cys Tyr Gln Pro Ser Tyr Pro Arg Ser Ser Cys
            290                 295                 300

Ile Arg Lys Gly Trp Val Arg Gln Phe Val Lys Leu Ile Val Phe
305                 310                 315                 320

Ile Gly Leu Met Gly Phe Ile Ile Glu Gln Tyr Ile Asn Pro Ile Val
            325                 330                 335

Arg Asn Ser Lys His Pro Leu Lys Gly Asp Phe Leu Tyr Ala Ile Glu
            340                 345                 350

Arg Val Leu Lys Leu Ser Val Pro Asn Leu Tyr Val Trp Leu Cys Met
            355                 360                 365

Phe Tyr Ser Phe Phe His Leu Trp Leu Asn Ile Leu Ala Glu Leu Leu
370                 375                 380

Arg Phe Gly Asp Arg Glu Phe Tyr Lys Asp Trp Trp Asn Ala Lys Thr
385                 390                 395                 400

Val Ala Glu Tyr Trp Lys Met Trp Asn Met Pro Val His Arg Trp Met
            405                 410                 415
```

-continued

```
Val Arg His Leu Tyr Phe Pro Cys Leu Arg Asn Gly Ile Pro Lys Glu
            420                 425                 430

Gly Ala Ile Ile Ile Ala Phe Leu Val Ser Gly Ala Phe His Glu Leu
        435                 440                 445

Cys Ile Ala Val Pro Cys His Val Phe Lys Leu Trp Ala Phe Ile Gly
    450                 455                 460

Ile Met Phe Gln Val Pro Leu Val Leu Ile Thr Asn Tyr Leu Gln Glu
465                 470                 475                 480

Lys Phe Ser Asn Ser Met Val Gly Asn Met Ile Phe Trp Phe Ile Phe
                485                 490                 495

Cys Ile Leu Gly Gln Pro Met Cys Val Leu Leu Tyr Tyr His Asp Leu
            500                 505                 510

Ile Asn Leu Lys Glu Lys
        515

<210> SEQ ID NO 51
<211> LENGTH: 14
<212> TYPE: PRT
<213> ORGANISM: Artificial Sequence
<220> FEATURE:
<223> OTHER INFORMATION: synthetic construct

<400> SEQUENCE: 51

Gly Lys Pro Ile Pro Asn Pro Leu Leu Gly Leu Asp Ser Thr
1               5                   10
```